United States Patent
Marino, Jr. et al.

(10) Patent No.: US 7,304,082 B2
(45) Date of Patent: Dec. 4, 2007

(54) 1,2,4-TRIAZOLE DERIVATIVES, COMPOSITIONS, PROCESS OF MAKING AND METHODS OF USE

(75) Inventors: Joseph P. Marino, Jr., King of Prussia, PA (US); Scott K. Thompson, King of Prussia, PA (US); Daniel Frank Veber, Ambler, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 11/186,519

(22) Filed: Jul. 21, 2005

(65) Prior Publication Data

US 2005/0267185 A1 Dec. 1, 2005

Related U.S. Application Data

(63) Continuation of application No. 10/089,433, filed as application No. PCT/US00/26951 on Sep. 29, 2000, now abandoned.

(60) Provisional application No. 60/157,286, filed on Oct. 1, 1999.

(51) Int. Cl.
*A61K 31/4196* (2006.01)
*C07D 249/14* (2006.01)

(52) U.S. Cl. .................... 514/384; 548/263.8

(58) Field of Classification Search ............ 548/263.8; 514/384
See application file for complete search history.

(56) References Cited

U.S. PATENT DOCUMENTS

| | | | |
|---|---|---|---|
| 4,537,899 A | 8/1985 | Horvath et al. | 514/384 |
| 4,670,448 A | 6/1987 | Clitherow et al. | 514/334 |
| 5,760,246 A | 6/1998 | Biller et al. | 548/309.7 |
| 5,883,110 A | 3/1999 | Tang et al. | 514/342 |
| 2004/0004116 A1 | 1/2004 | Hatanaka et al. | |
| 2004/0116490 A1 | 6/2004 | Marino, Jr. et al. | |
| 2004/0116495 A1 | 6/2004 | Marino, Jr. et al. | |
| 2005/0143578 A1 | 6/2005 | Kallander et al. | |
| 2005/0222212 A1 | 10/2005 | Marino et al. | |
| 2006/0247280 A1 | 11/2006 | Marino, Jr. et al. | |

FOREIGN PATENT DOCUMENTS

| | | |
|---|---|---|
| DE | 4142366 | 6/1993 |
| DE | 4424787 | 1/1996 |
| DE | 4425144 | 1/1996 |
| DE | 19922443 | 11/2000 |
| WO | WO93/20066 | 10/1993 |
| WO | WO98/56372 | 12/1998 |
| WO | WO 00/67734 | 11/2000 |
| WO | WO 01/36404 A1 | 5/2001 |
| WO | WO 01/53274 | 7/2001 |
| WO | WO 01/53331 | 7/2001 |
| WO | WO 01/78723 | 10/2001 |
| WO | WO 02/05804 A1 | 1/2002 |
| WO | WO 02/081415 A2 | 10/2002 |
| WO | WO 03/051906 A2 | 6/2003 |

OTHER PUBLICATIONS

Son et al. Bioorganic & Medicinal Chemistry (2002), vol. 10, No. 1, pp. 185-188.*
Lala et al. Cancer and Metastasis Reviews (1998), vol. 17, No. 1, pp. 91-106.*
Fromm et al., Splitting of Disulfides. Synthesis of Triazoles, (1924), 812757; Journal; JLACBF; Justus Liebigs Ann. Chem.; 437, pp. 106-124 (original with translation).
Patent Abstracts of Japan, 013(423) (C-638) Sep. 20, 1989 & JP 01 160972 (Tsumura & Co.), Jun. 23, 1989.
Azev et al., "Transformation of Azido Derivatives of S-Triazine into 1,2,4-Triazolylaminotetrazoles", *Mendeleev Communications*, 2: 49-50 (1993).
Trinka et al., "The Arylation of 5-Amino-3-Methylthio-1H-1,2,4-Triazole with Activated Aryl Chlorides", *Journal of Heterocyclic Chemistry*, 32(4): 1359-1371 (1995).
Tolstyakov et al., "Synthesis of Novel Derivatives of 3(5)-Alkylsulfonyl-1,2,4-Trizoles". *Russian Journal of General Chemistry, Consultants Bureau, US*, 70(9): 1458-1465 (2000).
Son et al. Bioorganic & Medicinal Chemistry (2002), vol. 10(1), pp. 185-188.
Lala et al. Cancer and Metastasis Reviews (1998), vol. 17(1), pp. 91-106.
Selvakumar et al., "High Expression of Methionine Aminopeptidase 2 in Human Colorectal Adenocarcinomas", *Clinical Cancer Res.*, 10: 2771-2775 (2004).
Wang et al., "Tumor Suppression by a Rationally Designed Reversible Inhibitor of Methionine Aminopeptidase-2". *Cancer Res.*, 63: 7861-7869 (2003).
Kallander et al. *J. Med. Chem.*, 48: 5644-5647 (2005).
Yang et al. *Biochemistry*, 40: 10645-10654 (2001).

* cited by examiner

*Primary Examiner*—Rebecca Anderson
(74) *Attorney, Agent, or Firm*—Kathryn L. Sieburth; Mary E. McCarthy; Charles M. Kinzig

(57) ABSTRACT

Compounds of this invention are non-peptide, reversible inhibitors of type 2 methionine aminopeptidase, useful in treating conditions mediated by angiogenesis, such as cancer, haemangioma, proliferative retinopathy, rheumatoid arthritis, atherosclerotic neovascularization, psoriasis, ocular neovascularization and obesity.

9 Claims, No Drawings

1,2,4-TRIAZOLE DERIVATIVES, COMPOSITIONS, PROCESS OF MAKING AND METHODS OF USE

This application is a continuation of application Ser. No. 10/089,433, filed Mar. 29, 2002 now abandoned, which is a 371 of International Application No. PCT/US00/26951, filed Sep. 29, 2000 which claims benefit of 60/157,286 filed Oct. 1, 1999.

FIELD OF THE INVENTION

Compounds of this invention are non-peptide, reversible inhibitors of type 2 methionine aminopeptidase, useful in treating conditions mediated by angiogenesis, such as cancer, haemangioma, proliferative retinopathy, rheumatoid arthritis, atherosclerotic neovascularization, psoriasis, ocular neovascularization and obesity.

BACKGROUND OF THE INVENTION

In 1974, Folkman proposed that for tumors to grow beyond a critical size and to spread to form metastases, they must recruit endothelial cells from the surrounding stroma to form their own endogenous microcirculation in a process termed angiogenesis (Folkman J. (1974) *Adv Cancer Res.* 19; 331). The new blood vessels induced by tumor cells as their life-line of oxygen and nutrients also provide exits for cancer cells to spread to other parts of the body. Inhibition of this process has been shown to effectively stop the proliferation and metastasis of solid tumors. A drug that specifically inhibits this process is known as an angiogenesis inhibitor.

Having emerged as a promising new strategy for the treatment of cancer, the anti-angiogenesis therapy ("indirect attack") has several advantages over the "direct attack" strategies. All the "direct attack" approaches such as using DNA damaging drugs, antimetabolites, attacking the RAS pathway, restoring p53, activating death programs, using aggressive T-cells, injecting monoclonal antibodies and inhibiting telomerase, etc., inevitably result in the selection of resistant tumor cells. Targeting the endothelial compartment of tumors as in the "indirect attack", however, should avoid the resistance problem because endothelial cells do not exhibit the same degree of genomic instability as tumor cells. Moreover, anti-angiogenic therapy generally has low toxicity due to the fact that normal endothelial cells are relatively quiescent in the body and exhibit an extremely long turnover. Finally since the "indirect attack" and "direct attack" target different cell types, there is a great potential for a more effective combination therapy.

More than 300 angiogenesis inhibitors have been discovered, of which about 31 agents are currently being tested in human trials in treatment of cancers (Thompson, et al., (1999) *J Pathol* 187, 503). TNP-470, a semisynthetic derivative of fumagillin of *Aspergillus fuigatus*, is among the most potent inhibitors of angiogenesis. It acts by directly inhibiting endothelial cell growth and migration in vitro and in vivo (Ingber et al. (1990) *Nature* 348, 555). Fumagillin and TNP-470, have been shown to inhibit type 2 methionine aminopeptidase (hereinafter MetAP2) by irreversibly modifying its active site. The biochemical activity of fumagillin analogs has been shown to correlate to their inhibitory effect on the proliferation of human umbillical vein endothelial cells (HUVEC). Although the mechanism of the selective action of fumagillin and related compounds on MetAP2-mediated endothelial cell cytostatic effect has not yet been established, possible roles of MetAP2 in cell proliferation have been suggested.

First, hMetAP-2-catalyzed cleavage of the initiator methionine of proteins could be essential for releasing many proteins that, after myristoylation, function as important signaling cellular factors involved in cell proliferation. Proteins known to be myristoylated include the src family tyrosine kinases, the small GTPase ARF, the HIV protein nef and the α subunit of heterotrimeric G proteins. A recently published study has shown that the myristoylation of nitric oxide synthase, a membrane protein involved in cell apoptosis, was blocked by fumagillin (Yoshida, et al. (1998) *Cancer Res.* 58(16), 3751). This is proposed to be an indirect outcome of inhibition of MetAP2-catalyzed release of the glycine-terminal myristoylation substrate. Alternatively, MetAP enzymes are known to be important to the stability of proteins in vivo according to the "N-end rule" which suggests increased stability of methionine-cleaved proteins relative to their N-terminal methionine precursors (Varshavsky, A (1996) *Proc. Natl. Acad. Sci. U.S.A.* 93, 12142). Inhibition of hMetAP2 could result in abnormal presence or absence of some cellular proteins critical to the cell cycle.

Methionine aminopeptidases (MetAP) are ubiquitously distributed in all living organisms. They catalyze the removal of the initiator methionine from newly translated polypeptides using divalent metal ions as cofactors. Two distantly related MetAP enzymes, type 1 and type 2, are found in eukaryotes, which at least in yeast, are both required for normal growth; whereas only one single MetAP is found in eubacteria (type 1) and archaebacteria (type 2). The N-terminal extension region distinguishes the methionine aminopeptidases in eukaryotes from those in procaryotes. A 64-amino acid sequence insertion (from residues 381 to 444 in hMetAP2) in the catalytic C-terminal domain distinguishes the MetAP-2 family from the MetAP-1 family. Despite the difference in the gene structure, all MetAP enzymes appear to share a highly conserved catalytic scaffold termed "pita-bread" fold (Bazan, et al. (1994) *Proc. Natl. Acad. Sci. U.S.A.* 91, 2473), which contains six strictly conserved residues implicated in the coordination of the metal cofactors.

Mammalian type 2 methionine aminopeptidase has been identified as a bifunctional protein implicated by its ability to catalyze the cleavage of N-terminal methionine from nascent polypeptides (Bradshaw, et al (1998) *Trends Biochem. Sci.* 23, 263) and to associate with eukaryotic initiation factor 2α (eIF-2α) to prevent its phosphorylation (Ray, et al. (1992) *Proc. Natl. Acad. Sci. U.S.A.* 89, 539). Both the genes of human and rat MetAP2 were cloned and have shown 92% sequence identity (Wu,. et al. (1993) *J. Biol. Chem.* 268, 10796; Li, X. & Chang, Y.-H. (1996) *Biochem. & Biophys. Res. Comm.* 227, 152). The N-terminal extension in these enzymes is highly charged and consists of two basic polylysine blocks and one aspartic acid block, which has been speculated to be involved in the binding of eIF-2α (Gupta, et al. (1993) in *Translational Regulation of Gene Expression* 2 (Ilan, J., Ed.), pp. 405-431, Plenum Press, New York).

The anti-angiogenic compounds, fumagillin and its analogs, have been shown to specifically block the exo-aminopeptidase activity of hMetAP2 without interfering with the formation of the hMetAP2: eIF2α complex (Griffith, et al., (1997) *Chem. Biol.* 4, 461; Sin, et al. (1997) *Proc. Natl. Acad. Sci. U.S.A.* 94, 6099). Fumagillin and its analogs inactivate the enzymatic activity of hMetAP2 with a high specificity, which is underscored by the lack of effect of these compounds on the closely related type 1 methionine aminopeptidase (MetAP1) both in vitro and in vivo in yeast (Griffith, et al., (1997) *Chem. Biol.* 4, 461; Sin, et al. (1997) *Proc. Natl. Acad Sci. USA*. 94, 6099). The extremely high potency (IC50<1 nM) of these inhibitors appears to be due to the irreversible modification of the active site residue, His231, of hMetAP2 (Liu, et al. (1998) *Science* 282, 1324). Disturbance of MetAP2 activity in vivo impairs the normal growth of yeast (Griffith, et al., (1997) *Chem. Biol.* 4, 461; Sin, et al. (1997) *Proc. Natl. Acad. Sci. U.S.A.* 94, 6099; In-house data) as well as Drosophila (Cutforth & Gaul (1999) *Mech. Dev.* 82, 23). Most significantly, there appears to be a clear correlation between the inhibition effect of flimagillin related compounds against the enzymatic activity of hMetAP2 in vitro and the suppression effect of these compounds against tumor-induced angiogenesis in vivo (Griffith, et al., (1997) *Chem. Biol.* 4, 461).

Cancer is the second leading cause of death in the U.S., exceeded only by heart disease. Despite recent successes in therapy against some forms of neoplastic disease, other forms continue to be refractory to treatment. Thus, cancer remains a leading cause of death and morbidity in the United States and elsewhere (Bailar and Gornik (1997) *N Engl J Med* 336, 1569). Inhibition of hMetAP2 provides a promising mechanism for the development of novel anti-angiogenic agents in the treatment of cancers. It has now been discovered that compounds of formulae (I) and (IA) are effective inhibitors of hMetAP2, and thus would be useful in treating conditions mediated by hMetAP2.

SUMMARY OF THE INVENTION

In one aspect, the present invention is to a compound of formula (I), or a pharmaceutically active salt or solvate thereof, and its use in treating conditions mediated by angiogenesis, such as cancer, haemangioma, proliferative retinopathy, rheumatoid arthritis, atherosclerotic neovascularization, psoriasis, ocular neovascularization and obesity:

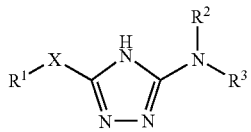

Formula (I)

wherein:
X is S or O;
$R^1$ is optionally substituted $C_{2-6}$alkyl, $C_{3-6}$alkenyl, $C_{3-6}$alkynyl, optionally substituted Ar—$C_{0-6}$alkyl, optionally substituted Het-$C_{0-6}$alkyl, or $C_{3-7}$cycloalkyl-$C_{0-6}$alkyl;
$R^2$ is optionally substituted $C_{2-6}$alkyl, $C_{3-6}$alkenyl, $C_{3-6}$alkynyl, optionally substituted Ar—$C_{0-6}$alkyl, optionally substituted Het-$C_{0-6}$alkyl, $C_{3-7}$cycloalkyl-$C_{0-6}$alkyl, provided that when $R^2$ is optionally substituted Het-$C_0$alkyl, and Het is indole, benzofuran, benzothiophene, benzisoxazole, benzothiozole or benzopyrazole, then the optional substituent is not —$(CH_2)_2NR^4R^5$; and
$R^3$ is H, optionally substituted $C_{1-6}$alkyl, $C_{3-6}$alkenyl, $C_{3-6}$alkynyl, optionally substituted Ar—$C_{0-6}$alkyl, optionally substituted Het-$C_{0-6}$alkyl, or $C_{3-7}$cycloalkyl-$C_{0-6}$alkyl, $C_{0-6}$alkyl-C(O)X'AB, $C_{0-6}$alkyl-S(O)$_2$X'AB, $C_{0-6}$alkyl-X'AB, wherein X' is O, S, C or N; A and B are independently H, optionally substituted $C_{1-6}$alkyl, $C_{3-6}$alkenyl, $C_{3-6}$alkynyl, optionally substituted Ar—$C_{0-6}$alkyl, optionally substituted Het-$C_{0-6}$alkyl, $C_{3-7}$cycloalkyl-$C_{0-6}$alkyl, or A or B are independently absent, provided that the compound is not 5-anilino-3-benzylthio-1,2,4-triazole, 3-(4-methyl-anilino)-5-benzylthio-1,2,4-triazole, 3-(2-methyl-anilino)-5-benzylthio-1,2,4-triazole, 3-(4-methoxy-anilino)-5-benzylthio-1,2,4-triazole, 3-(2-methoxy-anilino)-5-benzylthio-1,2,4-triazole, or 3-ethyl-3-anilino-5-benzylthio-1,2,4-triazole.

In a second aspect, the present invention is to a method of treating conditions mediated by angiogenesis, such as cancer, haemangioma, proliferative retinopathy, rheumatoid arthritis, atherosclerotic neovascularization, psoriasis, ocular neovascularization and obesity by administering a compound of formula (IA), or a pharmaceutically acceptable salt or solvate thereof

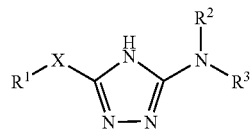

Formula (IA)

wherein,
X is S or O;
$R^1$ is optionally substituted $C_{1-6}$alkyl, $C_{3-6}$alkenyl, $C_{3-6}$alkynyl, optionally substituted Ar—$C_{0-6}$alkyl, optionally substituted Het-$C_{0-6}$alkyl, or $C_{3-7}$cycloalkyl-$C_{0-6}$alkyl;
$R^2$ is optionally substituted $C_{2-6}$alkyl, $C_{3-6}$alkenyl, $C_{3-6}$alkynyl, optionally substituted Ar—$C_{0-6}$alkyl, optionally substituted Het-$C_{0-6}$alkyl, $C_{3-7}$cycloalkyl-$C_{0-6}$alkyl;
$R^3$ is H, optionally substituted $C_{1-6}$alkyl, $C_{3-6}$alkenyl, $C_{3-6}$alkynyl, optionally substituted Ar—$C_{0-6}$alkyl, optionally substituted Het-$C_{0-6}$alkyl, or $C_{3-7}$cycloalkyl-$C_{0-6}$alkyl, $C_{0-6}$alkyl-C(O)X'AB, $C_{0-6}$alkyl-S(O)$_2$X'AB, $C_{0-6}$alkyl-X'AB, wherein X' is O, S, C or N; A and B are independently H, optionally substituted $C_{1-6}$alkyl, $C_{3-6}$alkenyl, $C_{3-6}$alkynyl, optionally substituted Ar—$C_{0-6}$alkyl, optionally substituted Het-$C_{0-6}$alkyl, $C_{3-7}$cycloalkyl-$C_{0-6}$alkyl, or A or B are independently absent.

In another aspect, the present invention is to a method of inhibiting MetAP2 in the treatment of angiogenesis-mediated diseases, all in mammals, preferably humans, comprising administering to such mammal in need thereof, a compound of formula (IA), or a pharmaceutically active salt or solvate thereof.

In yet another aspect, the present invention is to pharmaceutical compositions comprising a compound of formula (I) and a pharmaceutically acceptable carrier thereof. In particular, the pharmaceutical compositions of the present invention are used for treating MetAP2-mediated diseases.

DETAILED DESCRIPTION OF THE INVENTION

It has now been discovered that substituted 1,2,4-triazoles of formulae (I) and (IA) are inhibitors of MetAP2. It has also now been discovered that selective inhibition of MetAP2 enzyme mechanisms by treatment with the inhibitors of formula (IA), or a pharmaceutically acceptable salt or solvate thereof, represents a novel therapeutic and preventative approach to the treatment of a variety of disease states, including, but not limited to, cancer, haemangioma, proliferative retinopathy, rheumatoid arthritis, atherosclerotic neovascularization, psoriasis, ocular neovascularization and obesity.

The term "$C_{1-6}$alkyl" as used herein at all occurrences means a substituted and unsubstituted, straight or branched chain radical of 1 to 6 carbon atoms, unless the chain length is limited thereto, including, but not limited to methyl, ethyl, n-propyl, isopropyl, n-butyl, isobutyl and t-butyl, pentyl, n-pentyl, isopentyl, neopentyl and hexyl and the simple aliphatic isomers thereof. Any $C_{1-6}$alkyl group may be optionally substituted independently by one or more of $OR^4$, $R^4$, $NR^4R^5$. $C_0$alkyl means that no alkyl group is present in the moiety. Thus, Ar—$C_0$alkyl is equivalent to Ar.

As used herein at all occurrences, substituents $R^4$, $R^5$, and $R^6$ are independently defined as $C_{2-6}$alkyl, $C_{3-6}$alkenyl, $C_{3-6}$alkynyl, Ar—$C_{0-6}$alkyl, Het-$C_{0-6}$alkyl, or $C_{3-7}$cycloalkyl-$C_{0-6}$alkyl.

The term "$C_{3-7}$cycloalkyl" as used herein at all occurrences means substituted or unsubstituted cyclic radicals having 3 to 7 carbons, including but not limited to cyclopropyl, cyclopentyl, cyclohexyl and cycloheptyl radicals.

The term "$C_{3-6}$alkenyl" as used herein at all occurrences means an alkyl group of 3 to 6 carbons wherein a carbon-carbon single bond is replaced by a carbon-carbon double bond. $C_{3-6}$alkenyl includes 1-propene, 2-propene, 1-butene, 2-butene, isobutene and the several isomeric pentenes and hexenes. Both cis and trans isomers are included within the scope of this invention. Any $C_{3-6}$alkenyl group may be optionally substituted independently by one or more of Ph-$C_{0-6}$alkyl, Het'-$C_{0-6}$ alkyl, $C_{1-6}$alkyl, $C_{1-6}$alkoxy, $C_{1-6}$mercaptyl, Ph-$C_{0-6}$alkoxy, Het'-$C_{0-6}$alkoxy, OH, $NR^4R^5$, Het'-S—$C_{0-6}$alkyl, $(CH_2)_{1-6}OH$, $O(CH_2)_{1-6}NR^4R^5$, $(CH_2)_{0-6}CO_2R^6$, $O(CH_2)_{1-6}CO_2R^6$, $(CH_2)_{1-6}SO_2$, $CF_3$, $OCF_3$ or halogen.

The term "$C_{3-6}$alkynyl" as used herein at all occurrences means an alkyl group of 3 to 6 carbons wherein one carbon-carbon single bond is replaced by a carbon-carbon triple bond. $C_{3-6}$ alkynyl includes 1-propyne, 2-propyne, 1-butyne, 2-butyne, 3-butyne and the simple isomers of pentyne and hexyne.

The terms "Ar" or "aryl" as used herein interchangeably at all occurrences mean phenyl and naphthyl, optionally substituted by one or more of Ph-$C_{0-6}$alkyl, Het'-$C_{0-6}$ alkyl, $C_{1-6}$alkyl, $C_{1-6}$alkoxy, $C_{1-6}$mercaptyl, Ph-$C_{0-6}$alkoxy, Het'-$C_{0-6}$alkoxy, OH, $NR^4R^5$, Het'-S—$C_{0-6}$alkyl, $(CH_2)_{1-6}OH$, $(CH_2)_{1-6}NR^4R^5$, $O(CH_2)_{1-6}NR^4R^5$, $(CH_2)_{0-6}CO_2R^6$, $O(CH_2)_{1-6}CO_2R^6$, $(CH_2)_{1-6}SO_2$, $CF_3$, $OCF_3$ or halogen; in addition, Ph may be optionally substituted with one or more of $C_{1-6}$alkyl, $C_{1-6}$alkoxy, OH, $(CH_2)_{1-6}NR^4R^5$, $O(CH_2)_{1-6}NR^4R^5$, $CO_2R^6$, $CF_3$, or halogen; Het' is defined as for Het, and may be optionally substituted by one or more of $C_{1-6}$alkyl, $C_{1-6}$alkoxy, OH, $(CH_2)_{1-6}NR^4R^5$, $O(CH_2)_{16}NR^4R^5$, $CO_2R^6$, $CF_3$, or halogen; or two $C_{1-6}$alkyl or $C_{1-6}$alkoxy groups may be combined to form a 5-7 membered, saturated or unsaturated ring, fused onto the Ar ring.

Suitably, for compounds of formula (I), when Ar is substituted by Ph or Het', then Ph or Het' are substituted with one or more of $C_{2-6}$alkyl, $C_{1-6}$alkoxy, $(CH_2)_{1-6}NR^4R^5$, $O(CH_2)_{1-6}NR^4R^5$, $CO_2R^6$, $CF_3$ or halogen.

The terms "Het" or "heterocyclic" as used herein interchangeably at all occurrences, mean a stable 5- to 7-membered monocyclic, a stable 7- to 10-membered bicyclic, or a stable 11- to 18-membered tricyclic heterocyclic ring, all of which are either saturated or unsaturated, and consist of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure.

It will be understood that Het may be optionally substituted with one or more of Ph-$C_{0-6}$alkyl, Het'-$C_{0-6}$ alkyl, $C_{1-6}$alkyl, $C_{1-6}$alkoxy, $C_{1-6}$mercaptyl, Ph-$C_{0-6}$alkoxy, Het'-$C_{0-6}$alkoxy, OH, $NR^4R^5$, Het'-S—$C_{0-6}$alkyl, $(CH_2)_{1-6}OH$, $(CH_2)_{1-6}NR^4R^5$, $O(CH_2)_{1-6}NR^4R^5$, $(CH_2)_{0-6}CO_2R^6$, $O(CH_2)_{1-6}CO_2R^6$, $(CH_2)_{1-6}SO_2$, $CF_3$, $OCF_3$, CN, or halogen; Ph may be optionally substituted with one or more of $C_{1-6}$alkyl, $C_{1-6}$alkoxy, OH, $(CH_2)_{1-6}NR^4R^5$, $O(CH_2)_{1-6}NR^4R^5$, $CO_2R^6$, $CF_3$, or halogen; and two $C_{1-6}$alkyl or $C_{1-6}$alkoxy groups may be combined to form a 5-7 membered ring, saturated or unsaturated, fused onto the Het ring. Preferred optional substituents on Het are $C_{1-6}$alkyl, $C_{1-6}$alkoxy, $C_{1-6}$mercaptyl, halogen, $CF_3$, $OCF_3$, CN, or $NR^4R^5$.

Het' is defined as for Het and may be optionally substituted by one or more of $C_{1-6}$alkyl, $C_{1-6}$alkoxy, OH, $(CH_2)_{1-6}NR^4R^5$, $O(CH_2)_{1-6}NR^4R^5$, $CO_2R^6$, $CF_3$, or halogen.

Examples of such heterocycles include, but are not limited to piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, pyridinyl, pyrazinyl, oxazolidinyl, oxazolinyl, oxazolyl, isoxazolyl, morpholinyl, thiazolidinyl, thiazolinyl, thiazolyl, quinuclidinyl, indolyl, quinolinyl, isoquinolinyl, benzimidazolyl, benzopyranyl, benzoxazolyl, furyl, pyranyl, tetrahydrofuryl, tetrahydropyranyl, thienyl, benzoxazolyl, benzofuranyl, benzothiophenyl, thiamorpholinyl sulfoxide, thiamorpholinyl sulfone, and oxadiazolyl, as well as triazolyl, thiadiazolyl, oxadiazolyl, isoxazolyl, isothiazolyl, imidazolyl, pyridazinyl, pyrimidinyl and triazinyl which are available by routine chemical synthesis and are stable.

Compounds of this invention of formula (I), do not include compounds wherein $R^2$ is optionally substituted Het-$C_0$alkyl, and Het is indole, benzofuran, benzothiophene, benzisoxazole, benzothiozole or benzopyrazole, and the optional substituent is —$(CH_2)_2NR^4R^5$. The following compounds of this invention are known: 3-(4-methyl-anilino)-5-benzylthio-1,2,4-triazole, 3-(2-methyl-anilino)-5-benzylthio-1,2,4-triazole, 3-(4-methoxy-anilino)-5-benzylthio-1,2,4-triazole, 3-(2-methoxy-anilino)-5-benzylthio-1,2,4-triazole, or 3-ethyl-3-anilino-5-benzylthio-1,2,4-triazole. Fromm et al., *Justus Liebigs Ann. Chem.*, 437 1924, 113. A compound of formula (I) wherein $R^1$ is benzyl, $R^2$ is phenyl and $R^3$ is hydrogen is known.

Suitably, when moieties $R^1$, $R^2$, or $R^3$ are either optionally substituted Ar—$C_{0-6}$alkyl or optionally substituted Het-$C_{0-6}$alkyl, the moiety may be attached to the triazole substituent through the aromatic ring or through the alkyl chain.

Further, it will be understood that when a moiety is "optionally substituted" the moiety may have one or more optional substituents, each optional substituent being independently selected.

The terms "hetero" or "heteroatom" as used herein interchangeably at all occurrences mean oxygen, nitrogen and sulfur.

The terms "halo" or "halogen" as used herein interchangeably at all occurrences mean F, Cl, Br, and I.

Here and throughout this application the term $C_0$ denotes the absence of the substituent group immediately following; for instance, in the moiety Ar$C_{0-6}$alkyl, when C is 0, the substituent is Ar, e.g., phenyl. Conversely, when the moiety Ar$C_{0-6}$alkyl is identified as a specific aromatic group, e.g., phenyl, it is understood that C is 0.

Suitably X is sulfur or oxygen. Preferably X is sulfur.

Suitably, $R^1$ is optionally substituted $C_{2-6}$alkyl, $C_{3-6}$alkenyl, $C_{3-6}$alkynyl, optionally substituted Ar—$C_{0-6}$alkyl, optionally substituted Het-$C_{0-6}$alkyl, or $C_{3-7}$cycloalkyl-$C_{0-6}$alkyl. Preferably $R^1$ is optionally substituted Ar—$C_{0-6}$alkyl or optionally substituted Het-$C_{0-6}$alkyl. More preferably $R^1$ is optionally substituted Ar—$C_1$alkyl or optionally substituted Het-$C_1$alkyl. Most preferably $R^1$ is optionally substituted benzyl, optionally substituted methylfuran or optionally substituted methylthiophene. Preferably, when $R^1$ is Het-$C_1$alkyl, the alkyl chain is directly attached to moiety X.

Suitably, $R^2$ is optionally substituted $C_{1-6}$alkyl, $C_{3-6}$alkenyl, $C_{3-6}$alkynyl, optionally substituted Ar—$C_{0-6}$alkyl, optionally substituted Het-$C_{0-6}$alkyl, $C_{3-7}$cycloalkyl-$C_{0-6}$alkyl. Preferably, $R^2$ is optionally substituted Ar—$C_{0-6}$alkyl. More preferably $R^2$ is optionally substituted Ar—$C_0$alkyl. Most preferably $R^2$ is optionally substituted Ar—$C_0$alkyl, wherein the optional substituent is ortho $C_{1-6}$alkyl, preferably branched $C_{1-6}$alkyl, most preferably isopropyl.

Suitably, $R^3$ is H, optionally substituted $C_{1-6}$alkyl, $C_{3-6}$alkenyl, $C_{3-6}$alkynyl, optionally substituted Ar—$C_{0-6}$alkyl, optionally substituted Het-$C_{0-6}$alkyl, or $C_{3-7}$cycloalkyl-$C_{0-6}$alkyl, $C_{0-6}$alkyl-C(O)X'AB, $C_{0-6}$alkyl-S(O)$_2$X'AB, $C_{0-6}$alkyl-X'AB, wherein X' is O, S, C or N; A and B are independently H, optionally substituted $C_{1-6}$alkyl, $C_{3-6}$alkenyl, $C_{3-6}$alkynyl, optionally substituted Ar—$C_{0-6}$alkyl, optionally substituted Het-$C_{0-6}$alkyl, $C_{3-7}$cycloalkyl-$C_{0-6}$alkyl, or A or B are independently absent. Preferably $R^3$ is hydrogen or $C_{0-6}$alkyl-C(O)X'AB. More preferably $R^3$ is hydrogen or $C_{0-6}$alkyl-C(O)X'AB, wherein X' is oxygen and A is methyl or hydrogen and B is absent.

A preferred compound of this invention is a compound of formula (IB):

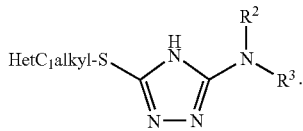

Formula (IB)

Suitably, pharmaceutically acceptable salts of formula (I) include, but are not limited to, salts with inorganic acids such as hydrochloride, sulfate, phosphate, diphosphate, hydrobromide, and nitrate, or salts with an organic acid such as malate, maleate, fumarate, tartrate, succinate, citrate, acetate, lactate, methanesulfonate, p-toluenesulfonate, palmitate, salicylate, and stearate.

The compounds of the present invention may contain one or more asymmetric carbon atoms and may exist in racemic and optically active forms. The stereocenters may be (R), (S) or any combination of R and S configuration, for example, (R,R), (R,S), (S,S) or (S,R). All of these compounds are within the scope of the present invention.

All compounds of formula (IA) specifically named herein are considered to be part of the invention disclosed herein. Among the compounds of the invention of formula (IA) are the following compounds:

3-anilino-5-benzylthio-1,2,4-triazole;

3-anilino-5-methylthio-1,2,4-triazole;

3-anilino-5-(4-chloro-benzylthio)-1,2,4-triazole;

3-anilino-5-allylthio-1,2,4-triazole;

3-anilino-5-(2-methyl-2-butenylthio)-1,2,4-triazole;

3-anilino-5-(2-methyl-butylthio)-1,2,4-triazole;

3-anilino-5-(2-methyl-2-pentenylthio)-1,2,4-triazole;

3-anilino-5-(α-methylbenzylthio)-1,2,4-triazole;

3-anilino-5-(cyclohexylmethylthio)-1,2,4-triazole;

3-anilino-5-(propyl acetylthio)-1,2,4-triazole;

3-anilino-5-(3,3-dimethoxy-propylthio)-1,2,4-triazole;

3-anilino-5-(2-phenethylthio)-1,2,4-triazole;

3-anilino-5-(5-methyl-isoxazol-3-ylmethylthio)-1,2,4-triazole;

3-anilino-5-(3-phenyl-[1,2,4]oxadiazol-5-ylmethylthio)-1,2,4-triazole;

3-anilino-5-(1H-benzoimidazol-2-ylmethylthio)-1,2,4-triazole;

3-anilino-5-(2-(4-chlorophenyl)-thiazol-4-ylmethylthio)-1,2,4-triazole;

3-anilino-5-(2-methyl-thiazol-4-ylmethylthio)-1,2,4-triazole;

3-anilino-5-(pyridin-2-ylmethylthio)-1,2,4-triazole;

3-anilino-5-(4-i-propyl-benzylthio)-1,2,4-triazole;

3-anilino-5-(pyridin-4-ylmethylthio)-1,2,4-triazole;

3-anilino-5-(quinolin-8-ylthio)-1,2,4-triazole;

3-anilino-5-(4-acetamido-benzylthio)-1,2,4-triazole;

4-(5-anilino-2H-[1,2,4]triazol-3-yl thio)-benzoic acid;

3-anilino-5-(2-methyl-benzylthio)-1,2,4-triazole;

3-anilino-5-(4-trifluoromethyl-benzylthio)-1,2,4-triazole;

3-anilino-5-(3,4-difluoro-benzylthio)-1,2,4-triazole;

3-anilino-5-(3,5-dimethyl-benzylthio)-1,2,4-triazole;

3-anilino-5-(4-cyano-benzylthio)-1,2,4-triazole;

3-(4-methyl-anilino)-5-(cyclohexylmethylthio)-1,2,4-triazole;

3-(4-methyl-anilino)-5-(pyridin-4-ylmethylthio)-1,2,4-triazole;

3-(4-methyl-anilino)-5-(2-methyl-2-butenylthio)-1,2,4-triazole;

3-(4-methyl-anilino)-5-(2-fluoro-benzylthio)-1,2,4-triazole;

3-(4-methyl-anilino)-5-(5-methyl-isoxazol-3-ylmethylthio)-1,2,4-triazole;

3-(4-methyl-anilino)-5-(2-methyl-benzylthio)-1,2,4-triazole;

3-(4-methyl-anilino)-5-(3,4-difluoro-benzylthio)-1,2,4-triazole;

3-(4-methyl-anilino)-5-(2-methoxy-benzylthio)-1,2,4-triazole;

3-(4-methyl-anilino)-5-(2-methyl-thiazol-4-ylmethylthio)-1,2,4-triazole;

3-(4-methyl-anilino)-5-(pyridin-2-ylmethylthio)-1,2,4-triazole;

3-(4-methyl-anilino)-5-(3-methyl-thiophen-2-ylmethylthio)-1,2,4-triazole;

3-(4-methyl-anilino)-5-(3-chloro-thiophen-2-ylmethylthio)-1,2,4-triazole;

3-(2-methyl-anilino)-5-(cyclohexylmethylthio)-1,2,4-triazole;

3-(2-methyl-anilino)-5-(pyridin-4-ylmethylthio)-1,2,4-triazole;

3-(2-methyl-anilino)-5-(2-methyl-2-butenylthio)-1,2,4-triazole;

3-(2-methyl-anilino)-5-(2-fluoro-benzylthio)-1,2,4-triazole;

3-(2-methyl-anilino)-5-(5-methyl-isoxazol-3-ylmethylthio)-1,2,4-triazole;

3-(2-methyl-anilino)-5-(2-methyl-benzylthio)-1,2,4-triazole;

3-(2-methyl-anilino)-5-(3,4-difluoro-benzylthio)-1,2,4-triazole;

3-(2-methyl-anilino)-5-(2-methoxy-benzylthio)-1,2,4-triazole;

3-(2-methyl-anilino)-5-(2-methyl-thiazol-4-ylmethylthio)-1,2,4-triazole;

3-(2-methyl-anilino)-5-(pyridin-2-ylmethylthio)-1,2,4-triazole;

3-(4-chloro-anilino)-5-(cyclohexylmethylthio)-1,2,4-triazole;

3-(4-chloro-anilino)-5-(pyridin-4-ylmethylthio)-1,2,4-triazole;

3-(4-chloro-anilino)-5-(2-methyl-2-butenylthio)-1,2,4-triazole;

3-(4-chloro-anilino)-5-(2-fluoro-benzylthio)-1,2,4-triazole;

3-(4-chloro-anilino)-5-(5-methyl-isoxazol-3-ylmethylthio)-1,2,4-triazole;

3-(4-chloro-anilino)-5-(2-methyl-benzylthio)-1,2,4-triazole;

3-(4-chloro-anilino)-5-(3,4-difluoro-benzylthio)-1,2,4-triazole;

3-(4-chloro-anilino)-5-(2-methoxy-benzylthio)-1,2,4-triazole;

3-(4-chloro-anilino)-5-(2-methyl-thiazol-4-ylmethylthio)-1,2,4-triazole;

3-(4-chloro-anilino)-5-(pyridin-2-ylmethylthio)-1,2,4-triazole;

3-(4-methoxy-anilino)-5-(cyclohexylmethylthio)-1,2,4-triazole;

3-(4-methoxy-anilino)-5-(pyridin-4-ylmethylthio)-1,2,4-triazole;

3-(4-methoxy-anilino)-5-(2-methyl-2-butenylthio)-1,2,4-triazole;

3-(4-methoxy-anilino)-5-(2-fluoro-benzylthio)-1,2,4-triazole;

3-(4-methoxy-anilino)-5-(5-methyl-isoxazol-3-ylmethylthio)-1,2,4-triazole;

3-(4-methoxy-anilino)-5-(2-methyl-benzylthio)-1,2,4-triazole;

3-(4-methoxy-anilino)-5-(3,4-difluoro-benzylthio)-1,2,4-triazole;

3-(4-methoxy-anilino)-5-(2-methoxy-benzylthio)-1,2,4-triazole;

3-(4-methoxy-anilino)-5-(2-methyl-thiazol-4-ylmethylthio)-1,2,4-triazole;

3-(4-methoxy-anilino)-5-(pyridin-2-ylmethylthio)-1,2,4-triazole;

4-(5-(cyclohexylmethylthio)-1H-[1,2,4]triazol-3-ylamino)-benzoic acid methyl ester;

4-(5-(pyridin-4-ylmethylthio)-1H-[1,2,4]triazol-3-ylamino)-benzoic acid methyl ester;

4-(5-(2-methyl-2-butenylthio)-1H-[1,2,4]triazol-3-ylamino)-benzoic acid methyl ester;

4-(5-(2-fluoro-benzylthio)-1H-[1,2,4]triazol-3-ylamino)-benzoic acid methyl ester;

4-(5-(5-methyl-isoxazol-3-ylmethylthio)-1H-[1,2,4]triazol-3-ylamino)-benzoic acid methyl ester;

4-(5-(3-methoxy-benzylthio)-1H-[1,2,4]triazol-3-ylamino)-benzoic acid methyl ester;

4-(5-(2-methyl-benzylthio)-1H-[1,2,4]triazol-3-ylamino)-benzoic acid methyl ester;

4-(5-(3,4-difluoro-benzylthio)-1H-[1,2,4]triazol-3-ylamino)-benzoic acid methyl ester;

4-(5-(2-methoxy-benzylthio)-1H-[1,2,4]triazol-3-ylamino)-benzoic acid methyl ester;

4-(5-(2-methyl-thiazol-4-ylmethylthio)-1H-[1,2,4]triazol-3-ylamino)-benzoic acid methyl ester;

4-(5-(pyridin-2-ylmethylthio)-1H-[1,2,4]triazol-3-ylamino)-benzoic acid methyl ester;

3-(3,4-dimethoxy-anilino)-5-(thiophen-2-ylmethylthio)-1,2,4-triazole;

3-(3,4-dimethoxy-anilino)-5-(3-methoxy-benzylthio)-1,2,4-triazole;

3-(3,4-dimethoxy-anilino)-5-(cyclohexylmethylthio)-1,2,4-triazole;

3-(3,4-dimethoxy-anilino)-5-(pyridin-4-ylmethylthio)-1,2,4-triazole;

3-(3,4-dimethoxy-anilino)-5-(2-methyl-2-butenylthio)-1,2,4-triazole;

3-(3,4-dimethoxy-anilino)-5-(2-fluoro-benzylthio)-1,2,4-triazole;

3-(3,4-dimethoxy-anilino)-5-(5-methyl-isoxazol-3-ylmethylthio)-1,2,4-triazole;

3-(3,4-dimethoxy-anilino)-5-(2-methyl-benzylthio)-1,2,4-triazole;

3-(3,4-dimethoxy-anilino)-5-(3,4-difluoro-benzylthio)-1,2,4-triazole;

3-(3,4-dimethoxy-anilino)-5-(2-methoxy-benzylthio)-1,2,4-triazole;

3-(3,4-dimethoxy-anilino)-5-(2-methyl-thiazol-4-ylmethylthio)-1,2,4-triazole;

3-(3,4-dimethoxy-anilino)-5-(pyridin-2-ylmethylthio)-1,2,4-triazole;

3-(2-phenyl-anilino)-5-benzylthio-1,2,4-triazole;

3-(4-methoxy-anilino)-5-(2-methoxy-benzylthio)-1,2,4-triazole;

3-(2-phenyl-anilino)-5-(thiophen-2-ylmethylthio)-1,2,4-triazole;

3-(2-phenyl-anilino)-5-(3-methoxy-benzylthio)-1,2,4-triazole;

3-(2-phenyl-anilino)-5-(cyclohexylmethylthio)-1,2,4-triazole;

3-(2-phenyl-anilino)-5-(pyridin-4-ylmethylthio)-1,2,4-triazole;

3-(2-phenyl-anilino)-5-(2-methyl-2-butenylthio)-1,2,4-triazole;

3-(2-phenyl-anilino)-5-(2-fluoro-benzylthio)-1,2,4-triazole;

3-(2-phenyl-anilino)-5-(5-methyl-isoxazol-3-ylmethylthio)-1,2,4-triazole;

3-(2-phenyl-anilino)-5-(2-methyl-benzylthio)-1,2,4-triazole;

3-(2-phenyl-anilino)-5-(3,4-difluoro-benzylthio)-1,2,4-triazole;

3-(2-phenyl-anilino)-5-(2-methoxy-benzylthio)-1,2,4-triazole;

3-(2-phenyl-anilino)-5-(2-methyl-thiazol-4-ylmethylthio)-1,2,4-triazole;

[5-(benzylthio)-1H-[1,2,4]triazol-3-yl]-pyridin-3-yl-amine;

[5-(3-methoxybenzylthio)-1H-[1,2,4]triazol-3-yl]-pyridin-3-yl-amine;

[5-(cyclohexylmethylthio)-1H-[1,2,4]triazol-3-yl]-pyridin-3-yl-amine;

[5-(pyridin-4-ylmethylthio)-1H-[1,2,4]triazol-3-yl]-pyridin-3-yl-amine;

[5-(2-methyl-2-butenylthio)-1H-[1,2,4]triazol-3-yl]-pyridin-3-yl-amine;

[5-(2-fluoro-benzylthio)-1H-[1,2,4]triazol-3-yl]-pyridin-3-yl-amine;

[5-(5-methyl-isoxazol-3-ylmethylthio)-1H-[1,2,4]triazol-3-yl]-pyridin-3-yl-amine;

[5-(2-methyl-benzylthio)-1H-[1,2,4]triazol-3-yl]-pyridin-3-yl-amine;

[5-(3,4-difluoro-benzylthio)-1H-[1,2,4]triazol-3-yl]-pyridin-3-yl-amine;

[5-(2-methoxy-benzylthio)-1H-[1,2,4]triazol-3-yl]-pyridin-3-yl-amine;

[5-(pyridin-2-ylmethylthio)-1H-[1,2,4]triazol-3-yl]-pyridin-3-yl-amine;

[5-(2-methyl-thiazol-4-ylmethylthio)-1H-[1,2,4]triazol-3-yl]-pyridin-3-yl-amine;

[5-(thiophen-2-ylmethylthio)-1H-[1,2,4]triazol-3-yl]-pyridin-3-yl-amine;

3-(2-ethyl-anilino)-5-(4-fluoro-benzylthio)-1,2,4-triazole;

3-(2-ethyl-anilino)-5-(3,4-difluoro-benzylthio)-1,2,4-triazole;

3-(2-ethyl-anilino)-5-(2-methyl-2-butenylthio)-1,2,4-triazole;

3-(2-ethyl-anilino)-5-(2-fluoro-benzylthio)-1,2,4-triazole;

3-(2-ethyl-anilino)-5-(2-methyl-benzylthio)-1,2,4-triazole;

3-(2-ethyl-anilino)-5-(2-chloro-benzylthio)-1,2,4-triazole;

3-(2-ethyl-anilino)-5-(4-methoxy-benzylthio)-1,2,4-triazole;

3-(2-ethyl-anilino)-5-(3,4-methylenedioxy-benzylthio)-1,2,4-triazole;

3-(2-ethyl-anilino)-5-(5-methyl-isoxazol-3-ylmethylthio)-1,2,4-triazole;

3-(2-ethyl-anilino)-5-(pyridin-2-ylmethylthio)-1,2,4-triazole;

3-(2-ethyl-anilino)-5-(2-methoxy-benzylthio)-1,2,4-triazole;

3-(2-methoxy-anilino)-5-benzylthio-1,2,4-triazole;

3-(2-methoxy-anilino)-5-(4-fluoro-benzylthio)-1,2,4-triazole;

3-(2-methoxy-anilino)-5-(cyclohexylmethylthio)-1,2,4-triazole;

3-(2-methoxy-anilino)-5-(3,4-difluoro-benzylthio)-1,2,4-triazole;

3-(2-methoxy-anilino)-5-(2-methyl-2-butenylthio)-1,2,4-triazole;

3-(2-methoxy-anilino)-5-(2-fluoro-benzylthio)-1,2,4-triazole;

3-(2-methoxy-anilino)-5-(2-methyl-benzylthio)-1,2,4-triazole;

3-(2-methoxy-anilino)-5-(2-chloro-benzylthio)-1,2,4-triazole;

3-(2-methoxy-anilino)-5-(4-methoxy-benzylthio)-1,2,4-triazole;

3-(2-methoxy-anilino)-5-(3,4-methylenedioxy-benzylthio)-1,2,4-triazole;

3-(2-methoxy-anilino)-5-(5-methyl-isoxazol-3-ylmethylthio)-1,2,4-triazole;

3-(2-methoxy-anilino)-5-(pyridin-2-ylmethylthio)-1,2,4-triazole;

3-(2-methoxy-anilino)-5-(2-methoxy-benzylthio)-1,2,4-triazole;

3-(2-isopropyl-anilino)-5-benzylthio-1,2,4-triazole;

3-(2-isopropyl-anilino)-5-(4-fluoro-benzylthio)-1,2,4-triazole;

3-(2-isopropyl-anilino)-5-(cyclohexylmethylthio)-1,2,4-triazole;

3-(2-isopropyl-anilino)-5-(3,4-difluoro-benzylthio)-1,2,4-triazole;

3-(2-isopropyl-anilino)-5-(2-methyl-2-butenylthio)-1,2,4-triazole;

3-(2-isopropyl-anilino)-5-(2-fluoro-benzylthio)-1,2,4-triazole;

3-(2-isopropyl-anilino)-5-(2-methyl-benzylthio)-1,2,4-triazole;

3-(2-isopropyl-anilino)-5-(2-chloro-benzylthio)-1,2,4-triazole;

3-(2-isopropyl-anilino)-5-(4-methoxy-benzylthio)-1,2,4-triazole;

3-(2-isopropyl-anilino)-5-(3,4-methylenedioxy-benzylthio)-1,2,4-triazole;

3-(2-isopropyl-anilino)-5-(5-methyl-isoxazol-3-ylmethylthio)-1,2,4-triazole;

3-(2-isopropyl-anilino)-5-(pyridin-2-ylmethylthio)-1,2,4-triazole;

3-(2-isopropyl-anilino)-5-(2-methoxy-benzylthio)-1,2,4-triazole;

3-(3-methyl-anilino)-5-(4-fluoro-benzylthio)-1,2,4-triazole;

3-(3-methyl-anilino)-5-(cyclohexylmethylthio)-1,2,4-triazole;

3-(3-methyl-anilino)-5-(3,4-difluoro-benzylthio)-1,2,4-triazole;

3-(3-methyl-anilino)-5-(2-methyl-2-butenylthio)-1,2,4-triazole;

3-(3-methyl-anilino)-5-(2-fluoro-benzylthio)-1,2,4-triazole;

3-(3-methyl-anilino)-5-(2-methyl-benzylthio)-1,2,4-triazole;

3-(3-methyl-anilino)-5-(2-chloro-benzylthio)-1,2,4-triazole;

3-(3-methyl-anilino)-5-(4-methoxy-benzylthio)-1,2,4-triazole;

3-(3-methyl-anilino)-5-(3,4-methylenedioxy-benzylthio)-1,2,4-triazole;

3-(3-methyl-anilino)-5-(5-methyl-isoxazol-3-ylmethylthio)-1,2,4-triazole;

3-(3-methyl-anilino)-5-(pyridin-2-ylmethylthio)-1,2,4-triazole;

3-(3-methyl-anilino)-5-(2-methoxy-benzylthio)-1,2,4-triazole;

3-(4-n-butyl-anilino)-5-(4-fluoro-benzylthio)-1,2,4-triazole;

3-(4-n-butyl-anilino)-5-(3,4-difluoro-benzylthio)-1,2,4-triazole;

3-(4-n-butyl-anilino)-5-(2-methyl-2-butenylthio)-1,2,4-triazole;

3-(4-n-butyl-anilino)-5-(2-fluoro-benzylthio)-1,2,4-triazole;

3-(4-n-butyl-anilino)-5-(2-methyl-benzylthio)-1,2,4-triazole;

3-(4-n-butyl-anilino)-5-(2-chloro-benzylthio)-1,2,4-triazole;

3-(4-n-butyl-anilino)-5-(4-methoxy-benzylthio)-1,2,4-triazole;

3-(4-n-butyl-anilino)-5-(3,4-methylenedioxy-benzylthio)-1,2,4-triazole;

3-(4-n-butyl-anilino)-5-(5-methyl-isoxazol-3-ylmethylthio)-1,2,4-triazole;

3-(4-n-butyl-anilino)-5-(pyridin-2-ylmethylthio)-1,2,4-triazole;

3-(4-n-butyl-anilino)-5-(2-methoxy-benzylthio)-1,2,4-triazole;

3-(2,4-dimethoxy-anilino)-5-(4-fluoro-benzylthio)-1,2,4-triazole;

3-(2,4-dimethoxy-anilino)-5-(cyclohexylmethylthio)-1,2,4-triazole;

3-(2,4-dimethoxy-anilino)-5-(3,4-difluoro-benzylthio)-1,2,4-triazole;

3-(2,4-dimethoxy-anilino)-5-(2-methyl-2-butenylthio)-1,2,4-triazole;

3-(2,4-dimethoxy-anilino)-5-(2-fluoro-benzylthio)-1,2,4-triazole;

3-(2,4-dimethoxy-anilino)-5-(2-methyl-benzylthio)-1,2,4-triazole;

3-(2,4-dimethoxy-anilino)-5-(2-chloro-benzylthio)-1,2,4-triazole;

3-(2,4-dimethoxy-anilino)-5-(4-methoxy-benzylthio)-1,2,4-triazole;

3-(2,4-dimethoxy-anilino)-5-(3,4-methylenedioxy-benzylthio)-1,2,4-triazole;

3-(2,4-dimethoxy-anilino)-5-(5-methyl-isoxazol-3-ylmethylthio)-1,2,4-triazole;

3-(2,4-dimethoxy-anilino)-5-(pyridin-2-ylmethylthio)-1,2,4-triazole;

3-(2,4-dimethoxy-anilino)-5-(2-methoxy-benzylthio)-1,2,4-triazole;

3-(2-methyl-4-methoxy-anilino)-5-(4-fluoro-benzylthio)-1,2,4-triazole;

3-(2-methyl-4-methoxy-anilino)-5-(cyclohexylmethylthio)-1,2,4-triazole;

3-(2-methyl-4-methoxy-anilino)-5-(3,4-difluoro-benzylthio)-1,2,4-triazole;

3-(2-methyl-4-methoxy-anilino)-5-(2-methyl-2-butenylthio)-1,2,4-triazole;

3-(2-methyl-4-methoxy-anilino)-5-(2-fluoro-benzylthio)-1,2,4-triazole;

3-(2-methyl-4-methoxy-anilino)-5-(2-methyl-benzylthio)-1,2,4-triazole;

3-(2-methyl-4-methoxy-anilino)-5-(2-chloro-benzylthio)-1,2,4-triazole;

3-(2-methyl-4-methoxy-anilino)-5-(4-methoxy-benzylthio)-1,2,4-triazole;

3-(2-methyl-4-methoxy-anilino)-5-(3,4-methylenedioxy-benzylthio)-1,2,4-triazole;

3-(2-methyl-4-methoxy-anilino)-5-(5-methyl-isoxazol-3-ylmethylthio)-1,2,4-triazole;

3-(2-methyl-4-methoxy-anilino)-5-(pyridin-2-ylmethylthio)-1,2,4-triazole;

3-(2-methyl-4-methoxy-anilino)-5-(2-methoxy-benzylthio)-1,2,4-triazole;

3-(2,6-dimethyl-anilino)-5-(4-fluoro-benzylthio)-1,2,4-triazole;

3-(2,6-dimethyl-anilino)-5-(cyclohexylmethylthio)-1,2,4-triazole;

3-(2,6-dimethyl-anilino)-5-(3,4-difluoro-benzylthio)-1,2,4-triazole;

3-(2,6-dimethyl-anilino)-5-(2-methyl-2-butenylthio)-1,2,4-triazole;

3-(2,6-dimethyl-anilino)-5-(2-fluoro-benzylthio)-1,2,4-triazole;

3-(2,6-dimethyl-anilino)-5-(2-methyl-benzylthio)-1,2,4-triazole;

3-(2,6-dimethyl-anilino)-5-(2-chloro-benzylthio)-1,2,4-triazole;

3-methyl-3-anilino-5-benzylthio-1,2,4-triazole;

3-ethyl-3-anilino-5-benzylthio-1,2,4-triazole;

3-n-propyl-3-anilino-5-benzylthio-1,2,4-triazole;

3-n-butyl-3-anilino-5-benzylthio-1,2,4-triazole;

3-i-propyl-3-anilino-5-benzylthio-1,2,4-triazole;

3-allyl-3-anilino-5-benzylthio-1,2,4-triazole; and 3-benzyl-3-anilino-5-benzylthio-1,2,4-triazole.

Among the preferred compounds of formula (IA) of this invention are the following compounds:

3-anilino-5-benzylthio-1,2,4-triazole;

3-(4-methyl-anilino)-5-benzylthio-1,2,4-triazole;

3-(2-methyl-anilino)-5-benzylthio-1,2,4-triazole;

3-(4-methoxy-anilino)-5-benzylthio-1,2,4-triazole;

3-(2-methoxy-anilino)-5-benzylthio-1,2,4-triazole;

3-ethyl-3-anilino-5-benzylthio-1,2,4-triazole;

3-(4-chloro-anilino)-5-benzylthio-1,2,4-triazole;

3-(3,4-dimethoxy-anilino)-5-benzylthio-1,2,4-triazole;

3-(2-ethyl-anilino)-5-benzylthio-1,2,4-triazole;

3-(2-isopropyl-anilino)-5-benzylthio-1,2,4-triazole;

3-(3-methyl-anilino)-5-benzylthio-1,2,4-triazole;

3-(4-n-butyl-anilino)-5-benzylthio-1,2,4-triazole;

3-(2,4-dimethoxy-anilino)-5-benzylthio-1,2,4-triazole;

3-(2-methyl-4-methoxy-anilino)-5-benzylthio-1,2,4-triazole;

3-(2,6-dimethyl-anilino)-5-benzylthio-1,2,4-triazole;

3-methylacetate-3-(p-methyl)-anilino-5-benzylthio-1,2,4-triazole;

3-methylacetate-3-(p-methoxy)-anilino-5-benzylthio-1,2,4-triazole;

3-methylacetate-3-(2,6-dimethyl)-anilino-5-benzylthio-1,2,4-triazole;

3-anilino-5-(3-methyl-thiophen-2-ylmethylthio)-1,2,4-triazole;

3-anilino-5-(3-chloro-thiophen-2-ylmethylthio)-1,2,4-triazole;

5-(5-phenylamino-4H-[1,2,4]triazol-3-ylsulfanylmethyl)-furan-2-carboxylic acid ethyl ester;

5-(5-phenylamino-4H-[1,2,4]triazol-3-ylsulfanylmethyl)-furan-2-carbaldehyde;

3-(4-methyl-anilino)-5-(3-methyl-thiophen-2-ylmethylthio)-1,2,4-triazole;

3-(4-methyl-anilino)-5-(3-chloro-thiophen-2-ylmethylthio)-1,2,4-triazole;

3-(4-methyl-anilino)-5-(5-methyl-thiophen-2-ylmethylthio)-1,2,4-triazole;

3-(4-methyl-anilino)-5-(5-chloro-thiophen-2-ylmethylthio)-1,2,4-triazole;

5-(5-p-tolyl amino-4H-[1,2,4]triazol-3-ylsulfanylmethyl)-furan-2-carboxylic acid ethyl ester;

3-(4-methyl-anilino)-5-(5-bromo-thiophen-2-ylmethylthio)-1,2,4-triazole;

5-(5-p-tolyl amino-4H-[1,2,4]triazol-3-ylsulfanylmethyl)-furan-2-carbaldehyde;

3-(2-methyl-anilino)-5-(thiophen-2-ylmethylthio)-1,2,4-triazole;

3-(2-methyl-anilino)-5-(3-methyl-thiophen-2-ylmethylthio)-1,2,4-triazole;

3-(2-methyl-anilino)-5-(3-chloro-thiophen-2-ylmethylthio)-1,2,4-triazole;

3-(2-methyl-anilino)-5-(5-methyl-thiophen-2-ylmethylthio)-1,2,4-triazole;

3-(2-methyl-anilino)-5-(5-chloro-thiophen-2-ylmethylthio)-1,2,4-triazole;

5-(5-o-tolyl amino-4H-[1,2,4]triazol-3-ylsulfanylmethyl)-furan-2-carboxylic acid ethyl ester;

3-(2-methyl-anilino)-5-(5-bromo-thiophen-2-ylmethylthio)-1,2,4-triazole;

5-(5-o-tolyl amino-4H-[1,2,4]triazol-3-ylsulfanylmethyl)-furan-2-carbaldehyde;

3-(2-methyl-anilino)-5-(furan-3-ylmethylthio)-1,2,4-triazole;

3-(4-methoxy-anilino)-5-(thiophen-2-ylmethylthio)-1,2,4-triazole;

3-(4-methoxy-anilino)-5-(3-chloro-thiophen-2-ylmethylthio)-1,2,4-triazole;

3-(3,4-dimethoxy-anilino)-5-(thiophen-2-ylmethylthio)-1,2,4-triazole;

[5-(thiophen-2-ylmethylthio)-1H-[1,2,4]triazol-3-yl]-pyridin-3-yl-amine;

3-(2-ethyl-anilino)-5-(thiophen-2-ylmethylthio)-1,2,4-triazole;

3-(2-methoxy-anilino)-5-(thiophen-2-ylmethylthio)-1,2,4-triazole;

3-(2-methoxy-anilino)-5-(furan-2-ylmethylthio)-1,2,4-triazole;

5-(5-(2-methoxyphenylamino)-4H-[1,2,4]triazol-3-ylsulfanylmethyl)-furan-2-carboxylic acid ethyl ester 3-(2-methoxy-anilino)-5-(5-bromo-thiophen-2-ylmethylthio)-1,2,4-triazole;

3-(2-methoxy-anilino)-5-(thiophen-3-ylmethylthio)-1,2,4-triazole;

3-(2-methoxy-anilino)-5-(furan-3-ylmethylthio)-1,2,4-triazole;

3-(3-methyl-anilino)-5-(thiophen-2-ylmethylthio)-1,2,4-triazole;

3-(3-methyl-anilino)-5-(3-methyl-thiophen-2-ylmethylthio)-1,2,4-triazole;

3-(3-methyl-anilino)-5-(3-chloro-thiophen-2-ylmethylthio)-1,2,4-triazole;

3-(3-methyl-anilino)-5-(5-methyl-thiophen-2-ylmethylthio)-1,2,4-triazole;

3-(3-methyl-anilino)-5-(5-chloro-thiophen-2-ylmethylthio)-1,2,4-triazole;

5-(5-(3-methylphenylamino)-4H-[1,2,4]triazol-3-ylsulfanylmethyl)-furan-2-carboxylic acid ethyl ester;

3-(3-methyl-anilino)-5-(5-bromo-thiophen-2-ylmethylthio)-1,2,4-triazole;

5-(5-(3-methylphenylamino)-4H-[1,2,4]triazol-3-ylsulfanylmethyl)-furan-2-carbaldehyde;

3-(4-n-butyl-anilino)-5-(thiophen-2-ylmethylthio)-1,2,4-triazole;

3-(2,4-dimethoxy-anilino)-5-(thiophen-2-ylmethylthio)-1,2,4-triazole;

3-(2-methyl-4-methoxy-anilino)-5-(thiophen-2-ylmethylthio)-1,2,4-triazole;

3-(4-fluoro-anilino)-5-(furan-2-ylmethylthio)-1,2,4-triazole;

3-(4-fluoro-anilino)-5-(3-methyl-thiophen-2-ylmethylthio)-1,2,4-triazole;

3-(4-fluoro-anilino)-5-(3-chloro-thiophen-2-ylmethylthio)-1,2,4-triazole;

3-(4-fluoro-anilino)-5-(5-methyl-thiophen-2-ylmethylthio)-1,2,4-triazole;

3-(4-fluoro-anilino)-5-(5-chloro-thiophen-2-ylmethylthio)-1,2,4-triazole;

5-(5-(4-fluorophenylamino)-4H-[1,2,4]triazol-3-ylsulfanylmethyl)-furan-2-carboxylic acid ethyl ester;

3-(4-fluoro-anilino)-5-(5-bromo-thiophen-2-ylmethylthio)-1,2,4-triazole;

5-(5-(4-fluorophenylamino)-4H-[1,2,4]triazol-3-ylsulfanylmethyl)-furan-2-carbaldehyde;

3-anilino-5-(3,4-difluoro-benzylthio)-1,2,4-triazole;

3-(4-methyl-anilino)-5-(2-fluoro-benzylthio)-1,2,4-triazole;

3-(4-methyl-anilino)-5-(3,4-difluoro-benzylthio)-1,2,4-triazole;

3-(2-methyl-anilino)-5-(3,4-difluoro-benzylthio)-1,2,4-triazole;

3-(4-chloro-anilino)-5-(2-fluoro-benzylthio)-1,2,4-triazole;

3-(2-methyl-anilino)-5-(2-fluoro-benzylthio)-1,2,4-triazole;

3-(4-chloro-anilino)-5-(3,4-difluoro-benzylthio)-1,2,4-triazole;

3-(4-methoxy-anilino)-5-(2-fluoro-benzylthio)-1,2,4-triazole;

3-(4-methoxy-anilino)-5-(3,4-difluoro-benzylthio)-1,2,4-triazole;

3-(4-methoxy-anilino)-5-(2-methoxy-benzylthio)-1,2,4-triazole;

4-(5-(3-methoxy-benzylthio)-1H-[1,2,4]triazol-3-ylamino)-benzoic acid methyl ester;

4-(5-(3,4-difluoro-benzylthio)-1H-[1,2,4]triazol-3-ylamino)-benzoic acid methyl ester;

4-(5-(2-methoxy-benzylthio)-1H-[1,2,4]triazol-3-ylamino)-benzoic acid methyl ester;

3-(3,4-dimethoxy-anilino)-5-(3-methoxy-benzylthio)-1,2,4-triazole;

3-(3,4-dimethoxy-anilino)-5-(2-fluoro-benzylthio)-1,2,4-triazole;

3-(3,4-dimethoxy-anilino)-5-(3,4-difluoro-benzylthio)-1,2,4-triazole;

3-(3,4-dimethoxy-anilino)-5-(2-methoxy-benzylthio)-1,2,4-triazole;

[5-(2-fluoro-benzylthio)-1H-[1,2,4]triazol-3-yl]-pyridin-3-yl-amine;

[5-(3,4-difluoro-benzylthio)-1H-[1,2,4]triazol-3-yl]-pyridin-3-yl-amine;

[5-(2-methoxy-benzylthio)-1H-[1,2,4]triazol-3-yl]-pyridin-3-yl-amine;

[5-(thiophen-2-ylmethylthio)-1H-[1,2,4]triazol-3-yl]-pyridin-3-yl-amine;

3-(2-ethyl-anilino)-5-(2-fluoro-benzylthio)-1,2,4-triazole;

3-(2-ethyl-anilino)-5-(4-fluoro-benzylthio)-1,2,4-triazole;

3-(2-ethyl-anilino)-5-(3,4-difluoro-benzylthio)-1,2,4-triazole;

3-(2-methoxy-anilino)-5-(4-fluoro-benzylthio)-1,2,4-triazole;

3-(2-methoxy-anilino)-5-(3,4-difluoro-benzylthio)-1,2,4-triazole;

3-(2-methoxy-anilino)-5-(2-fluoro-benzylthio)-1,2,4-triazole;

3-(3-methyl-anilino)-5-(4-fluoro-benzylthio)-1,2,4-triazole;

3-(3-methyl-anilino)-5-(3,4-difluoro-benzylthio)-1,2,4-triazole;

3-(3-methyl-anilino)-5-(2-fluoro-benzylthio)-1,2,4-triazole;

3-(4-n-butyl-anilino)-5-(4-fluoro-benzylthio)-1,2,4-triazole;

3-(4-n-butyl-anilino)-5-(3,4-difluoro-benzylthio)-1,2,4-triazole;

3-(4-n-butyl-anilino)-5-(2-fluoro-benzylthio)-1,2,4-triazole;

3-(2,4-dimethoxy-anilino)-5-(4-fluoro-benzylthio)-1,2,4-triazole;

3-(2,4-dimethoxy-anilino)-5-(3,4-difluoro-benzylthio)-1,2,4-triazole;

3-(2,4-dimethoxy-anilino)-5-(2-fluoro-benzylthio)-1,2,4-triazole;

3-(2-methyl-4-methoxy-anilino)-5-(4-fluoro-benzylthio)-1,2,4-triazole;

3-(2-methyl-4-methoxy-anilino)-5-(3,4-difluoro-benzylthio)-1,2,4-triazole;

3-(2-methyl-4-methoxy-anilino)-5-(2-fluoro-benzylthio)-1,2,4-triazole;

3-(2,6-dimethyl-anilino)-5-(4-fluoro-benzylthio)-1,2,4-triazole;

3-(2,6-dimethyl-anilino)-5-(3,4-difluoro-benzylthio)-1,2,4-triazole;

3-(2,6-dimethyl-anilino)-5-(2-fluoro-benzylthio)-1,2,4-triazole;

3-(4-fluoro-anilino)-5-(thiophen-3-ylmethylthio)-1,2,4-triazole; and 3-(4-fluoro-anilino)-5-(furan-3-ylmethylthio)-1,2,4-triazole.

Among the more preferred compounds of formula (IA) are the following compounds:

3-(4-methyl-anilino)-5-benzylthio-1,2,4-triazole;

3-(2-methyl-anilino)-5-benzylthio-1,2,4-triazole;

3-(4-methoxy-anilino)-5-benzylthio-1,2,4-triazole;

3-methylacetate-3-anilino-5-benzylthio-1,2,4-triazole;

4-(5-benzylthio-1H-[1,2,4]triazol-3-ylamino)-benzoic Acid Methyl Ester;

3-anilino-5-(thiophen-2-ylmethylthio)-1,2,4-triazole;

3-anilino-5-(furan-3-ylmethylthio)-1,2,4-triazole;

3-anilino-5-(furan-2-ylmethylthio)-1,2,4-triazole;

3-anilino-5-(5-methyl-thiophen-2-ylmethylthio)-1,2,4-triazole;

3-anilino-5-(5-chloro-thiophen-2-ylmethylthio)-1,2,4-triazole;

3-anilino-5-(thiophen-3-ylmethylthio)-1,2,4-triazole;

3-anilino-5-(5-bromo-thiophen-2-ylmethylthio)-1,2,4-triazole;

3-(4-methyl-anilino)-5-(thiophen-2-ylmethylthio)-1,2,4-triazole;

3-(4-methyl-anilino)-5-(thiophen-3-ylmethylthio)-1,2,4-triazole;

3-(4-methyl-anilino)-5-(5-methyl-thiophen-2-ylmethylthio)-1,2,4-triazole;

3-(2-methyl-anilino)-5-(furan-2-ylmethylthio)-1,2,4-triazole;

3-(4-chloro-anilino)-5-(thiophen-2-ylmethylthio)-1,2,4-triazole;

3-(4-methoxy-anilino)-5-(5-chloro-thiophen-2-ylmethylthio)-1,2,4-triazole;

3-(2-methoxy-anilino)-5-(3-methyl-thiophen-2-ylmethylthio)-1,2,4-triazole;

3-(2-methoxy-anilino)-5-(5-methyl-thiophen-2-ylmethylthio)-1,2,4-triazole;

3-(3-methyl-anilino)-5-(furan-2-ylmethylthio)-1,2,4-triazole;

3-(3-methyl-anilino)-5-(furan-3-ylmethylthio)-1,2,4-triazole; and 3-(3-methyl-anilino)-5-(thiophen-3-ylmethylthio)-1,2,4-triazole.

Among the most preferred compounds of formula (IA) are the following compounds:

3-(2-isopropyl-anilino)-5-(thiophen-2-ylmethylthio)-1,2,4-triazole;

3-(2-isopropyl-anilino)-5-(furan-2-ylmethylthio)-1,2,4-triazole;

3-(2-isopropyl-anilino)-5-(3-methyl-thiophen-2-ylmethylthio)-1,2,4-triazole;

3-(2-isopropyl-anilino)-5-(3-chloro-thiophen-2-ylmethylthio)-1,2,4-triazole;

3-(2-isopropyl-anilino)-5-(5-methyl-thiophen-2-ylmethylthio)-1,2,4-triazole;

3-(2-isopropyl-anilino)-5-(5-chloro-thiophen-2-ylmethylthio)-1,2,4-triazole;

5-(5-(2-isopropylphenylamino)-4H-[1,2,4]triazol-3-ylsulfanylmethyl)-furan-2-carboxylic acid ethyl ester;

5-(5-(2-isopropyl amino)-4H-[1,2,4]triazol-3-ylsulfanylmethyl)-furan-2-carbaldehyde;

3-(2-isopropyl-anilino)-5-(thiophen-3-ylmethylthio)-1,2,4-triazole;

3-(2-isopropyl-anilino)-5-(furan-3-ylmethylthio)-1,2,4-triazole;

3-(4-methyl-anilino)-5-(furan-2-ylmethylthio)-1,2,4-triazole;

3-(4-methyl-anilino)-5-(furan-3-ylmethylthio)-1,2,4-triazole;

3-(2-methoxy-anilino)-5-(3-chloro-thiophen-2-ylmethylthio)-1,2,4-triazole; and 3-(2-methoxy-anilino)-5-(5-chloro-thiophen-2-ylmethylthio)-1,2,4-triazole.

Methods of Preparation

Compounds of the formulae (I) and (IA) wherein X is S and $R^3$ is H, were prepared by methods analogous to those described in Scheme 1.

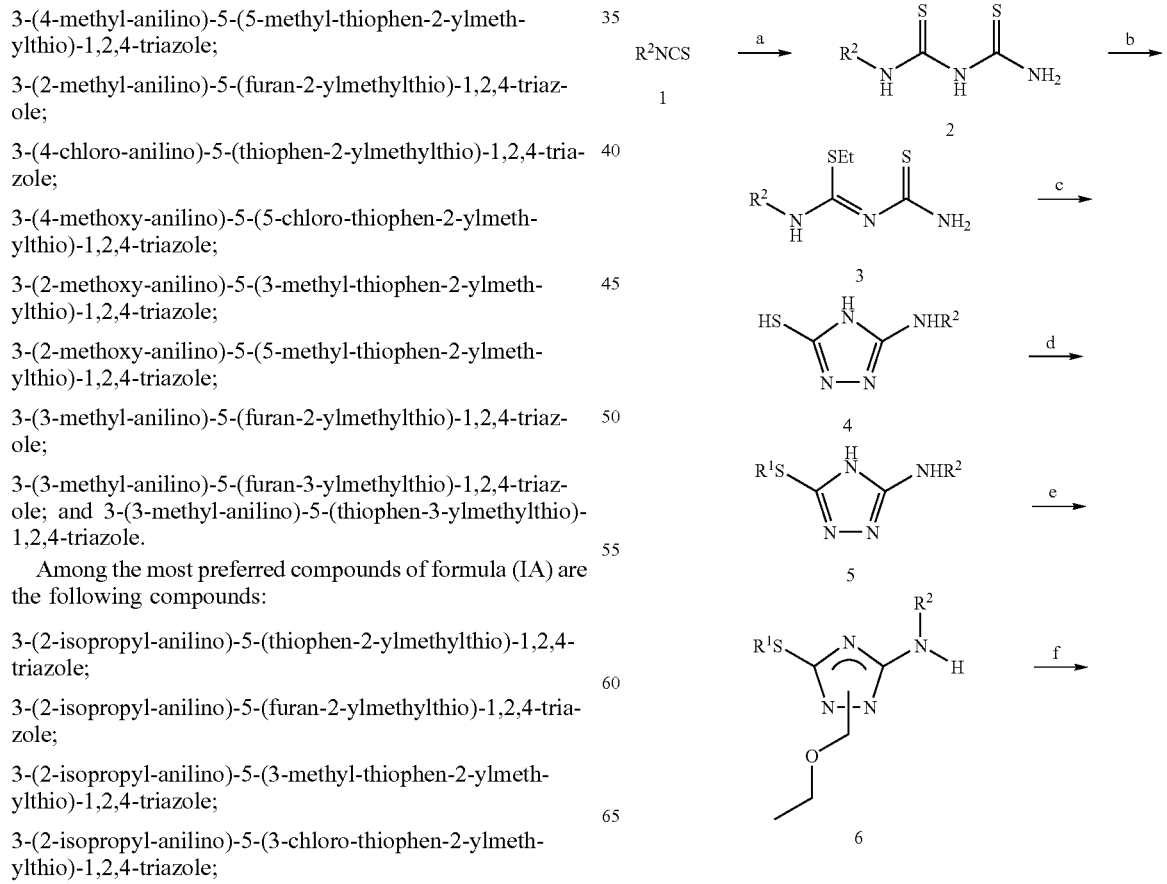

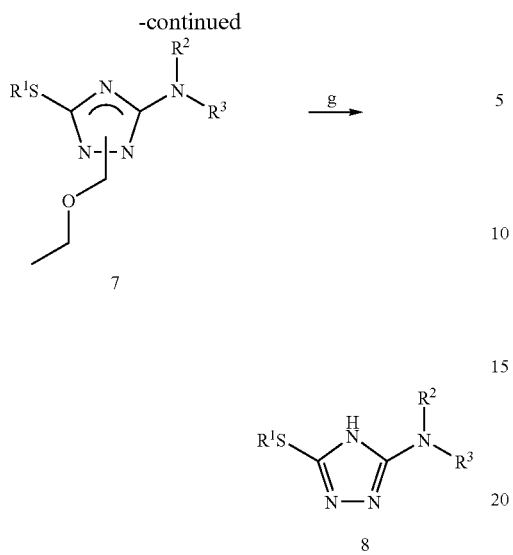

a) Thiourea, NaOH, H₂O/CH₃CN;
b) EtI, Et₃N, DMF;
c) H₂NNH₂, EtOH;
d) R¹X (X = halogen), K₂CO₃, DMF;
e) ClCH₂OCH₂CH₃, NaH, THF;
f) R³CH₂Br, NaH, DMF;
g) TFA.

An isothiocyanate (such as phenyl isothiocyanate) (1-Scheme 1) was treated with thiourea and sodium hydroxide in acetonitrile/water to provide 2-Scheme 1, which was treated with iodoethane and triethylamine in DMF to afford 3-Scheme 1. Treatment of 3-Scheme 1 with hydrazine in ethanol provided 4-Scheme 1, which was treated with an alkyl halide (such as benzyl bromide or 4-chlorobenzyl chloride) and potassium carbonate in DMF to give 5-Scheme 1. Triazole 5-Scheme 1 is protected as the methoxy methylethyl ether to afford 6-Scheme 1. Alkylation of 6-Scheme 1 with an alkyl halide (such as methyliodide, ethyliodide, i-isobutyl iodide, n-propyliodide, butyliodide, allylbromide, benzylbromide, and methyl bromoacetate) afforded the desired tertiary amine 7-Scheme 1. Deprotection of the MOM-ether 7-Scheme 1 with trifluoroacetic acid (TFA) provided the desired product 8-Scheme 1.

Compounds of the formulae (I) and (IA) wherein X is O may be prepared by methods analogous to those described in Scheme 2.

Scheme 2

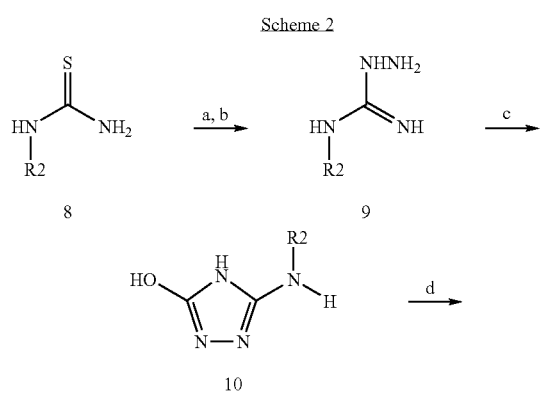

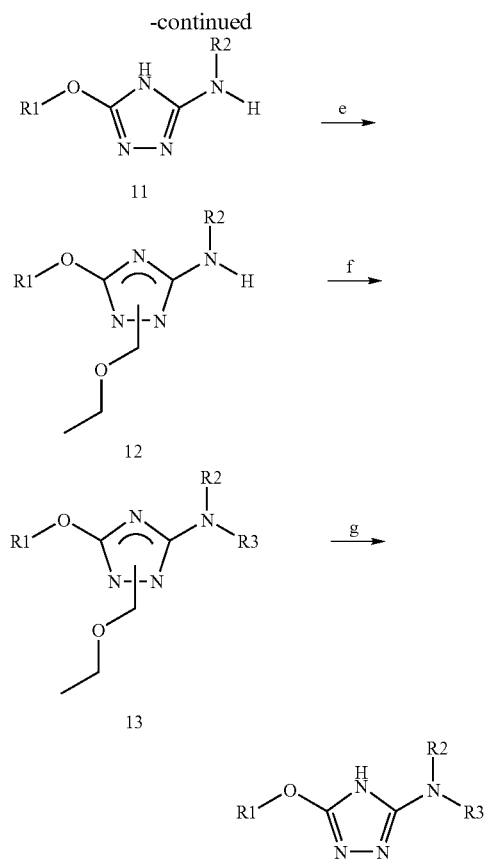

a) Thiourea, EtI, EtOH;
b) NH₂NH₂, EtOH
c) 1,1″-Carbonyldiimidazole, EtOH;
d) R¹X (X = halogen), K₂CO₃, DMF;
e) ClCH₂OCH₂CH₃, NaH, THF;
f) R3CH₂Br, NaH, DMF;
g) TFA.

A thiourea (such as phenylthiourea) (8-Scheme 2) may be treated with ethyl iodide and refluxed in EtOH, and the resulting S-ethyl thiourea is then heated in the presence of hydrazine to provide 9-Scheme 2. The hydrazine 9-Scheme 2 is treated with carbonyldiimidazole and heated to afford 10-Scheme 2. Treatment of 10-Scheme 2 with an alkyl halide (such as benzyl bromide or 4-chlorobenzyl chloride) and potassium carbonate in DMF gives 11-Scheme 2. Triazole 11-Scheme 2 is protected as the methoxy methylethyl ether to afford 12-Scheme 2. Alkylation of 12-Scheme 2 with an alkyl halide (such as methyliodide, ethyliodide, i-isobutyl iodide, n-propyliodide, butyliodide, allylbromide, benzylbromide, and methyl bromoacetate) affords the desired tertiary amine 13-Scheme 2. Deprotection of the MOM-ether 13-Scheme 2 with trifluoroacetic acid (TFA) provides the desired product 14-Scheme 2.

Formulation of Pharmaceutical Compositions

The pharmaceutically effective compounds of this invention (and the pharmaceutically acceptable salts thereof) are administered in conventional dosage forms prepared by combining a compound of this invention ("active ingredient") in an amount sufficient to treat cancer, haemangioma, proliferative retinopathy, rheumatoid arthritis, atherosclerotic neovascularization, psoriasis, ocular neovascularization or obesity ("MetAp2-mediated disease states") with standard pharmaceutical carriers or diluents according to conventional procedures well known in the art. These procedures may involve mixing, granulating and compressing or dissolving the ingredients as appropriate to the desired preparation.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl monostearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1000 mg. When a liquid carrier is used, the preparation will be in the form of a syrup, emulsion, soft gelatin capsule, sterile injectable liquid such as an ampule or nonaqueous liquid suspension.

The active ingredient may also be administered topically to a mammal in need of treatment or prophylaxis of non-MetAP2-mediated disease states. The amount of active ingredient required for therapeutic effect on topical administration will, of course, vary with the compound chosen, the nature and severity of the disease state being treated and the mammal undergoing treatment, and is ultimately at the discretion of the physician. A suitable dose of an active ingredient is 1.5 mg to 500 mg for topical administration, the most preferred dosage being 1 mg to 100 mg, for example 5 to 25 mg administered two or three times daily.

By topical administration is meant non-systemic administration and includes the application of the active ingredient externally to the epidermis, to the buccal cavity and instillation of such a compound into the ear, eye and nose, and where the compound does not significantly enter the blood stream. By systemic administration is meant oral, intravenous, intraperitoneal and intramuscular administration.

While it is possible for an active ingredient to be administered alone as the raw chemical, it is preferable to present it as a pharmaceutical formulation. The active ingredient may comprise, for topical administration, from 0.001% to 10% w/w, e.g. from 1% to 2% by weight of the formulation although it may comprise as much as 10% w/w but preferably not in excess of 5% w/w and more preferably from 0.1% to 1% w/w of the formulation.

The topical formulations of the present invention, both for veterinary and for human medical use, comprise an active ingredient together with one or more acceptable carrier(s) therefor and optionally any other therapeutic ingredient(s). The carrier(s) must be 'acceptable' in the sense of being compatible with the other ingredients of the formulation and not deleterious to the recipient thereof.

Formulations suitable for topical administration include liquid or semi-liquid preparations suitable for penetration through the skin to the site of inflammation such as liniments, lotions, creams, ointments or pastes, and drops suitable for administration to the eye, ear or nose.

Drops according to the present invention may comprise sterile aqueous or oily solutions or suspensions and may be prepared by dissolving the active ingredient in a suitable aqueous or alcoholic solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol. The formulation may incorporate any suitable surface-active agent such as an anionic, cationic or non-ionic surfactant such as esters or polyoxyethylene derivatives thereof. Suspending agents such as natural gums, cellulose derivatives or inorganic materials such as silicaceous silicas, and other ingredients such as lanolin, may also be included.

The active ingredient may also be administered by inhalation. By "inhalation" is meant intranasal and oral inhalation administration. Appropriate dosage forms for such administration, such as an aerosol formulation or a metered dose inhaler, may be prepared by conventional techniques. The daily dosage amount of the active ingredient administered by inhalation is from about 0.1 mg to about 100 mg per day, preferably about 1 mg to about 10 mg per day.

In one aspect, this invention relates to a method of treating cancer, haemangioma, proliferative retinopathy, rheumatoid arthritis, atherosclerotic neovascularization, psoriasis, ocular neovascularization or obesity, all in mammals, preferably humans, which comprises administering to such mammal an effective amount of a MetAP2 inhibitor, in particular, a compound of this invention.

By the term "treating" is meant either prophylactic or therapeutic therapy. Such compound can be administered to such mammal in a conventional dosage form prepared by combining the compound of this invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. The compound is administered to a mammal in need of treatment for cancer, haemangioma, proliferative retinopathy, rheumatoid arthritis, atherosclerotic neovascularization, psoriasis, ocular neovascularization or obesity, in an amount sufficient to decrease symptoms associated with these disease states. The route of administration may be oral or parenteral.

The term parenteral as used herein includes intravenous, intramuscular, subcutaneous, intra-rectal, intravaginal or intraperitoneal administration. The subcutaneous and intramuscular forms of parenteral administration are generally preferred. The daily parenteral dosage regimen will preferably be from about 30 mg to about 300 mg per day of active ingredient. The daily oral dosage regimen will preferably be from about 100 mg to about 2000 mg per day of active ingredient.

It will be recognized by one of skill in the art that the optimal quantity and spacing of individual dosages of a compound of this invention will be determined by the nature and extent of the condition being treated, the form, route and site of administration, and the particular mammal being treated, and that such optimums can be determined by conventional techniques. It will also be appreciated by one of skill in the art that the optimal course of treatment, i.e., the number of doses of the compound given per day for a defined number of days, can be ascertained by those skilled in the art using conventional course of treatment determination tests.

EXAMPLES

The invention will now be described by reference to the following examples which are merely illustrative and are not to be construed as a limitation of the scope of the present invention. In the Examples, proton NMR spectra were performed upon a Bruker 400 MHz NMR spectrometer, unless otherwise indicated.

Example 1

Preparation of 3-anilino-5-benzylthio-1,2,4-triazole a) 1-Phenyl-2,4-dithiobiuret To a stirring solution of NaOH (0.52 g, 13.1 mmol) in 60 mL of 10% $H_2O:CH_3CN$ was added thiourea (1.0 g, 13.1 mmol). The resulting suspension was heated to 40° C. for 20 min. and then cooled to RT. To this mixture was added phenylisothiocyanate (1.5 ml, 13.1 mmol), and the clear yellow solution was stirred overnight. After stirring for 12 h, 1 N HCl was added until a white precipitate formed. The precipitate was filtered, washed with $H_2O$, and dried under vacuum to produce the title compound as a light yellow powder (0.78 g, 30%). $^1$H-NMR (400 MHz, d6-DMSO) δ7.25 (t, 2H, J=7.3 Hz), 7.40 (t, 2H, J=7.9 Hz), 7.56 (d, 1H, J=7.9 Hz), 9.13-9.29 (broad singlet, 1H), and 10.26-10.79 (broad singlet, 2H).

b) 2-Ethyl-1-phenyl-2-isodithiobiuret

To a stirring solution of the compound of Example 1(a) (150 mg, 0.70 mmol) in 4 mL of DMF was added triethylamine (57 uL, 0.70 mmol). The resulting yellow/green solution was stirred for 10 min at RT. To this solution was added ethyl iodide (100 uL, 0.70 mmol), and the reaction mixture was stirred for 2 h at RT. The yellow solution was poured into 20 mL of $H_2O$ and extracted four times with EtOAc. The organic extracts were dried over $Na_2SO_4$, filtered, concentrated, and the crude residue was subjected to column chromatography (silica gel; ethyl acetate/hexane) to afford the title compound as a white crystalline solid (108 mg, 64%). $^1$H-NMR (400 MHz, d6-DMSO) δ1.22 (t, 3H, J=7.2 Hz), 2.96 (quartet, 2H, J=7.2 Hz), 6.85 (d, 1H, J=7.6 Hz), 7.16 (t, 1H, J=7.2 Hz), 7.29-7.41 (m, 3H), 8.27 (broad singlet, 1H), 9.89 (broad singlet, 1H), and 10.99 (broad singlet, 1H).

c) 3-anilino-5-mercapto-1,2,4-triazole

To a stirring solution of the compound of Example 1(b) in 2 mL of EtOH was added 50 uL of anhydrous hydrazine. The reaction mixture was heated at 80° C. for 1 h, concentrated to dryness, and then purified by preparative HPLC to yield the title compound as a white solid (30 mg, 37%). MS (ESI) 190.90 (M–H)$^+$.

d) 3-anilino-5-benzylthio-1,2,4-triazole

To a stirring solution of the compound of Example 1 (c) (23 mg, 0.12 mmol) in 1.2 mL of DMF was added $K_2CO_3$ (17 mg, 0.12 mmol), followed by benzyl bromide (20 mg, 0.12 mmol). The mixture was stirred overnight, filtered, and purified by preparative HPLC to afford the title compound as a white solid (30 mg, 70%). $^1$H-NMR (400 MHz, d6-DMSO) δ9.30 (broad singlet, 1H), 7.47 (d, 2H, J=8.1 Hz), 7.39 (d, 2H, J=7.3 Hz), 7.31 (t, 2H, J=7.3 Hz), 7.23 (quartet, 3H, J=7.3 Hz), 6.82 (t, 1H, J=7.3 Hz), and 4.3 (s, 2H).

Example 2

Preparation of 3-anilino-5-(4-chlorobenzylthio)-1,2,4-triazole

Following the procedure of Example 1(a)-1(d), except substituting 4-chlorobenzyl bromide for benzyl bromide in step 1(d), the title compound was prepared as a white solid. $^1$H-NMR (400 MHz, d6-DMSO) δ9.32 (broad singlet, 1H), 7.46 (d, 2H, J=7.8 Hz), 7.41 (d, 2H, J=8.4 Hz), 7.36 (d, 2H, J=8.4 Hz), 7.22 (t, 2H, J=7.8 Hz), 6.82 (t, 1H, J=7.24 Hz), and 4.33 (s, 2H).

Example 3

Preparation of 3-anilino-5-methylthio-1,2,4-triazole

Following the procedure of Example 1(a)-1(d), except methyl iodide was substituted for benzyl bromide in step 1(d), the title compound was prepared as a white solid. MS (ESI) 413.2 (2M+H)$^+$.

Example 4

Preparation of 3-anilino-5-allylthio-1,2,4-triazole

Following the procedure of Example 1(a)-1(d), except allyl bromide was substituted for benzyl bromide in step 1(d), the title compound was prepared as a white solid. MS (ESI) 233.0 (M+H)$^+$.

Example 5

Preparation of 3-anilino-5-(2-methyl-2-butenylthio)-1,2,4-triazole

Following the procedure of Example 1(a)-1(d), except 1-bromo-3-methylbut-2-ene was substituted for benzyl bromide in step 1(d), the title compound was prepared as a white solid. MS (ESI) 261.2 (M+H)$^+$.

Example 6

Preparation of 3-anilino-5-(2-methyl-butylthio)-1,2,4-triazole

Following the procedure of Example 1(a)-1(d), except 1-bromo-3-methylbutane was substituted for benzyl bromide in step 1(d), the title compound was prepared as a white solid. MS (ESI) 263.2 (M+H)+.

Example 7

Preparation of 3-anilino-5-(2-methyl-2-pentenylthio)-1,2,4-triazole

Following the procedure of Example 1(a)-1(d), except 5-bromo-2-methyl-2-pentene was substituted for benzyl bromide in step 1(d), the title compound was prepared as a white solid. MS (ESI) 275.2 (M+H)+.

Example 8

Preparation of 3-anilino-5-(α-methylbenzylthio)-1,2,4-triazole

Following the procedure of Example 1(a)-1(d), except (1-bromoethyl) benzene was substituted for benzyl bromide in step 1(d), the title compound was prepared as a white solid. MS (ESI) 297.2 (M+H)+.

Example 9

Preparation of 3-anilino-5-(cyclohexylmethylthio)-1,2,4-triazole

Following the procedure of Example 1(a)-1(d), except bromomethylcyclohexane was substituted for benzyl bromide in step 1(d), the title compound was prepared as a white solid. MS (ESI) 289.0 (M+H)+.

Example 10

Preparation of 3-anilino-5-(propyl acetylthio)-1,2,4-triazole

Following the procedure of Example 1(a)-1(d), except propyl bromoacetate was substituted for benzyl bromide in step 1(d), the title compound was prepared as a white solid. MS (ESI) 293.2 (M+H)+.

Example 11

Preparation of 3-anilino-5-(3,3-dimethoxy-propylthio)-1,2,4-triazole

Following the procedure of Example 1(a)-1(d), except 3-bromo-1,1-dimethoxy-propane was substituted for benzyl bromide in step 1(d), the title compound was prepared as a white solid. MS (ESI) 295.2 (M+H)+.

Example 12

Preparation of 3-anilino-5-(2-phenethylthio)-1,2,4-triazole

Following the procedure of Example 1(a)-1(d), except (2-bromoethyl)benzene was substituted for benzyl bromide in step 1(d), the title compound was prepared as a white solid. MS (ESI) 297.2 (M+H)+.

Example 13

Preparation of 3-anilino-5-(5-methyl-isoxazol-3-ylmethylthio)-1,2,4-triazole

Following the procedure of Example 1(a)-1(d), except 3-(chloromethyl)-5-methylisoxazole was substituted for benzyl bromide in step 1(d), the title compound was prepared as a white solid. MS (ESI) 288.2 (M+H)+.

Example 14

Preparation of 3-anilino-5-(3-phenyl-[1,2,4]oxadiazol-5-ylmethylthio)-1,2,4-triazole Following the procedure of Example 1(a)-1(d), except 3-chloromethyl-5-phenyl-1,2,4-oxadiazole was substituted for benzyl bromide in step 1(d), the title compound was prepared as a white solid. MS (ESI) 351.2 (M+H)+.

Example 15

Preparation of 3-anilino-5-(1H-benzoimidazol-2-ylmethylthio)-1,2,4-triazole

Following the procedure of Example 1(a)-1(d), except 2-(chloromethyl)-benzimidazole was substituted for benzyl bromide in step 1(d), the title compound was prepared as a white solid. MS (ESI) 323.2 (M+H)+.

Example 16

Preparation of 3-anilino-5-(2-(4-chlorophenyl)-thiazol-4-ylmethylthio)-1,2,4-triazole Following the procedure of Example 1(a)-1(d), except 4-chloromethyl-2-(4-chlorophenyl)thiazole was substituted for benzyl bromide in step 1(d), the title compound was prepared as a white solid. MS (ESI) 400.0 (M+H)+.

Example 17

Preparation of 3-anilino-5-(2-methyl-thiazol-4-ylmethylthio)-1,2,4-triazole

Following the procedure of Example 1(a)-1(d), except 4-chloromethyl-2-methylthiazole was substituted for benzyl bromide in step 1(d), the title compound was prepared as a white solid. MS (ESI) 304.2 (M+H)+.

Example 18

Preparation of 3-anilino-5-(pyridin-2-ylmethylthio)-1,2,4-triazole

Following the procedure of Example 1(a)-1(d), except 2-(chloromethyl)pyridine was substituted for benzyl bromide in step 1(d), the title compound was prepared as a white solid. MS (ESI) 284.2 (M+H)+.

Example 19

Preparation of 3-anilino-5-(pyridin-4-ylmethylthio)-1,2,4-triazole

Following the procedure of Example 1(a)-1(d), except 4-(chloromethyl)pyridine was substituted for benzyl bromide in step 1(d), the title compound was prepared as a white solid. MS (ESI) 284.0 (M+H)+.

Example 20

Preparation of 3-anilino-5-(thiophen-2-ylmethylthio)-1,2,4-triazole

Following the procedure of Example 1(a)-1(d), except 2-chloromethylthiophene was substituted for benzyl bromide in step 1(d), the title compound was prepared as a white solid. MS (ESI) 289.0 (M+H)+.

Example 21

Preparation of 3-anilino-5-(4-i-propyl-benzylthio)-1,2,4-triazole

Following the procedure of Example 1(a)-1(d), except 4-isopropylbenzyl bromide was substituted for benzyl bromide in step 1(d), the title compound was prepared as a white solid. MS (ESI) 325.2 (M+H)+.

Example 22

Preparation of 3-anilino-5-(quinolin-8-ylmethythio)-1,2,4-triazole

Following the procedure of Example 1(a)-1(d), except 8-bromomethylquinoline was substituted for benzyl bromide in step 1(d), the title compound was prepared as a white solid. MS (ESI) 334.2 (M+H)+.

Example 23

Preparation of 3-anilino-5-(4-acetamido-benzylthio)-1,2,4-triazole

Following the procedure of Example 1(a)-1(d), except 4-acetamidobenzyl chloride was substituted for benzyl bromide in step 1(d), the title compound was prepared as a white solid. MS (ESI) 340.2 (M+H)+.

Example 24

Preparation of 4-(5-anilino-2H-[1,2,4]triazol-3-yl thiomethy)-benzoic Acid

Following the procedure of Example 1(a)-1(d), except 4-(chloromethyl)benzoic acid was substituted for benzyl bromide in step 1(d), the title compound was prepared as a white solid. MS (ESI) 327.2 (M+H)+.

Example 25

Preparation of 3-anilino-5-(2-methyl-benzylthio)-1,2,4-triazole

Following the procedure of Example 1(a)-1(d), except 2-methylbenzyl bromide was substituted for benzyl bromide in step 1(d), the title compound was prepared as a white solid. MS (ESI) 297.0 (M+H)+.

Example 26

Preparation of 3-anilino-5-(4-trifluoromethyl-benzylthio)-1,2,4-triazole

Following the procedure of Example 1(a)-1(d), except 4-(trifluoromethyl)benzyl bromide was substituted for benzyl bromide in step 1(d), the title compound was prepared as a white solid. MS (ESI) 350.8 (M+H)+.

Example 27

Preparation of 3-anilino-5-(3,5-dimethyl-benzylthio)-1,2,4-triazole

Following the procedure of Example 1(a)-1(d), except 3,5-dimethylbenzyl bromide was substituted for benzyl bromide in step 1(d), the title compound was prepared as a white solid. MS (ESI) 311.4 (M+H)+.

Example 28

Preparation of 3-anilino-5-(4-cyano-benzylthio)-1,2,4-triazole

Following the procedure of Example 1(a)-1(d), except 4-cyanobenzyl bromide was substituted for benzyl bromide in step 1(d), the title compound was prepared as a white solid. MS (ESI) 308.2 (M+H)+.

Example 29

Preparation of 3-anilino-5-(3,4-difluoro-benzylthio)-1,2,4-triazole

Following the procedure of Example 1(a)-1(d), except 3,4-diflurobenzyl bromide was substituted for benzyl bromide in step 1(d), the title compound was prepared as a white solid. MS (ESI) 319.0 (M+H)+.

Example 30

Preparation of 3-anilino-5-(furan-2-ylmethylthio)-1,2,4-triazole

Following the procedure of Example 1(a)-1(d), except 2-chloromethyl-furan (Berry, J. M.; Watson, C. Y.; Whish, W. J. D.; Threadgill, M. D. *J. Chem. Soc. Perkin Trans.* 1 1997, 8, 1147) was substituted for benzyl bromide in step 1(d), the title compound was prepared as a white solid. MS (ESI) 273.2 (M+H)+.

Example 31

Preparation of 3-anilino-5-(3-methyl-thiophen-2-ylmethylthio)-1,2,4-triazole

Following the procedure of Example 1(a)-1(d), except 2-chloromethyl-3-methyl-thiophene (Chauhan, P. M. S.; Jenkins, G.; Walker, S. M.; Storr, R. C. *Tetrahedron Lett.* 1988, 29(1), 117) was substituted for benzyl bromide in step 1(d), the title compound was prepared as a white solid. MS (ESI) 303.2 (M+H)+.

Example 32

Preparation of 3-anilino-5-(3-chloro-thiophen-2-ylmethylthio)-1,2,4-triazole

Following the procedure of Example 1(a)-1(d), except 2-chloromethyl-3-chloro-thiophene (Chauhan, P. M. S.; Jenkins, G.; Walker, S. M.; Storr, R. C. *Tetrahedron Lett.* 1988, 29(1), 117) was substituted for benzyl bromide in step 1(d), the title compound was prepared as a white solid. MS (ESI) 323.2 (M+H)$^+$.

Example 33

Preparation of 3-anilino-5-(5-methyl-thiophen-2-ylmethylthio)-1,2,4-triazole

Following the procedure of Example 1(a)-1(d), except 2-chloromethyl-5-methyl-thiophene (Moradpour, A. *J. Chem. Soc. Perkin Trans.* 1, 1993, 1, 7) was substituted for benzyl bromide in step 1(d), the title compound was prepared as a white solid. MS (ESI) 303.2 (M+H)$^+$.

Example 34

Preparation of 3-anilino-5-(5-chloro-thiophen-2-ylmethylthio)-1,2,4-triazole

Following the procedure of Example 1(a)-1(d), except 2-chloromethyl-5-chloro-thiophene was substituted for benzyl bromide in step 1(d), the title compound was prepared as a white solid. MS (ESI) 323.0 (M+H)$^+$.

Example 35

Preparation of 5-(5-phenylamino-4H-[1,2,4]triazol-3-ylsulfanylmethyl)-furan-2-carboxylic Acid Ethyl Ester Following the procedure of Example 1(a)-1(d), except 5-chloromethyl-furan-2-carboxylic acid ethyl ester was substituted for benzyl bromide in step 1(d), the title compound was prepared as a white solid. MS (ESI) 345.2 (M)$^+$.

Example 36

Preparation of 3-anilino-5-(5-bromo-thiophen-2-ylmethylthio)-1,2,4-triazole

Following the procedure of Example 1(a)-1(d), except 2-chloromethyl-5-bromo-thiophene (Clapp, R. C.; Clark, J. H; Vaughan, J. R.; English, J. P.; Anderson, G. W. *J. Am. Chem. Soc.* 1947, 60, 1549) was substituted for benzyl bromide in step 1(d), the title compound was prepared as a white solid. MS (ESI) 367.0 (M)$^+$.

Example 37

Preparation of 5-(5-phenylamino-4H-[1,2,4]triazol-3-ylsulfanylmethyl)-furan-2-carbaldehyde Following the procedure of Example 1(a)-1(d), except 5-chloromethyl-furan-2-carbaldehyde (Sanda, K.; Rigal, L.; Delmas, M.; Gaset, A. *Synthesis* 1992, 6, 541) was substituted for benzyl bromide in step 1(d), the title compound was prepared as a white solid. MS (ESI) 301.2 (M+H)$^+$.

Example 38

Preparation of 3-anilino-5-(thiophen-3-ylmethylthio)-1,2,4-triazole

Following the procedure of Example 1(a)-1(d), except 3-chloromethylthiophene (Lamy, J.; Lavit, D.; Buu-Hoi, N. P. *J. Chem. Soc.* 1958, 4202) was substituted for benzyl bromide in step 1(d), the title compound was prepared as a white solid. MS (ESI) 289.0 (M+H)$^+$.

Example 39

Preparation of 3-anilino-5-(furan-3-ylmethylthio)-1,2,4-triazole

Following the procedure of Example 1(a)-1(d), except 3-chloromethyl-furan (Arena, G.; Cali, R.; Maccarone, E.; Passerini, A. *J. Chem. Soc. Perkin Trans.* 2 1993, 10, 1941) was substituted for benzyl bromide in step 1(d), the title compound was prepared as a white solid. MS (ESI) 273.2 (M+H)$^+$.

Example 40

Preparation of 3-(4-methyl-anilino)-5-benzylthio-1,2,4-triazole

Following the procedure of Example 1(a)-1(d), except p-tolyl isothiocyanate was substituted for phenylisothiocyanate in step 1(a), the title compound was prepared as a white solid. MS (ESI) 297.0 (M+H)$^+$.

Example 41

Preparation of 3-(4-methyl-anilino)-5-(thiophen-2-ylmethylthio)-1,2,4-triazole

Following the procedure of Example 1(a)-1(d), except p-tolyl isothiocyanate was substituted for phenylisothiocyanate in step 1(a) and 2-chloromethylthiophene was substituted for benzyl bromide in step 1(d), the title compound was prepared as a white solid. MS (ESI) 303.2 (M+H)$^+$.

Example 42

Preparation of 3-(4-methyl-anilino)-5-(cyclohexylmethylthio)-1,2,4-triazole

Following the procedure of Example 1(a)-1(d), except p-tolyl isothiocyanate was substituted for phenylisothiocyanate in step 1(a) and bromomethylcyclohexane was substituted for benzyl bromide in step 1(d), the title compound was prepared as a white solid. MS (ESI) 303.0 (M+H)$^+$.

Example 43

Preparation of 3-(4-methyl-anilino)-5-(pyridin-4-ylmethylthio)-1,2,4-triazole

Following the procedure of Example 1(a)-1(d), except p-tolyl isothiocyanate was substituted for phenylisothiocyanate in step 1(a) and 4-(chloromethyl)pyridine was substituted for benzyl bromide in step 1(d), the title compound was prepared as a white solid. MS (ESI) 298.2 (M+H)$^+$.

Example 44

Preparation of 3-(4-methyl-anilino)-5-(2-methyl-2-butenylthio)-1,2,4-triazole

Following the procedure of Example 1(a)-1(d), except p-tolyl isothiocyanate was substituted for phenylisothiocyanate in step 1(a) and 1-bromo-3-methylbut-2-ene was substituted for benzyl bromide in step 1(d), the title compound was prepared as a white solid. MS (ESI) 275.2 $(M+H)^+$.

Example 45

Preparation of 3-(4-methyl-anilino)-5-(2-fluoro-benzylthio)-1,2,4-triazole

Following the procedure of Example 1(a)-1(d), except p-tolyl isothiocyanate was substituted for phenylisothiocyanate in step 1(a) and 2-fluorobenzyl bromide was substituted for benzyl bromide in step 1(d), the title compound was prepared as a white solid. MS (ESI) 315.0 $(M+H)^+$.

Example 46

Preparation of 3-(4-methyl-anilino)-5-(5-methyl-isoxazol-3-ylmethylthio)-1,2,4-triazole Following the procedure of Example 1(a)-1(d), except p-tolyl isothiocyanate was substituted for phenylisothiocyanate in step 1(a) and 3-(chloromethyl)-5-methylisoxazole was substituted for benzyl bromide in step 1(d), the title compound was prepared as a white solid. MS (ESI) 302.2 $(M+H)^+$.

Example 47

Preparation of 3-(4-methyl-anilino)-5-(2-methyl-benzylthio)-1,2,4-triazole

Following the procedure of Example 1(a)-1(d), except p-tolyl isothiocyanate was substituted for phenylisothiocyanate in step 1(a) and 2-methylbenzyl bromide was substituted for benzyl bromide in step 1(d), the title compound was prepared as a white solid. MS (ESI) 311.2 $(M+H)^+$.

Example 48

Preparation of 3-(4-methyl-anilino)-5-(3,4-difluoro-benzylthio)-1,2,4-triazole

Following the procedure of Example 1(a)-1(d), except p-tolyl isothiocyanate was substituted for phenylisothiocyanate in step 1(a) and 3,4-difluorobenzyl bromide was substituted for benzyl bromide in step 1(d), the title compound was prepared as a white solid. MS (ESI) 333.2 $(M+H)^+$.

Example 49

Preparation of 3-(4-methyl-anilino)-5-(2-methoxy-benzylthio)-1,2,4-triazole

Following the procedure of Example 1(a)-1(d), except p-tolyl isothiocyanate was substituted for phenylisothiocyanate in step 1(a) and 2-methoxybenzyl bromide was substituted for benzyl bromide in step 1(d), the title compound was prepared as a white solid. MS (ESI) 327.2 $(M+H)^+$.

Example 50

Preparation of 3-(4-methyl-anilino)-5-(2-methyl-thiazol-4-ylmethylthio)-1,2,4-triazole Following the procedure of Example 1(a)-1(d), except p-tolyl isothiocyanate was substituted for phenylisothiocyanate in step 1(a) and 4-chloromethyl-2-methylthiazole was substituted for benzyl bromide in step 1(d), the title compound was prepared as a white solid. MS (ESI) 318.2 $(M+H)^+$.

Example 51

Preparation of 3-(4-methyl-anilino)-5-(pyridin-2-ylmethylthio)-1,2,4-triazole

Following the procedure of Example 1(a)-1(d), except p-tolyl isothiocyanate was substituted for phenylisothiocyanate in step 1(a) and 2-(chloromethyl)pyridine was substituted for benzyl bromide in step 1(d), the title compound was prepared as a white solid. MS (ESI) 298.2 $(M+H)^+$.

Example 52

Preparation of 3-(4-methyl-anilino)-5-(furan-2-ylmethylthio)-1,2,4-triazole

Following the procedure of Example 1(a)-1(d), except p-tolyl isothiocyanate was substituted for phenylisothiocyanate in step 1(a) and 2-chloromethyl-furan (Berry, J. M.; Watson, C. Y.; Whish, W. J. D.; Threadgill, M. D. *J. Chem. Soc. Perkin Trans.* 1 1997, 8, 1147) was substituted for benzyl bromide in step 1(d), the title compound was prepared as a white solid. MS (ESI) 287.2 $(M+H)^+$.

Example 53

Preparation of 3-(4-methyl-anilino)-5-(3-methyl-thiophen-2-ylmethylthio)-1,2,4-triazole Following the procedure of Example 1(a)-1(d), except p-tolyl isothiocyanate was substituted for phenylisothiocyanate in step 1(a) and 2-chloromethyl-3-methyl-thiophene (Chauhan, P. M. S.; Jenkins, G.; Walker, S. M.; Storr, R. C. *Tetrahedron Lett.* 1988, 29(1), 117) was substituted for benzyl bromide in step 1(d), the title compound was prepared as a white solid. MS (ESI) 317.2 $(M+H)^+$.

Example 54

Preparation of 3-(4-methyl-anilino)-5-(3-chloro-thiophen-2-ylmethylthio)-1,2,4-triazole Following the procedure of Example 1(a)-1(d), except p-tolyl isothiocyanate was substituted for phenylisothiocyanate in step 1(a) and 2-chloromethyl-3-chloro-thiophene (Chauhan, P. M. S.; Jenkins, G.; Walker, S. M.; Storr, R. C. *Tetrahedron Lett.* 1988, 29(1), 117) was substituted for benzyl bromide in step 1(d), the title compound was prepared as a white solid. MS (ESI) 337.2 $(M+H)^+$.

Example 55

Preparation of 3-(4-methyl-anilino)-5-(5-methyl-thiophen-2-ylmethylthio)-1,2,4-triazole Following the procedure of Example 1(a)-1(d), except p-tolyl isothiocyanate was substituted for phenylisothiocyanate in step 1(a) and 2-chloromethyl-5-methyl-thiophene (Moradpour, A. *J. Chem. Soc. Perkin Trans.* 1, 1993, 1, 7) was substituted for benzyl bromide in step 1(d), the title compound was prepared as a white solid. MS (ESI) 317.2 $(M+H)^+$.

Example 56

Preparation of 3-(4-methyl-anilino)-5-(5-chloro-thiophen-2-ylmethylthio)-1,2,4-triazole Following the procedure of Example 1(a)-1(d), except p-tolyl isothiocyanate was substituted for phenylisothiocyanate in step 1(a) and 2-chloromethyl-5-chloro-thiophene was substituted for benzyl bromide in step 1(d), the title compound was prepared as a white solid. MS (ESI) 337.2 $(M+H)^+$.

Example 57

Preparation of 5-(5-p-tolyl amino-4H-[1,2,4]triazol-3-ylsulfanylmethyl)-furan-2-carboxylic acid ethyl ester Following the procedure of Example 1(a)-1(d), except p-tolyl isothiocyanate was substituted for phenylisothiocyanate in step 1(a) and 5-chloromethyl-furan-2-carboxylic acid ethyl ester was substituted for benzyl bromide in step 1(d), the title compound was prepared as a white solid. MS (ESI) 359.2 $(M+H)^+$.

Example 58

Preparation of 3-(4-methyl-anilino)-5-(5-bromo-thiophen-2-ylmethylthio)-1,2,4-triazole Following the procedure of Example 1(a)-1(d), except p-tolyl isothiocyanate was substituted for phenylisothiocyanate in step 1(a) and 2-chloromethyl-5-bromo-thiophene (Clapp, R. C.; Clark, J. H; Vaughan, J. R.; English, J. P.; Anderson, G. W. *J. Am. Chem. Soc.* 1947, 60, 1549) was substituted for benzyl bromide in step 1(d), the title compound was prepared as a white solid. MS (ESI) 381.0 $(M)^+$.

Example 59

Preparation of 5-(5-p-tolyl amino-4H-[1,2,4]triazol-3-ylsulfanylmethyl)-furan-2-carbaldehyde Following the procedure of Example 1(a)-1(d), except p-tolyl isothiocyanate was substituted for phenylisothiocyanate in step 1(a) and 5-chloromethyl-furan-2-carbaldehyde (Sanda, K.; Rigal, L.; Delmas, M.; Gaset, A. *Synthesis* 1992, 6, 541) was substituted for benzyl bromide in step 1(d), the title compound was prepared as a white solid. MS (ESI) 315.2 $(M+H)^+$.

Example 60

Preparation of 3-(4-methyl-anilino)-5-(thiophen-3-ylmethylthio)-1,2,4-triazole

Following the procedure of Example 1(a)-1(d), except p-tolyl isothiocyanate was substituted for phenylisothiocyanate in step 1(a) and 3-chloromethyl-thiophene (Lamy, J.; Lavit, D.; Buu-Hoi, N. P. *J. Chem. Soc.* 1958, 4202) was substituted for benzyl bromide in step 1(d), the title compound was prepared as a white solid. MS (ESI) 303.2 $(M+H)^+$.

Example 61

Preparation of 3-(4-methyl-anilino)-5-(furan-3-ylmethylthio)-1,2,4-triazole

Following the procedure of Example 1(a)-1(d), except p-tolyl isothiocyanate was substituted for phenylisothiocyanate in step 1(a) and 3-chloromethyl-furan (Arena, G.; Cali, R.; Maccarone, E.; Passerini, A. *J. Chem. Soc. Perkin Trans.* 2 1993, 10, 1941) was substituted for benzyl bromide in step 1(d), the title compound was prepared as a white solid. MS (ESI) 287.2 $(M+H)^+$.

Example 62

Preparation of 3-(2-methyl-anilino)-5-benzylthio-1,2,4-triazole

Following the procedure of Example 1(a)-1(d), except o-tolyl isothiocyanate was substituted for phenylisothiocyanate in step 1(a) the title compound was prepared as a white solid. MS (ESI) 297.2 $(M+H)^+$.

Example 63

Preparation of 3-(2-methyl-anilino)-5-(thiophen-2-ylmethylthio)-1,2,4-triazole

Following the procedure of Example 1(a)-1(d), except o-tolyl isothiocyanate was substituted for phenylisothiocyanate in step 1(a) and 2-chloromethylthiophene was substituted for benzyl bromide in step 1(d), the title compound was prepared as a white solid. MS (ESI) 303.2 $(M+H)^+$.

Example 64

Preparation of 3-(2-methyl-anilino)-5-(cyclohexylmethylthio)-1,2,4-triazole

Following the procedure of Example 1(a)-1(d), except o-tolyl isothiocyanate was substituted for phenylisothiocyanate in step 1(a) and bromomethylcyclohexane was substituted for benzyl bromide in step 1(d), the title compound was prepared as a white solid. MS (ESI) 303.2 $(M+H)^+$.

Example 65

Preparation of 3-(2-methyl-anilino)-5-(pyridin-4-ylmethylthio)-1,2,4-triazole

Following the procedure of Example 1(a)-1(d except o-tolyl isothiocyanate was substituted for phenylisothiocyanate in step 1(a) and 4-(chloromethyl)pyridine was substi-

Example 66

Preparation of 3-(2-methyl-anilino)-5-(2-methyl-2-butenylthio)-1,2,4-triazole

Following the procedure of Example 1(a)-1(d), except o-tolyl isothiocyanate was substituted for phenylisothiocyanate in step 1(a) and 1-bromo-3-methylbut-2-ene was substituted for benzyl bromide in step 1(d), the title compound was prepared as a white solid. MS (ESI) 275.2 (M+H)$^+$.

Example 67

Preparation of 3-(2-methyl-anilino)-5-(2-fluoro-benzylthio)-1,2,4-triazole

Following the procedure of Example 1(a)-1(d), except o-tolyl isothiocyanate was substituted for phenylisothiocyanate in step 1(a) and 2-fluorobenzyl bromide was substituted for benzyl bromide in step 1(d), the title compound was prepared as a white solid. MS (ESI) 315.2 (M+H)$^+$.

Example 68

Preparation of 3-(2-methyl-anilino)-5-(5-methyl-isoxazol-3-ylmethylthio)-1,2,4-triazole Following the procedure of Example 1(a)-1(d), except o-tolyl isothiocyanate was substituted for phenylisothiocyanate in step 1(a) and 3-(chloromethyl)-5-methylisoxazole was substituted for benzyl bromide in step 1(d), the title compound was prepared as a white solid. MS (ESI) 302.0 (M+H)$^+$.

Example 69

Preparation of 3-(2-methyl-anilino)-5-(2-methyl-benzylthio)-1,2,4-triazole

Following the procedure of Example 1(a)-1(d), except o-tolyl isothiocyanate was substituted for phenylisothiocyanate in step 1(a) and 2methylbenzyl bromide was substituted for benzyl bromide in step 1(d), the title compound was prepared as a white solid. MS (ESI) 311.2 (M+H)$^+$.

Example 70

Preparation of 3-(2-methyl-anilino)-5-(3,4-difluoro-benzylthio)-1,2,4-triazole

Following the procedure of Example 1(a)-1(d), except o-tolyl isothiocyanate was substituted for phenylisothiocyanate in step 1(a) and 3,4-difluorobenzyl bromide was substituted for benzyl bromide in step 1(d), the title compound was prepared as a white solid. MS (ESI) 333.2 (M+H)$^+$.

Example 71

Preparation of 3-(2-methyl-anilino)-5-(2-methoxy-benzylthio)-1,2,4-triazole

Following the procedure of Example 1(a)-1(d), except o-tolyl isothiocyanate was substituted for phenylisothiocyanate in step 1(a) and 2-methoxybenzyl bromide was substituted for benzyl bromide in step 1(d), the title compound was prepared as a white solid. MS (ESI) 327.2 (M+H)$^+$.

Example 72

Preparation of 3-(2-methyl-anilino)-5-(2-methyl-thiazol-4-ylmethylthio)-1,2,4-triazole Following the procedure of Example 1(a)-1(d), except o-tolyl isothiocyanate was substituted for phenylisothiocyanate in step 1(a) and 4-chloromethyl-2-methylthiazole was substituted for benzyl bromide in step 1(d), the title compound was prepared as a white solid. MS (ESI) 318.2 (M+H)$^+$.

Example 73

Preparation of 3-(2-methyl-anilino)-5-(pyridin-2-ylmethylthio)-1,2,4-triazole

Following the procedure of Example 1(a)-1(d), except o-tolyl isothiocyanate was substituted for phenylisothiocyanate in step 1(a) and 2-(chloromethyl)pyridine was substituted for benzyl bromide in step 1(d), the title compound was prepared as a white solid. MS (ESI) 298.2 (M+H)$^+$.

Example 74

Preparation of 3-(2-methyl-anilino)-5-(furan-2-ylmethylthio)-1,2,4-triazole

Following the procedure of Example 1(a)-1(d), except o-tolyl isothiocyanate was substituted for phenylisothiocyanate in step 1(a) and 2chloromethyl-furan (Berry, J. M.; Watson, C. Y.; Whish, W. J. D.; Threadgill, M. D. *J. Chem. Soc. Perkin Trans.* 1 1997, 8, 1147) was substituted for benzyl bromide in step 1(d), the title compound was prepared as a white solid. MS (ESI) 287.2 (M+H)$^+$.

Example 75

Preparation of 3-(2-methyl-anilino)-5-(3-methyl-thiophen-2-ylmethylthio)-1,2,4-triazole Following the procedure of Example 1(a)-1(d), except o-tolyl isothiocyanate was substituted for phenylisothiocyanate in step 1(a) and 2-chloromethyl-3-methyl-thiophene (Chauhan, P. M. S.; Jenkins, G.; Walker, S. M.; Storr, R. C. *Tetrahedron Lett.* 1988, 29(1), 117) was substituted for benzyl bromide in step 1(d), the title compound was prepared as a white solid. MS (ESI) 317.2 (M+H)$^+$.

Example 76

Preparation of 3-(2-methyl-anilino)-5-(3-chloro-thiophen-2-ylmethylthio)-1,2,4-triazole Following the procedure of Example 1(a)-1(d), except o-tolyl isothiocyanate was substituted for phenylisothiocyanate in step 1(a) and 2-chloromethyl-3-chloro-thiophene (Chauhan, P. M. S.; Jenkins, G.; Walker, S. M.; Storr, R. C. *Tetrahedron Lett.* 1988, 29(1), 117) was substituted for benzyl bromide in step 1(d), the title compound was prepared as a white solid. MS (ESI) 337.2 (M+H)$^+$.

Example 77

Preparation of 3-(2-methyl-anilino)-5-(5-methyl-thiophen-2-ylmethylthio)-1,2,4-triazole Following the procedure of Example 1(a)-1(d), except o-tolyl isothiocyanate was substituted for phenylisothiocyanate in step 1(a) and 2-chloromethyl-5-methyl-thiophene (Moradpour, A. *J. Chem. Soc. Perkin Trans.* 1, 1993, 1, 7) was substituted for benzyl bromide in step 1(d), the title compound was prepared as a white solid. MS (ESI) 317.2 (M+H)+.

Example 78

Preparation of 3-(2-methyl-anilino)-5-(5-chloro-thiophen-2-ylmethylthio)-1,2,4-triazole Following the procedure of Example 1(a)-1(d), except o-tolyl isothiocyanate was substituted for phenylisothiocyanate in step 1(a) and 2-chloromethyl-5-chloro-thiophene was substituted for benzyl bromide in step 1(d), the title compound was prepared as a white solid. MS (ESI) 337.2 (M+H)+.

Example 79

Preparation of 5-(5-o-tolyl amino-4H-[1,2,4]triazol-3-ylsulfanylmethyl)-furan-2-carboxylic acid ethyl ester Following the procedure of Example 1(a)-1(d), except o-tolyl isothiocyanate was substituted for phenylisothiocyanate in step 1(a) and 5-chloromethyl-furan-2-carboxylic acid ethyl ester was substituted for benzyl bromide in step 1(d), the title compound was prepared as a white solid. MS (ESI) 359.2 (M+H)+.

Example 80

Preparation of 3-(2-methyl-anilino)-5-(5-bromo-thiophen-2-ylmethylthio)-1,2,4-triazole Following the procedure of Example 1(a)-1(d), except o-tolyl isothiocyanate was substituted for phenylisothiocyanate in step 1(a) and 2-chloromethyl-5-bromo-thiophene (Clapp, R. C.; Clark, J. H; Vaughan, J. R.; English, J. P.; Anderson, G. W. *J. Am. Chem. Soc.* 1947, 60, 1549) was substituted for benzyl bromide in step 1(d), the title compound was prepared as a white solid. MS (ESI) 381.0 (M)+.

Example 81

Preparation of 5-(5-o-tolyl amino-4H-[1,2,4]triazol-3-ylsulfanylmethyl)-furan-2-carbaldehyde Following the procedure of Example 1(a)-1(d), except o-tolyl isothiocyanate was substituted for phenylisothiocyanate in step 1(a) and 5-chloromethyl-furan-2-carbaldehyde (Sanda, K.; Rigal, L.; Delmas, M.; Gaset, A. *Synthesis* 1992, 6, 541) was substituted for benzyl bromide in step 1(d), the title compound was prepared as a white solid. MS (ESI) 315.2 (M+H)+.

Example 82

Preparation of 3-(2-methyl-anilino)-5-(thiophen-3-ylmethylthio)-1,2,4-triazole

Following the procedure of Example 1(a)-1(d), except o-tolyl isothiocyanate was substituted for phenylisothiocyanate in step 1(a) and 3-chloromethyl-thiophene (Lamy, J.; Lavit, D.; Buu-Hoi, N. P. *J. Chem. Soc.* 1958, 4202) was substituted for benzyl bromide in step 1(d), the title compound was prepared as a white solid. MS (ESI) 303.2 (M+H)+.

Example 83

Preparation of 3-(2-methyl-anilino)-5-(furan-3-ylmethylthio)-1,2,4-triazole

Following the procedure of Example 1(a)-1(d), except o-tolyl isothiocyanate was substituted for phenylisothiocyanate in step 1(a) and 3-chloromethyl-furan (Arena, G.; Cali, R.; Maccarone, E.; Passerini, A. *J. Chem. Soc. Perkin Trans.* 2 1993, 10, 1941) was substituted for benzyl bromide in step 1(d), the title compound was prepared as a white solid. MS (ESI) 287.2 (M+H)+.

Example 84

Preparation of 3-(4-chloro-anilino)-5-benzylthio-1,2,4-triazole

Following the procedure of Example 1(a)-1(d), except p-chlorophenyl isothiocyanate was substituted for phenylisothiocyanate in step 1(a), the title compound was prepared as a white solid. MS (ESI) 317.2 (M+H)+.

Example 85

Preparation of 3-(4-chloro-anilino)-5-(thiophen-2-ylmethylthio)-1,2,4-triazole

Following the procedure of Example 1(a)-1(d), except p-chlorophenyl isothiocyanate was substituted for phenylisothiocyanate in step 1(a) and 2-chloromethylthiophene was substituted for benzyl bromide in step 1(d), the title compound was prepared as a white solid. MS (ESI) 322.7 (M)+.

Example 86

Preparation of 3-(4-chloro-anilino)-5-(cyclohexylmethylthio)-1,2,4-triazole

Following the procedure of Example 1(a)-1(d), except p-chlorophenyl isothiocyanate was substituted for phenylisothiocyanate in step 1(a) and bromomethylcyclohexane was substituted for benzyl bromide in step 1(d), the title compound was prepared as a white solid. MS (ESI) 323.2 (M+H)+.

Example 87

Preparation of 3-(4-chloro-anilino)-5-(pyridin-4-ylmethylthio)-1,2,4-triazole

Following the procedure of Example 1(a)-1(d), except p-chlorophenyl isothiocyanate was substituted for phenyl-

Example 88

Preparation of 3-(4-chloro-anilino)-5-(2-methyl-2-butenylthio)-1,2,4-triazole

Following the procedure of Example 1(a)-1(d), except p-chlorophenyl isothiocyanate was substituted for phenylisothiocyanate in step 1(a) and 1-bromo-3-methylbut-2-ene was substituted for benzyl bromide in step 1(d), the title compound was prepared as a white solid. MS (ESI) 295.2 (M+H)$^+$.

Example 89

Preparation of 3-(4-chloro-anilino)-5-(2-fluoro-benzylthio)-1,2,4-triazole

Following the procedure of Example 1(a)-1(d), except p-chlorophenyl isothiocyanate was substituted for phenylisothiocyanate in step 1(a) and 2-fluorobenzyl bromide was substituted for benzyl bromide in step 1(d), the title compound was prepared as a white solid. MS (ESI) 335.2 (M+H)$^+$.

Example 90

Preparation of 3-(4-chloro-anilino)-5-(5-methyl-isoxazol-3-ylmethylthio)-1,2,4-triazole Following the procedure of Example 1(a)-1(d), except p-chlorophenyl isothiocyanate was substituted for phenylisothiocyanate in step 1(a) and 3-(chloromethyl)-5-methylisoxazole was substituted for benzyl bromide in step 1(d), the title compound was prepared as a white solid. MS (ESI) 322.0 (M+H)$^+$.

Example 91

Preparation of 3-(4-chloro-anilino)-5-(2-methyl-benzylthio)-1,2,4-triazole

Following the procedure of Example 1(a)-1(d), except p-chlorophenyl isothiocyanate was substituted for phenylisothiocyanate in step 1(a) and 2-methylbenzyl bromide was substituted for benzyl bromide in step 1(d), the title compound was prepared as a white solid. MS (ESI) 331.0 (M+H)$^+$.

Example 92

Preparation of 3-(4-chloro-anilino)-5-(3,4-difluoro-benzylthio)-1,2,4-triazole

Following the procedure of Example 1(a)-1(d), except p-chlorophenyl isothiocyanate was substituted for phenylisothiocyanate in step 1(a) and 3,4-difluorobenzyl bromide was substituted for benzyl bromide in step 1(d), the title compound was prepared as a white solid. MS (ESI) 352.8 (M)$^+$.

Example 93

Preparation of 3-(4-chloro-anilino)-5-(2-methoxy-benzylthio)-1,2,4-triazole

Following the procedure of Example 1(a)-1(d), except p-chlorophenyl isothiocyanate was substituted for phenylisothiocyanate in step 1(a) and 2-methoxybenzyl chloride was substituted for benzyl bromide in step 1(d), the title compound was prepared as a white solid. MS (ESI) 347.0 (M+H)$^+$.

Example 94

Preparation of 3-(4-chloro-anilino)-5-(2-methyl-thiazol-4-ylmethylthio)-1,2,4-triazole Following the procedure of Example 1(a)-1(d), except p-chlorophenyl isothiocyanate was substituted for phenylisothiocyanate in step 1(a) and 4-chloromethyl-2-methylthiazole was substituted for benzyl bromide in step 1(d), the title compound was prepared as a white solid. MS (ESI) 338.2 (M+H)$^+$.

Example 95

Preparation of 3-(4-chloro-anilino)-5-(pyridin-2-ylmethylthio)-1,2,4-triazole

Following the procedure of Example 1(a)-1(d), except p-chlorophenyl isothiocyanate was substituted for phenylisothiocyanate in step 1(a) and 2-(chloromethyl)pyridine was substituted for benzyl bromide in step 1(d), the title compound was prepared as a white solid. MS (ESI) 318.0 (M+H)$^+$.

Example 96

Preparation of 3-(4-methoxy-anilino)-5-benzylthio-1,2,4-triazole

Following the procedure of Example 1(a)-1(d), except p-methoxyphenyl isothiocyanate was substituted for phenylisothiocyanate in step 1(a), the title compound was prepared as a white solid. MS (ESI) 313.2 (M+H)$^+$.

Example 97

Preparation of 3-(4-methoxy-anilino)-5-(thiophen-2-ylmethylthio)-1,2,4-triazole

Following the procedure of Example 1(a)-1(d), except p-methoxyphenyl isothiocyanate was substituted for phenylisothiocyanate in step 1(a) and 2-chloromethylthiophene was substituted for benzyl bromide in step 1(d), the title compound was prepared as a white solid. MS (ESI) 319.0 (M+H)$^+$.

Example 98

Preparation of 3-(4-methoxy-anilino)-5-(cyclohexyl-methylthio)-1,2,4-triazole

Following the procedure of Example 1(a)-1(d), except p-methoxyphenyl isothiocyanate was substituted for phenylisothiocyanate in step 1(a) and bromomethylcyclohexane was substituted for benzyl bromide in step 1(d), the title compound was prepared as a white solid. MS (ESI) 319.2 (M+H)$^+$.

Example 99

Preparation of 3-(4-methoxy-anilino)-5-(pyridin-4-ylmethylthio)-1,2,4-triazole

Following the procedure of Example 1(a)-1(d), except p-methoxyphenyl isothiocyanate was substituted for phenylisothiocyanate in step 1(a) and 4-(chloromethyl)pyridine was substituted for benzyl bromide in step 1(d), the title compound was prepared as a white solid. MS (ESI) 314.2 (M+H)$^+$.

Example 100

Preparation of 3-(4-methoxy-anilino)-5-(2-methyl-2-butenylthio)-1,2,4-triazole

Following the procedure of Example 1(a)-1(d), except p-methoxyphenyl isothiocyanate was substituted for phenylisothiocyanate in step 1(a) and 1-bromo-3-methylbut-2-ene was substituted for benzyl bromide in step 1(d), the title compound was prepared as a white solid. MS (ESI) 291.2 (M+H)$^+$.

Example 101

Preparation of 3-(4-methoxy-anilino)-5-(2-fluoro-benzylthio)-1,2,4-triazole

Following the procedure of Example 1(a)-1(d), except p-methoxyphenyl isothiocyanate was substituted for phenylisothiocyanate in step 1(a) and 2-fluorobenzyl bromide was substituted for benzyl bromide in step 1(d), the title compound was prepared as a white solid. MS (ESI) 331.2 (M+H)$^+$.

Example 102

Preparation of 3-(4-methoxy-anilino)-5-(5-methyl-isoxazol-3-ylmethylthio)-1,2,4-triazole Following the procedure of Example 1(a)-1(d), except p-methoxyphenyl isothiocyanate was substituted for phenylisothiocyanate in step 1(a) and 3-(chloromethyl)-5-methylisoxazole was substituted for benzyl bromide in step 1(d), the title compound was prepared as a white solid. MS (ESI) 318.2 (M+H)$^+$.

Example 103

Preparation of 3-(4-methoxy-anilino)-5-(2-methyl-benzylthio)-1,2,4-triazole

Following the procedure of Example 1(a)-1(d), except p-methoxyphenyl isothiocyanate was substituted for phenylisothiocyanate in step 1(a) and 2-methylbenzyl bromide was substituted for benzyl bromide in step 1(d), the title compound was prepared as a white solid. MS (ESI) 327.2 (M+H)$^+$.

Example 104

Preparation of 3-(4-methoxy-anilino)-5-(3,4-difluoro-benzylthio)-1,2,4-triazole

Following the procedure of Example 1(a)-1(d), except p-methoxyphenyl isothiocyanate was substituted for phenylisothiocyanate in step 1(a) and 3,4-difluorobenzyl bromide was substituted for benzyl bromide in step 1(d), the title compound was prepared as a white solid. MS (ESI) 349.0 (M+H)$^+$.

Example 105

Preparation of 3-(4-methoxy-anilino)-5-(2-methoxy-benzylthio)-1,2,4-triazole

Following the procedure of Example 1(a)-1(d), except p-methoxyphenyl isothiocyanate was substituted for phenylisothiocyanate in step 1(a) and 2-methoxybenzyl bromide was substituted for benzyl bromide in step 1(d), the title compound was prepared as a white solid. MS (ESI) 343.0 (M+H)$^+$.

Example 106

Preparation of 3-(4-methoxy-anilino)-5-(2-methyl-thiazol-4-ylmethylthio)-1,2,4-triazole Following the procedure of Example 1(a)-1(d), except p-methoxyphenyl isothiocyanate was substituted for phenylisothiocyanate in step 1(a) and 4-chloromethyl-2-methylthiazole was substituted for benzyl bromide in step 1(d), the title compound was prepared as a white solid (2%). MS (ESI) 334.2 (M+H)$^+$.

Example 107

Preparation of 3-(4-methoxy-anilino)-5-(pyridin-2-ylmethylthio)-1,2,4-triazole

Following the procedure of Example 1(a)-1(d), except p-methoxyphenyl isothiocyanate was substituted for phenylisothiocyanate in step 1(a) and 2-(chloromethyl)pyridine was substituted for benzyl bromide in step 1(d), the title compound was prepared as a white solid. MS (ESI) 314.2 (M+H)$^+$.

Example 108

Preparation of 3-(4-methoxy-anilino)-5-(3-chloro-thiophen-2-ylmethylthio)-1,2,4-triazole Following the procedure of Example 1(a)-1(d), except p-methoxyphenyl isothiocyanate was substituted for phenylisothiocyanate in step 1(a) and 2-chloromethyl-3-chlorothiophene (Chauhan, P. M. S.; Jenkins, G.; Walker, S. M.; Storr, R. C. *Tetrahedron Lett.* 1988, 29(1), 117) was substituted for benzyl bromide in step 1(d), the title compound was prepared as a white solid. MS (ESI) 353.2 (M+H)$^+$.

Example 109

Preparation of 3-(4-methoxy-anilino)-5-(5-chloro-thiophen-2-ylmethylthio)-1,2,4-triazole Following the procedure of Example 1(a)-1(d), except p-methoxyphenyl isothiocyanate was substituted for phenylisothiocyanate in step 1(a) and 2-chloromethyl-5-chlorothiophene was substituted for benzyl bromide in step 1(d), the title compound was prepared as a white solid. MS (ESI) 353.0 (M+H)$^+$.

Example 110

Preparation of 4-(5-benzylthio-1H-[1,2,4]triazol-3-ylamino)-benzoic acid methyl ester Following the procedure of Example 1(a)-1(d), except p-methoxycarbonylphenyl isothiocyanate was substituted for phenylisothiocyanate in step 1(a), the title compound was prepared as a white solid. MS (ESI) 341.0 (M+H)$^+$.

Example 111

Preparation of 4-(5-(cyclohexylmethylthio)-1H-[1,2,4]triazol-3-ylamino)-benzoic Acid Methyl Ester Following the procedure of Example 1(a)-1(d), except p-methoxycarbonylphenyl isothiocyanate was substituted for phenylisothiocyanate in step 1(a) and bromomethylcyclohexane was substituted for benzyl bromide in step 1(d), the title compound was prepared as a white solid. MS (ESI) 347.2 (M+H)$^+$.

Example 112

Preparation of 4-(5-(pyridin-4-ylmethylthio)-1H-[1,2,4]triazol-3-ylamino)-benzoic Acid Methyl Ester Following the procedure of Example 1(a)-1(d), except p-methoxycarbonylphenyl isothiocyanate was substituted for phenylisothiocyanate in step 1(a) and 4-(chloromethyl)pyridine was substituted for benzyl bromide in step 1(d), the title compound was prepared as a white solid. MS (ESI) 342.2 (M+H)$^+$.

Example 113

Preparation of 4-(5-(2-methyl-2-butenylthio)-1H-[1,2,4]triazol-3-ylamino)-benzoic Acid Methyl Ester Following the procedure of Example 1(a)-1(d), except p-methoxycarbonylphenyl isothiocyanate was substituted for phenylisothiocyanate in step 1(a) and 1-bromo-3-methylbut-2-ene was substituted for benzyl bromide in step 1(d), the title compound was prepared as a white solid. MS (ESI) 319.0 (M+H)$^+$.

Example 114

Preparation of 4-(5-(2-fluoro-benzylthio)-1H-[1,2,4]triazol-3-ylamino)-benzoic Acid Methyl Ester Following the procedure of Example 1(a)-1(d), except p-methoxycarbonylphenyl isothiocyanate was substituted for phenylisothiocyanate in step 1(a) and 2-fluorobenzyl bromide was substituted for benzyl bromide in step 1(d), the title compound was prepared as a white solid. MS (ESI) 359.2 (M+H)$^+$.

Example 115

Preparation of 4-(5-(5-methyl-isoxazol-3-ylmethylthio)-1H-[1,2,4]triazol-3-ylamino)-benzoic Acid Methyl Ester Following the procedure of Example 1(a)-1(d), except p-methoxycarbonylphenyl isothiocyanate was substituted for phenylisothiocyanate in step 1(a) and 3-(chloromethyl)-5-methylisoxazole was substituted for benzyl bromide in step 1(d), the title compound was prepared as a white solid. MS (ESI) 346.0 (M+H)$^+$.

Example 116

Preparation of 4-(5-(2-methyl-benzylthio)-1H-[1,2,4]triazol-3-ylamino)-benzoic Acid Methyl Ester Following the procedure of Example 1(a)-1(d), except p-methoxycarbonylphenyl isothiocyanate was substituted for phenylisothiocyanate in step 1(a) and 2-methylbenzyl bromide was substituted for benzyl bromide in step 1(d), the title compound was prepared as a white solid. MS (ESI) 355.0 (M+H)$^+$.

Example 117

Preparation of 4-(5-(3-methoxy-benzylthio)-1H-[1,2,4]triazol-3-ylamino)-benzoic Acid Methyl Ester Following the procedure of Example 1(a)-1(d), except p-methoxycarbonylphenyl isothiocyanate was substituted for phenylisothiocyanate in step 1(a) and 3-methoxybenzyl chloride was substituted for benzyl bromide in step 1(d), the title compound was prepared as a white solid. MS (ESI) 371.0 (M+H)$^+$.

Example 118

Preparation of 4-(5-(3,4-difluoro-benzylthio)-1H-[1,2,4]triazol-3-ylamino)-benzoic Acid Methyl Ester Following the procedure of Example 1(a)-1(d), except p-methoxycarbonylphenyl isothiocyanate was substituted for phenylisothiocyanate in step 1(a) and 3,4-difluorobenzyl bromide was substituted for benzyl bromide in step 1(d), the title compound was prepared as a white solid. MS (ESI) 377.0 (M+H)$^+$.

Example 119

Preparation of 4-(5-(2-methoxy-benzylthio)-1H-[1,2,4]triazol-3-ylamino)-benzoic Acid Methyl Ester Following the procedure of Example 1(a)-1(d), except p-methoxycarbonylphenyl isothiocyanate was substituted for phenylisothiocyanate in step 1(a) and 2-methoxybenzyl chloride was substituted for benzyl bromide in step 1(d), the title compound was prepared as a white solid. MS (ESI) 371.0 (M+H)$^+$.

Example 120

Preparation of 4-(5-(2-methyl-thiazol-4-ylmethylthio)-1H-[1,2,4]triazol-3-ylamino)-benzoic Acid Methyl Ester Following the procedure of Example 1(a)-1(d), except p-methoxycarbonylphenyl isothiocyanate was substituted for phenylisothiocyanate in step 1(a) and 4-chloromethyl-2-methylthiazole was substituted for benzyl bromide in step 1(d), the title compound was prepared as a white solid. MS (ESI) 362.0 $(M+H)^+$.

Example 121

Preparation of 4-(5-(pyridin-2-ylmethylthio)-1H-[1,2,4]triazol-3-ylamino)-benzoic Acid Methyl Ester Following the procedure of Example 1(a)-1(d), except p-methoxycarbonylphenyl isothiocyanate was substituted for phenylisothiocyanate in step 1(a) and 2-(chloromethyl)pyridine was substituted for benzyl bromide in step 1(d), the title compound was prepared as a white solid. MS (ESI) 342.2 $(M+H)^+$.

Example 122

Preparation of 3-(3,4-dimethoxy-anilino)-5-benzylthio-1,2,4-triazole

Following the procedure of Example 1(a)-1(d), except 3,4-dimethoxyphenyl isothiocyanate was substituted for phenylisothiocyanate in step 1(a), the title compound was prepared as a white solid. MS (ESI) 343.0 $(M+H)^+$.

Example 123

Preparation of 3-(3,4-dimethoxy-anilino)-5-(3-methoxy-benzylthio)-1,2,4-triazole Following the procedure of Example 1(a)-1(d), except 3,4-dimethoxyphenyl isothiocyanate was substituted for phenylisothiocyanate in step 1(a) and 3-methoxybenzyl chloride was substituted for benzyl bromide in step 1(d), the title compound was prepared as a white solid. MS (ESI) 373.2 $(M+H)^+$.

Example 124

Preparation of 3-(3,4-dimethoxy-anilino)-5-(cyclohexylmethylthio)-1,2,4-triazole Following the procedure of Example 1(a)-1(d), except 3,4-dimethoxyphenyl isothiocyanate was substituted for phenylisothiocyanate in step 1(a) and bromomethylcyclohexane was substituted for benzyl bromide in step 1(d), the title compound was prepared as a white solid. MS (ESI) 349.2 $(M+H)^+$.

Example 125

Preparation of 3-(3,4-dimethoxy-anilino)-5-(pyridin-4-ylmethylthio)-1,2,4-triazole Following the procedure of Example 1(a)-1(d), except 3,4-dimethoxyphenyl isothiocyanate was substituted for phenylisothiocyanate in step 1(a) and 4-(chloromethyl)pyridine was substituted for benzyl bromide in step 1(d), the title compound was prepared as a white solid. MS (ESI) 344.2 $(M+H)^+$.

Example 126

Preparation of 3-(3,4-dimethoxy-anilino)-5-(2-methyl-2-butenylthio)-1,2,4-triazole Following the procedure of Example 1(a)-1(d), except 3,4-dimethoxyphenyl isothiocyanate was substituted for phenylisothiocyanate in step 1(a) and 1-bromo-3-methylbut-2-ene was substituted for benzyl bromide in step 1(d), the title compound was prepared as a white solid. MS (ESI) 321.2 $(M+H)^+$.

Example 127

Preparation of 3-(3,4-dimethoxy-anilino)-5-(2-fluoro-benzmlthio)-1,2,4-triazole

Following the procedure of Example 1(a)-1(d),), except 3,4-dimethoxyphenyl isothiocyanate was substituted for phenylisothiocyanate in step 1(a) and 2-fluorobenzyl bromide was substituted for benzyl bromide in step 1(d), the title compound was prepared as a white solid. MS (ESI) 361.2 $(M+H)^+$.

Example 128

Preparation of 3-(3,4-dimethoxy-anilino)-5-(5-methyl-isoxazol-3-ylmethylthio)-1,2,4-triazole Following the procedure of Example 1(a)-1(d), except 3,4-dimethoxyphenyl isothiocyanate was substituted for phenylisothiocyanate in step 1(a) and 3-(chloromethyl)-5-methylisoxazole was substituted for benzyl bromide in step 1(d), the title compound was prepared as a white solid. MS (ESI) 348.2 $(M+H)^+$.

Example 129

Preparation of 3-(3,4-dimethoxy-anilino)-5-(2-methyl-benzylthio)-1,2,4-triazole

Following the procedure of Example 1(a)-1(d), except 3,4-dimethoxyphenyl isothiocyanate was substituted for phenylisothiocyanate in step 1(a) and 2-methylbenzyl bromide was substituted for benzyl bromide in step 1(d), the title compound was prepared as a white solid. MS (ESI) 357.2 $(M+H)^+$.

Example 130

Preparation of 3-(3,4-dimethoxy-anilino)-5-(3,4-difluoro-benzylthio)-1,2,4-triazole Following the procedure of Example 1(a)-1(d), except 3,4-dimethoxyphenyl isothiocyanate was substituted for phenylisothiocyanate in step 1(a) and 3,4-difluorobenzyl bromide was substituted for benzyl bromide in step 1(d), the title compound was prepared as a white solid. MS (ESI) 379.0 $(M+H)^+$.

Example 131

Preparation of 3-(3,4-dimethoxy-anilino)-5-(2-methoxy-benzylthio)-1,2,4-triazole Following the procedure of Example 1(a)-1(d), except 3,4-dimethoxyphenyl isothiocyanate was substituted for phenylisothiocyanate in step 1(a) and 2-methoxybenzyl bromide was substituted for benzyl bromide in step 1(d), the title compound was prepared as a white solid. MS (ESI) 373.0 (M+H)$^+$.

Example 132

Preparation of 3-(3,4-dimethoxy-anilino)-5-(2-methyl-thiazol-4-ylmethylthio-1,2,4-triazole Following the procedure of Example 1(a)-1(d), except 3,4-dimethoxyphenyl isothiocyanate was substituted for phenylisothiocyanate in step 1(a) and 4-chloromethyl-2-methylthiazole was substituted for benzyl bromide in step 1(d), the title compound was prepared as a white solid. MS (ESI) 364.2 (M+H)$^+$.

Example 133

Preparation of 3-(3,4-dimethoxy-anilino)-5-(pyridin-2-ylmethylthio)-1,2,4-triazole Following the procedure of Example 1(a)-1(d), except 3,4-dimethoxyphenyl isothiocyanate was substituted for phenylisothiocyanate in step 1(a) and 2-(chloromethyl)pyridine was substituted for benzyl bromide in step 1(d), the title compound was prepared as a white solid. MS (ESI) 344.0 (M+H)$^+$.

Example 134

Preparation of 3-(3,4-dimethoxy-anilino)-5-(thiophen-2-ylmethylthio)-1,2,4-triazole Following the procedure of Example 1(a)-1(d), except 3,4-dimethoxyphenyl isothiocyanate was substituted for phenylisothiocyanate in step 1(a) and 2-chloromethylthiophene was substituted for benzyl bromide in step 1(d), the title compound was prepared as a white solid. MS (ESI) 349.0 (M+H)$^+$.

Example 135

Preparation of 3-(2-phenyl-anilino)-5-benzylthio-1,2,4-triazole

Following the procedure of Example 1(a)-1(d), except 2-phenyl-phenyl isothiocyanate was substituted for phenylisothiocyanate in step 1(a) the title compound was prepared as a white solid. MS (ESI) 359.2 (M+H)$^+$.

Example 136

Preparation of 3-(2-phenyl-anilino)-5-(3-methoxy-benzylthio)-1,2,4-triazole

Following the procedure of Example 1(a)-1(d), except 2-phenyl-phenyl isothiocyanate was substituted for phenylisothiocyanate in step 1(a) and 3-methoxyphenyl chloride was substituted for benzyl bromide in step 1(d), the title compound was prepared as a white solid. MS (ESI) 389.0 (M+H)$^+$.

Example 137

Preparation of 3-(2-phenyl-anilino)-5-(cyclohexylmethylthio)-1,2,4-triazole

Following the procedure of Example 1(a)-1(d), except 2-phenyl-phenyl isothiocyanate was substituted for phenylisothiocyanate in step 1(a) and bromomethylcyclohexane was substituted for benzyl bromide in step 1(d), the title compound was prepared as a white solid. MS (ESI) 365.2 (M+H)$^+$.

Example 138

Preparation of 3-(2-phenyl-anilino)-5-(pyridin-4-ylmethylthio)-1,2,4-triazole

Following the procedure of Example 1(a)-1(d except 2-phenyl-phenyl isothiocyanate was substituted for phenylisothiocyanate in step 1(a) and 4-(chloromethyl)pyridine was substituted for benzyl bromide in step 1(d), the title compound was prepared as a white solid. MS (ESI) 360.2 (M+H)$^+$.

Example 139

Preparation of 3-(2-phenyl-anilino)-5-(2-methyl-2-butenylthio)-1,2,4-triazole

Following the procedure of Example 1(a)-1(d), except 2-phenyl-phenyl isothiocyanate was substituted for phenylisothiocyanate in step 1(a) and 1-bromo-3-methylbut-2-ene was substituted for benzyl bromide in step 1(d), the title compound was prepared as a white solid. MS (ESI) 337.2 (M+H)$^+$.

Example 140

Preparation of 3-(2-phenyl-anilino)-5-(2-fluoro-benzylthio)-1,2,4-triazole

Following the procedure of Example 1(a)-1(d), except 2-phenyl-phenyl isothiocyanate was substituted for phenylisothiocyanate in step 1(a) and 2-fluorobenzyl bromide was substituted for benzyl bromide in step 1(d), the title compound was prepared as a white solid. MS (ESI) 376.8 (M)$^+$.

Example 141

Preparation of 3-(2-phenyl-anilino)-5-(5-methyl-isoxazol-3-ylmethylthio)-1,2,4-triazole Following the procedure of Example 1(a)-1(d), except 2-phenyl-phenyl isothiocyanate was substituted for phenylisothiocyanate in step 1(a) and 3-(chloromethyl)-5-methyl-isoxazole was substituted for benzyl bromide in step 1(d), the title compound was prepared as a white solid. MS (ESI) 364.0 (M+H)$^+$.

Example 142

Preparation of 3-(2-phenyl-anilino)-5-(2-methyl-benzylthio)-1,2,4-triazole

Following the procedure of Example 1(a)-1(d), except 2-phenyl-phenyl isothiocyanate was substituted for phenylisothiocyanate in step 1(a) and 2-methylbenzyl bromide was substituted for benzyl bromide in step 1(d), the title compound was prepared as a white solid. MS (ESI) 373.0 $(M+H)^+$.

Example 143

Preparation of 3-(2-phenyl-anilino)-5-(3,4-difluoro-benzylthio)-1,2,4-triazole

Following the procedure of Example 1(a)-1(d), except 2-phenyl-phenyl isothiocyanate was substituted for phenylisothiocyanate in step 1(a) and 3,4-difluorobenzyl bromide was substituted for benzyl bromide in step 1(d), the title compound was prepared as a white solid. MS (ESI) 395.0 $(M+H)^+$.

Example 144

Preparation of 3-(2-phenyl-anilino)-5-(2-methoxy-benzylthio)-1,2,4-triazole

Following the procedure of Example 1(a)-1(d), except 2-phenyl-phenyl isothiocyanate was substituted for phenylisothiocyanate in step 1(a) and 2-methoxybenzyl bromide was substituted for benzyl bromide in step 1(d), the title compound was prepared as a white solid. MS (ESI) 389.2 $(M+H)^+$.

Example 145

Preparation of 3-(2-phenyl-anilino)-5-(2-methyl-thiazol-4-ylmethylthio)-1,2,4-triazole Following the procedure of Example 1(a)-1(d), except 2-phenyl-phenyl isothiocyanate was substituted for phenylisothiocyanate in step 1(a) and 4-chloromethyl-2-methylthiazole was substituted for benzyl bromide in step 1(d), the title compound was prepared as a white solid. MS (ESI) 380.0 $(M+H)^+$.

Example 146

Preparation of 3-(2-phenyl-anilino)-5-(thiophen-2-ylmethylthio)-1,2,4-triazole

Following the procedure of Example 1(a)-1(d), except 2-phenyl-phenyl isothiocyanate was substituted for phenylisothiocyanate in step 1(a) and 2-chloromethylthiophene was substituted for benzyl bromide in step 1(d), the title compound was prepared as a white solid. MS (ESI) 365.2 $(M+H)^+$.

Example 147

Preparation of [5-(benzylthio)-1H-[1,2,4]triazol-3-yl]-pyridin-3-yl-amine

Following the procedure of Example 1(a)-1(d), except 3-pyridyl isothiocyanate was substituted for phenylisothiocyanate in step 1(a) the title compound was prepared as a white solid. MS (ESI) 284.2 $(M+H)^+$.

Example 148

Preparation of [5-(3-methoxybenzylthio)-1H-[1,2,4]triazol-3-yl]-pyridin-3-yl-amine Following the procedure of Example 1(a)-1(d), except 3-pyridyl isothiocyanate was substituted for phenylisothiocyanate in step 1(a) and 3-methoxyphenyl chloride was substituted for benzyl bromide in step 1(d), the title compound was prepared as a white solid. MS (ESI) 314.2 $(M+H)^+$.

Example 149

Preparation of [5-(cyclohexylmethylthio)-1H-[1,2,4]triazol-3-yl]-pyridin-3-yl-amine Following the procedure of Example 1(a)-1(d), except 3-pyridyl isothiocyanate was substituted for phenylisothiocyanate in step 1(a) and bromomethylcyclohexane was substituted for benzyl bromide in step 1(d), the title compound was prepared as a white solid. MS (ESI) 290.2 $(M+H)^+$.

Example 150

Preparation of [5-(pyridin-4-ylmethylthio)-1H-[1,2,4]triazol-3-yl]-pyridin-3-yl-amine Following the procedure of Example 1(a)-1(d), except 3-pyridyl isothiocyanate was substituted for phenylisothiocyanate in step 1(a) and 4-(chloromethyl)pyridine was substituted for benzyl bromide in step 1(d), the title compound was prepared as a white solid. MS (ESI) 285.2 $(M+H)^+$.

Example 151

Preparation of [5-(2-methyl-2-butenylthio)-1H-[1,2,4]triazol-3-yl]-pyridin-3-yl-amine Following the procedure of Example 1(a)-1(d), except 3-pyridyl isothiocyanate was substituted for phenylisothiocyanate in step 1(a) and 1-bromo-3-methylbut-2-ene was substituted for benzyl bromide in step 1(d), the title compound was prepared as a white solid. MS (ESI) 262.0 $(M+H)^+$.

Example 152

Preparation of [5-(2-fluoro-benzylthio)-1H-[1,2,4]triazol-3-yl-]pyridin-3-yl-amine Following the procedure of Example 1(a)-1(d), except 3-pyridyl isothiocyanate was substituted for phenylisothiocyanate in step 1(a) and 2fluorobenzyl bromide was substituted for benzyl bromide in step 1(d), the title compound was prepared as a white solid. MS (ESI) 302.2 $(M+H)^+$.

Example 153

Preparation of [5-(5-methyl-isoxazol-3-ylmethylthio)-1H-[1,2,4]triazol-3-yl]-pyridin-3-yl-amine Following the procedure of Example 1(a)-1(d), except 3-pyridyl isothiocyanate was substituted for phenylisothiocyanate in step 1(a) and 3-(chloromethyl)-5-methylisoxazole was substituted for benzyl bromide in step 1(d), the title compound was prepared as a white solid. MS (ESI) 289.0 (M+H)$^+$.

Example 154

Preparation of [5-(2-methyl-benzylthio)-1H-[1,2,4]triazol-3-yl]-pyridin-3-yl-amine Following the procedure of Example 1(a)-1(d), except 3-pyridyl isothiocyanate was substituted for phenylisothiocyanate in step 1(a) and 2-methylbenzyl bromide was substituted for benzyl bromide in step 1(d), the title compound was prepared as a white solid. MS (ESI) 298.2 (M+H)$^+$.

Example 155

Preparation of [5-(3,4-difluoro-benzylthio)-1H-[1,2,4]triazol-3-yl]-pyridin-3-yl-amine Following the procedure of Example 1(a)-1(d), except 3-pyridyl isothiocyanate was substituted for phenylisothiocyanate in step 1(a) and 3,4-difluorobenzyl bromide was substituted for benzyl bromide in step 1(d), the title compound was prepared as a white solid. MS (ESI) 320.2 (M+H)$^+$.

Example 156

Preparation of [5-(2-methoxy-benzylthio)-1H-[1,2,4]triazol-3-yl]-pyridin-3-yl-amine Following the procedure of Example 1(a)-1(d), except 3-pyridyl isothiocyanate was substituted for phenylisothiocyanate in step 1(a) and 2-methoxybenzyl chloride was substituted for benzyl bromide in step 1(d), the title compound was prepared as a white solid. MS (ESI) 314.2 (M+H)$^+$.

Example 157

Preparation of [5-(pyridin-2-ylmethylthio)-1H-[1,2,4]triazol-3-yl]-pyridin-3-yl-amine Following the procedure of Example 1(a)-1(d), except 3-pyridyl isothiocyanate was substituted for phenylisothiocyanate in step 1(a) and 2-(chloromethyl)pyridine was substituted for benzyl bromide in step 1(d), the title compound was prepared as a white solid. MS (ESI) 285.2 (M+H)$^+$.

Example 158

Preparation of [5-(2-methyl-thiazol-4-ylmethylthio)-1H-[1,2,4]triazol-3-yl]-pyridin-3-yl-amine Following the procedure of Example 1(a)-1(d), except 3-pyridyl isothiocyanate was substituted for phenylisothiocyanate in step 1(a) and 4-chloromethyl-2-methylthiazole was substituted for benzyl bromide in step 1(d), the title compound was prepared as a white solid. MS (ESI) 305.2 (M+H)$^+$.

Example 159

Preparation of [5-(thiophen-2-ylmethylthio)-1H-[1,2,4]triazol-3-yl]-pyridin-3-yl-amine Following the procedure of Example 1(a)-1(d), except 3-pyridyl isothiocyanate was substituted for phenylisothiocyanate in step 1(a) and 2-chloromethylthiophene was substituted for benzyl bromide in step 1(d), the title compound was prepared as a white solid. MS (ESI) 290.0 (M+H)$^+$.

Example 160

Preparation of 3-(2-ethyl-anilino)-5-benzylthio-1,2,4-triazole

Following the procedure of Example 1(a)-1(d), except 2-ethylphenyl isothiocyanate was substituted for phenylisothiocyanate in step 1(a) the title compound was prepared as a white solid. MS (ESI) 311.4 (M+H)$^+$.

Example 161

Preparation of 3-(2-ethyl-anilino)-5-(thiophen-2-ylmethylthio)-1,2,4-triazole

Following the procedure of Example 1(a)-1(d), except 2-ethylphenyl isothiocyanate was substituted for phenylisothiocyanate in step 1(a) and 2chloromethylthiophene was substituted for benzyl bromide in step 1(d), the title compound was prepared as a white solid. MS (ESI) 317.2 (M+H)$^+$.

Example 162

Preparation of 3-(2-ethyl-anilino)-5-(4-fluoro-benzylthio)-1,2,4-triazole

Following the procedure of Example 1(a)-1(d), except 2-ethylphenyl isothiocyanate was substituted for phenylisothiocyanate in step 1(a) and 4-fluorobenzyl bromide was substituted for benzyl bromide in step 1(d), the title compound was prepared as a white solid. MS (ESI) 329.2 (M+H)$^+$.

Example 163

Preparation of 3-(2-ethyl-anilino)-5-(3,4-difluoro-benzylthio)-1,2,4-triazole

Following the procedure of Example 1(a)-1(d), except 2-ethylphenyl isothiocyanate was substituted for phenylisothiocyanate in step 1(a) and 3,4-difluorobenzyl bromide was substituted for benzyl bromide in step 1(d), the title compound was prepared as a white solid. MS (ESI) 347.0 (M+H)$^+$.

Example 164

Preparation of 3-(2-ethyl-anilino)-5-(2-methyl-2-butenylthio)-1,2,4-triazole

Following the procedure of Example 1(a)-1(d), except 2-ethylphenyl isothiocyanate was substituted for phenylisothiocyanate in step 1(a) and 1-bromo-3-methylbut-2-ene was substituted for benzyl bromide in step 1(d), the title compound was prepared as a white solid. MS (ESI) 289.0 $(M+H)^+$.

Example 165

Preparation of 3-(2-ethyl-anilino)-5-(2-fluoro-benzylthio)-1,2,4-triazole

Following the procedure of Example 1(a)-1(d), except 2-ethylphenyl isothiocyanate was substituted for phenylisothiocyanate in step 1(a) and 2-fluorobenzyl bromide was substituted for benzyl bromide in step 1(d), the title compound was prepared as a white solid. MS (ESI) 329.2 $(M+H)^+$.

Example 166

Preparation of 3-(2-ethyl-anilino)-5-(2-methyl-benzylthio)-1,2,4-triazole

Following the procedure of Example 1(a)-1(d), except 2-ethylphenyl isothiocyanate was substituted for phenylisothiocyanate in step 1(a) and 2-methylbenzyl bromide was substituted for benzyl bromide in step 1(d), the title compound was prepared as a white solid. MS (ESI) 325.2 $(M+H)^+$.

Example 167

Preparation of 3-(2-ethyl-anilino)-5-(2-chloro-benzylthio)-1,2,4-triazole

Following the procedure of Example 1(a)-1(d), except 2-ethylphenyl isothiocyanate was substituted for phenylisothiocyanate in step 1(a) and 2-chlorobenzyl bromide was substituted for benzyl bromide in step 1(d), the title compound was prepared as a white solid. MS (ESI) 345.0 $(M+H)^+$.

Example 168

Preparation of 3-(2-ethyl-anilino)-5-(4-methoxy-benzylthio)-1,2,4-triazole

Following the procedure of Example 1(a)-1(d), except 2-ethylphenyl isothiocyanate was substituted for phenylisothiocyanate in step 1(a) and 4-methoxybenzyl chloride was substituted for benzyl bromide in step 1(d), the title compound was prepared as a white solid. MS (ESI) 341.2 $(M+H)^+$.

Example 169

Preparation of 3-(2-ethyl-anilino)-5-(3,4-methylene-dioxy-benzylthio)-1,2,4-triazole Following the procedure of Example 1(a)-1(d), except 2-ethylphenyl isothiocyanate was substituted for phenylisothiocyanate in step 1(a) and 3,4-methylenedioxybenzyl chloride was substituted for benzyl bromide in step 1(d), the title compound was prepared as a white solid. MS (ESI) 355.0 $(M+H)^+$.

Example 170

Preparation of 3-(2-ethyl-anilino)-5-(5-methyl-isoxazol-3-ylmethylthio)-1,2,4-triazole Following the procedure of Example 1(a)-1(d), except 2-ethylphenyl isothiocyanate was substituted for phenylisothiocyanate in step 1(a) and 3-(chloromethyl)-5-methylisoxazole was substituted for benzyl bromide in step 1(d), the title compound was prepared as a white solid. MS (ESI) 316.0 $(M+H)^+$.

Example 171

Preparation of 3-(2-ethyl-anilino)-5-(pyridin-2-ylmethylthio)-1,2,4-triazole

Following the procedure of Example 1(a)-1(d), except 2-ethylphenyl isothiocyanate was substituted for phenylisothiocyanate in step 1(a) and 2-(chloromethyl)pyridine was substituted for benzyl bromide in step 1(d), the title compound was prepared as a white solid. MS (ESI) 312.2 $(M+H)^+$.

Example 172

Preparation of 3-(2-ethyl-anilino)-5-(2-methoxy-benzylthio)-1,2,4-triazole

Following the procedure of Example 1(a)-1(d), except 2-ethylphenyl isothiocyanate was substituted for phenylisothiocyanate in step 1(a) and 2-methoxybenzyl chloride was substituted for benzyl bromide in step 1(d), the title compound was prepared as a white solid. MS (ESI) 341.2 $(M+H)^+$.

Example 173

Preparation of 3-(2-methoxy-anilino)-5-benzylthio-1,2,4-triazole

Following the procedure of Example 1(a)-1(d), except 2-methoxyphenyl isothiocyanate was substituted for phenylisothiocyanate in step 1(a) the title compound was prepared as a white solid. MS (ESI) 313.2 $(M+H)^+$.

Example 174

Preparation of 3-(2-methoxy-anilino)-5-(thiophen-2-ylmethylthio)-1,2,4-triazole

Following the procedure of Example 1(a)-1(d), except 2-methoxyphenyl isothiocyanate was substituted for phenylisothiocyanate in step 1(a) and 2-chloromethylthiophene was substituted for benzyl bromide in step 1(d), the title compound was prepared as a white solid. MS (ESI) 319.0 $(M+H)^+$.

Example 175

Preparation of 3-(2-methoxy-anilino)-5-(4-fluoro-benzylthio)-1,2,4-triazole

Following the procedure of Example 1(a)-1(d), except 2-methoxyphenyl isothiocyanate was substituted for phenylisothiocyanate in step 1(a) and 4-fluorobenzyl bromide was substituted for benzyl bromide in step 1(d), the title compound was prepared as a white solid. MS (ESI) 331.2 (M+H)$^+$.

Example 176

Preparation of 3-(2-methoxy-anilino)-5-(cyclohexyl-methylthio)-1,2,4-triazole

Following the procedure of Example 1(a)-1(d), except 2-methoxyphenyl isothiocyanate was substituted for phenylisothiocyanate in step 1(a) and bromomethylcyclohexane was substituted for benzyl bromide in step 1(d), the title compound was prepared as a white solid. MS (ESI) 319.2 (M+H)$^+$.

Example 177

Preparation of 3-(2-methoxy-anilino)-5-(3,4-difluoro-benzylthio)-1,2,4-triazole

Following the procedure of Example 1(a)-1(d), except 2-methoxyphenyl isothiocyanate was substituted for phenylisothiocyanate in step 1(a) and 3,4-difluorobenzyl bromide was substituted for benzyl bromide in step 1(d), the title compound was prepared as a white solid. MS (ESI) 349.0 (M+H)$^+$.

Example 178

Preparation of 3-(2-methoxy-anilino)-5-(2-methyl-2-butenylthio)-1,2,4-triazole

Following the procedure of Example 1(a)-1(d), except 2-methoxyphenyl isothiocyanate was substituted for phenylisothiocyanate in step 1(a) and 1-bromo-3-methylbut-2-ene was substituted for benzyl bromide in step 1(d), the title compound was prepared as a white solid. MS (ESI) 291.2 (M+H)$^+$.

Example 179

Preparation of 3-(2-methoxy-anilino)-5-(2-fluoro-benzylthio)-1,2,4-triazole

Following the procedure of Example 1(a)-1(d), except 2-methoxyphenyl isothiocyanate was substituted for phenylisothiocyanate in step 1(a) and 2-fluorobenzyl bromide was substituted for benzyl bromide in step 1(d), the title compound was prepared as a white solid. MS (ESI) 331.2 (M+H)$^+$.

Example 180

Preparation of 3-(2-methoxy-anilino)-5-(2-methyl-benzylthio)-1,2,4-triazole

Following the procedure of Example 1(a)-1(d), except 2-methoxyphenyl isothiocyanate was substituted for phenylisothiocyanate in step 1(a) and 2-methylbenzyl bromide was substituted for benzyl bromide in step 1(d), the title compound was prepared as a white solid. MS (ESI) 327.2 (M+H)$^+$.

Example 181

Preparation of 3-(2-methoxy-anilino)-5-(2-chloro-benzylthio)-1,2,4-triazole

Following the procedure of Example 1(a)-1(d), except 2-methoxyphenyl isothiocyanate was substituted for phenylisothiocyanate in step 1(a) and 2-chlorobenzyl bromide was substituted for benzyl bromide in step 1(d), the title compound was prepared as a white solid. MS (ESI) 347.0 (M+H)$^+$.

Example 182

Preparation of 3-(2-methoxy-anilino)-5-(4-methoxy-benzylthio)-1,2,4-triazole

Following the procedure of Example 1(a)-1(d), except 2-methoxyphenyl isothiocyanate was substituted for phenylisothiocyanate in step 1(a) and 4-methoxybenzyl chloride was substituted for benzyl bromide in step 1(d), the title compound was prepared as a white solid. MS (ESI) 343.0 (M+H)$^+$.

Example 183

Preparation of 3-(2-methoxy-anilino)-5-(3,4-methyl-enedioxy-benzylthio)-1,2,4-triazole Following the procedure of Example 1(a)-1(d), except 2-methoxyphenyl isothiocyanate was substituted for phenylisothiocyanate in step 1(a) and 3,4-methylenedioxybenzyl chloride was substituted for benzyl bromide in step 1(d), the title compound was prepared as a white solid. MS (ESI) 357.0 (M+H)$^+$.

Example 184

Preparation of 3-(2-methoxy-anilino)-5-(5-methyl-isoxazol-3-ylmethylthio)-1,2,4-triazole Following the procedure of Example 1(a)-1(d), except 2-methoxyphenyl isothiocyanate was substituted for phenylisothiocyanate in step 1(a) and 3-(chloromethyl)-5-methylisoxazole was substituted for benzyl bromide in step 1(d), the title compound was prepared as a white solid. MS (ESI) 316.0 (M+H)$^+$.

Example 185

Preparation of 3-(2-methoxy-anilino)-5-(pyridin-2-ylmethylthio)-1,2,4-triazole

Following the procedure of Example 1(a)-1(d), except 2-methoxyphenyl isothiocyanate was substituted for phenylisothiocyanate in step 1(a) and 2-(chloromethyl)pyridine was substituted for benzyl bromide in step 1(d), the title compound was prepared as a white solid. MS (ESI) 314.2 (M+H)$^+$.

Example 186

Preparation of 3-(2-methoxy-anilino)-5-(2-methoxy-benzylthio)-1,2,4-triazole

Following the procedure of Example 1(a)-1(d), except 2-methoxyphenyl isothiocyanate was substituted for phenylisothiocyanate in step 1(a) and 2-methoxybenzyl chloride was substituted for benzyl bromide in step 1(d), the title compound was prepared as a white solid (49%). MS (ESI) 343.0 (M+H)+.

Example 187

Preparation of 3-(2-methoxy-anilino)-5-(furan-2-ylmethylthio)-1,2,4-triazole

Following the procedure of Example 1(a)-1(d), except 2-methoxyphenyl isothiocyanate was substituted for phenylisothiocyanate in step 1(a) and 2-chloromethyl-furan (Berry, J. M.; Watson, C. Y.; Whish, W. J. D.; Threadgill, M. D. *J. Chem. Soc. Perkin Trans*. 1 1997, 8, 1147) was substituted for benzyl bromide in step 1(d), the title compound was prepared as a white solid. MS (ESI) 303.2 (M+H)+.

Example 188

Preparation of 3-(2-methoxy-anilino)-5-(3-methyl-thiophen-2-ylmethylthio)-1,2,4-triazole Following the procedure of Example 1(a)-1(d), except 2-methoxyphenyl isothiocyanate was substituted for phenylisothiocyanate in step 1(a) and 2-chloromethyl-3-methyl-thiophene (Chauhan, P. M. S.; Jenkins, G.; Walker, S. M.; Storr, R. C. *Tetrahedron Lett*. 1988, 29(1), 117) was substituted for benzyl bromide in step 1(d), the title compound was prepared as a white solid. MS (ESI) 333.2 (M+H)+.

Example 189

Preparation of 3-(2-methoxy-anilino)-5-(3-chloro-thiophen-2-ylmethylthio)-1,2,4-triazole Following the procedure of Example 1(a)-1(d), except 2-methoxyphenyl isothiocyanate was substituted for phenylisothiocyanate in step 1(a) and 2-chloromethyl-3-chloro-thiophene (Chauhan, P. M. S.; Jenkins, G.; Walker, S. M.; Storr, R. C. *Tetrahedron Lett*. 1988, 29(1), 117) was substituted for benzyl bromide in step 1(d), the title compound was prepared as a white solid. MS (ESI) 353.2 (M+H)+.

Example 190

Preparation of 3-(2-methoxy-anilino)-5-(5-methyl-thiophen-2-ylmethylthio)-1,2,4-triazole Following the procedure of Example 1(a)-1(d), 2-methoxyphenyl isothiocyanate was substituted for phenylisothiocyanate in step 1(a) and 2-chloromethyl-5-methyl-thiophene (Moradpour, A. *J. Chem. Soc. Perkin Trans*. 1, 1993, 1, 7) was substituted for benzyl bromide in step 1(d), the title compound was prepared as a white solid. MS (ESI) 333.2 (M+H)+.

Example 191

Preparation of 3-(2-methoxy-anilino)-5-(5-chloro-thiophen-2-ylmethylthio)-1,2,4-triazole Following the procedure of Example 1(a)-1(d), except 2-methoxyphenyl isothiocyanate was substituted for phenylisothiocyanate in step 1(a) and 2-chloromethyl-5-chloro-thiophene was substituted for benzyl bromide in step 1(d), the title compound was prepared as a white solid. MS (ESI) 353.0 (M+H)+.

Example 192

Preparation of 5-(5-(2-methoxyphenylamino)-4H-[1,2,4]triazol-3-ylsulfanylmethyl)-furan-2-carboxylic Acid Ethyl Ester Following the procedure of Example 1(a)-1(d), except 2-methoxyphenyl isothiocyanate was substituted for phenylisothiocyanate in step 1(a) and 5-chloromethyl-furan-2-carboxylic acid ethyl ester was substituted for benzyl bromide in step 1(d), the title compound was prepared as a white solid. MS (ESI) 375.0 (M+H)+.

Example 193

Preparation of 3-(2-methoxy-anilino)-5-(5-bromo-thiophen-2-ylmethylthio)-1,2,4-triazole Following the procedure of Example 1(a)-1(d), except 2-methoxyphenyl isothiocyanate was substituted for phenylisothiocyanate in step 1(a) and 2-chloromethyl-5-bromo-thiophene (Clapp, R. C.; Clark, J. H; Vaughan, J. R.; English, J. P.; Anderson, G. W. *J. Am. Chem. Soc*. 1947, 60, 1549) was substituted for benzyl bromide in step 1(d), the title compound was prepared as a white solid. MS (ESI) 396.8 (M-H)+.

Example 194

Preparation of 3-(2-methoxy-anilino)-5-(thiophen-3-ylmethylthio)-1,2,4-triazole

Following the procedure of Example 1(a)-1(d), except 2-methoxyphenyl isothiocyanate was substituted for phenylisothiocyanate in step 1(a) and 3-chloromethyl-thiophene (Lamy, J.; Lavit, D.; Buu-Hoi, N. P. *J. Chem. Soc*. 1958, 4202) was substituted for benzyl bromide in step 1(d), the title compound was prepared as a white solid. MS (ESI) 319.0 (M+H)+.

Example 195

Preparation of 3-(2-methoxy-anilino)-5-(furan-3-ylmethylthio)-1,2,4-triazole

Following the procedure of Example 1(a)-1(d), except 2-methoxyphenyl isothiocyanate was substituted for phenylisothiocyanate in step 1(a) and 3-chloromethyl-furan (Arena, G.; Cali, R.; Maccarone, E.; Passerini, A. *J. Chem. Soc. Perkin Trans*. 2 1993, 10, 1941) was substituted for benzyl bromide in step 1(d), the title compound was prepared as a white solid. MS (ESI) 303.2 (M+H)+.

Example 196

Preparation of 3-(2-isopropyl-anilino)-5-benzylthio-1,2,4-triazole

Following the procedure of Example 1(a)-1(d), except 2-isopropylphenyl isothiocyanate was substituted for phenylisothiocyanate in step 1(a) the title compound was prepared as a white solid. MS (ESI) 325.2 (M+H)$^+$.

Example 197

Preparation of 3-(2-isopropyl-anilino)-5-(thiophen-2-ylmethylthio)-1,2,4-triazole Following the procedure of Example 1(a)-1(d), except 2-isopropylphenyl isothiocyanate was substituted for phenylisothiocyanate in step 1(a) and 2-chloromethylthiophene was substituted for benzyl bromide in step 1(d), the title compound was prepared as a white solid. MS (ESI) 331.2 (M+H)$^+$.

Example 198

Preparation of 3-(2-isopropyl-anilino)-5-(4-fluoro-benzylthio)-1,2,4-triazole

Following the procedure of Example 1(a)-1(d), except 2-isopropylphenyl isothiocyanate was substituted for phenylisothiocyanate in step 1(a) and 4-fluorobenzyl bromide was substituted for benzyl bromide in step 1(d), the title compound was prepared as a white solid. MS (ESI) 343.0 (M+H)$^+$.

Example 199

Preparation of 3-(2-isopropyl-anilino)-5-(cyclohexylmethylthio)-1,2,4-triazole

Following the procedure of Example 1(a)-1(d), except 2-isopropylphenyl isothiocyanate was substituted for phenylisothiocyanate in step 1(a) and bromomethylcyclohexane was substituted for benzyl bromide in step 1(d), the title compound was prepared as a white solid. MS (ESI) 331.2 (M+H)$^+$.

Example 200

Preparation of 3-(2-isoipropyl-anilino)-5-(3,4-difluoro-benzylthio)-1,2,4-triazole Following the procedure of Example 1(a)-1(d), except 2-isopropylphenyl isothiocyanate was substituted for phenylisothiocyanate in step 1(a) and 3,4-difluorobenzyl bromide was substituted for benzyl bromide in step 1(d), the title compound was prepared as a white solid. MS (ESI) 361.2 (M+H)$^+$.

Example 201

Preparation of 3-(2-isopropyl-anilino)-5-(2-methyl-2-butenylthio)-1,2,4-triazole Following the procedure of Example 1(a)-1(d), except 2-isopropylphenyl isothiocyanate was substituted for phenylisothiocyanate in step 1(a) and 1-bromo-3-methylbut-2-ene was substituted for benzyl bromide in step 1(d), the title compound was prepared as a white solid. MS (ESI) 303.2 (M+H)$^+$.

Example 202

Preparation of 3-(2-isopropyl-anilino)-5-(2-fluoro-benzylthio)-1,2,4-triazole

Following the procedure of Example 1(a)-1(d), except 2-isopropylphenyl isothiocyanate was substituted for phenylisothiocyanate in step 1(a) and 2-fluorobenzyl bromide was substituted for benzyl bromide in step 1(d), the title compound was prepared as a white solid. MS (ESI) 343.0 (M+H)$^+$.

Example 203

Preparation of 3-(2-isopropyl-anilino)-5-(2-methyl-benzylthio)-1,2,4-triazole

Following the procedure of Example 1(a)-1(d), except 2-isopropylphenyl isothiocyanate was substituted for phenylisothiocyanate in step 1(a) and 2-methylbenzyl bromide was substituted for benzyl bromide in step 1(d), the title compound was prepared as a white solid. MS (ESI) 339.2 (M+H)$^+$.

Example 204

Preparation of 3-(2-isoipropyl-anilino)-5-(2-chloro-benzylthio)-1,2,4-triazole

Following the procedure of Example 1(a)-1(d), except 2-isopropylphenyl isothiocyanate was substituted for phenylisothiocyanate in step 1(a) and 2-chlorobenzyl bromide was substituted for benzyl bromide in step 1(d), the title compound was prepared as a white solid. MS (ESI) 359.2 (M+H)$^+$.

Example 205

Preparation of 3-(2-isopropyl-anilino)-5-(4-methoxy-benzylthio)-1,2,4-triazole

Following the procedure of Example 1(a)-1(d), except 2-isopropylphenyl isothiocyanate was substituted for phenylisothiocyanate in step 1(a) and 4-methoxybenzyl chloride was substituted for benzyl bromide in step 1(d), the title compound was prepared as a white solid. MS (ESI) 355.2 (M+H)$^+$.

Example 206

Preparation of 3-(2-isopropyl-anilino)-5-(3,4-methylenedioxy-benzylthio)-1,2,4-triazole Following the procedure of Example 1(a)-1(d), except 2-isopropylphenyl isothiocyanate was substituted for phenylisothiocyanate in step 1(a) and 3,4-methylenedioxybenzyl chloride was substituted for benzyl bromide in step 1(d), the title compound was prepared as a white solid. MS (ESI) 369.2 (M+H)$^+$.

Example 207

Preparation of 3-(2-isopropyl-anilino)-5-(5-methyl-isoxazol-3-ylmethylthio)-1,2,4-triazole Following the procedure of Example 1(a)-1(d), except 2-isopropylisothiocyanate was substituted for phenylisothiocyanate in step 1(a) and 3-(chloromethyl)-5-methylisoxazole was substituted for benzyl bromide in step 1(d), the title compound was prepared as a white solid. MS (ESI) 330.2 (M+H)$^+$.

Example 208

Preparation of 3-(2-isopropyl-anilino)-5-(pyridin-2-ylmethylthio)-1,2,4-triazole Following the procedure of Example 1(a)-1(d), except 2-isopropylphenyl isothiocyanate was substituted for phenylisothiocyanate in step 1(a) and 2-(chloromethyl)pyridine was substituted for benzyl bromide in step 1(d), the title compound was prepared as a white solid. MS (ESI) 326.2 (M+H)$^+$.

Example 209

Preparation of 3-(2-isopropyl-anilino)-5-(2-methoxy-benzylthio)-1,2,4-triazole

Following the procedure of Example 1(a)-1(d), except 2-isopropylphenyl isothiocyanate was substituted for phenylisothiocyanate in step 1(a) and 2-methoxybenzyl chloride was substituted for benzyl bromide in step 1(d), the title compound was prepared as a white solid. MS (ESI) 355.2 (M+H)$^+$.

Example 210

Preparation of 3-(2-isopropyl-anilino)-5-(furan-2-ylmethylthio)-1,2,4-triazole

Following the procedure of Example 1(a)-1(d), except 2-isopropylphenyl isothiocyanate was substituted for phenylisothiocyanate in step 1(a) and 2-chloromethyl-furan (Berry, J. M.; Watson, C. Y.; Whish, W. J. D.; Threadgill, M. D. *J. Chem. Soc. Perkin Trans.* 1 1997, 8, 1147) was substituted for benzyl bromide in step 1(d), the title compound was prepared as a white solid. MS (ESI) 315.2 (M+H)$^+$.

Example 211

Preparation of 3-(2-isopropyl-anilino)-5-(3-methyl-thiophen-2-ylmethylthio)-1,2,4-triazole Following the procedure of Example 1(a)-1(d), except 2-isopropylphenyl isothiocyanate was substituted for phenylisothiocyanate in step 1(a) and 2-chloromethyl-3-methyl-thiophene (Chauhan, P. M. S.; Jenkins, G.; Walker, S. M.; Storr, R. C. *Tetrahedron Lett.* 1988, 29(1), 117) was substituted for benzyl bromide in step 1(d), the title compound was prepared as a white solid. MS (ESI) 345.2 (M+H)$^+$.

Example 212

Preparation of 3-(2-isopropyl-anilino)-5-(3-chloro-thiophen-2-ylmethylthio)-1,2,4-triazole Following the procedure of Example 1(a)-1(d), except 2-isopropylphenyl isothiocyanate was substituted for phenylisothiocyanate in step 1(a) and 2-chloromethyl-3-chloro-thiophene (Chauhan, P. M. S.; Jenkins, G.; Walker, S. M.; Storr, R. C. *Tetrahedron Lett.* 1988, 29(1), 117) was substituted for benzyl bromide in step 1(d), the title compound was prepared as a white solid. MS (ESI) 365.2 (M+H)$^+$.

Example 213

Preparation of 3-(2-isopropyl-anilino)-5-(5-methyl-thiophen-2-ylmethylthio)-1,2,4-triazole Following the procedure of Example 1(a)-1(d), except 2-isopropylphenyl isothiocyanate was substituted for phenylisothiocyanate in step 1(a) and 2-chloromethyl-5-methyl-thiophene (Moradpour, A. *J. Chem. Soc. Perkin Trans.* 1, 1993, 1, 7) was substituted for benzyl bromide in step 1(d), the title compound was prepared as a white solid. MS (ESI) 345.2 (M+H)$^+$.

Example 214

Preparation of 3-(2-isopropyl-anilino)-5-(5-chloro-thiophen-2-ylmethylthio)-1,2,4-triazole Following the procedure of Example 1(a)-1(d), except 2-isopropylphenyl isothiocyanate was substituted for phenylisothiocyanate in step 1(a) and 2-chloromethyl-5-chloro-thiophene was substituted for benzyl bromide in step 1(d), the title compound was prepared as a white solid. MS (ESI) 365.2 (M+H)$^+$.

Example 215

Preparation of 5-(5-(2-isopropylphenylamino)-4H-[1,2,4]triazol-3-ylsulfanylmethyl)-furan-2-carboxylic Acid Ethyl Ester Following the procedure of Example 1(a)-1(d), except 2-isopropylphenyl isothiocyanate was substituted for phenylisothiocyanate in step 1(a) and 5-chloromethyl-furan-2-carboxylic acid ethyl ester was substituted for benzyl bromide in step 1(d), the title compound was prepared as a white solid. MS (ESI) 387.2 (M+H)$^+$.

Example 216

Preparation of 5-(5-(2-isopropyl amino)-4H-[1,2,4]triazol-3-ylsulfanylmethyl)-furan-2-carbaldehyde Following the procedure of Example 1(a)-1(d), except 2-isopropylphenyl isothiocyanate was substituted for phenylisothiocyanate in step 1(a) and 5-chloromethyl-furan-2-carbaldehyde (Sanda, K.; Rigal, L.; Delmas, M.; Gaset, A. *Synthesis* 1992, 6, 541) was substituted for benzyl bromide in step 1(d), the title compound was prepared as a white solid. MS (ESI) 343.0 (M+H)$^+$.

Example 217

Preparation of 3-(2-isopropyl-anilino)-5-(thiophen-3-ylmethylthio)-1,2,4-triazole Following the procedure of Example 1(a)-1(d), except 2-isopropylphenyl isothiocyanate was substituted for phenylisothiocyanate in step 1(a) and 3-chloromethyl-thiophene (Lamy, J.; Lavit, D.; Buu-Hoi, N. P. *J. Chem. Soc.* 1958, 4202) was substituted for benzyl bromide in step 1(d), the title compound was prepared as a white solid. MS (ESI) 331.2 (M+H)$^+$.

Example 218

Preparation of 3-(2-isopropyl-anilino)-5-(furan-3-ylmethylthio)-1,2,4-triazole

Following the procedure of Example 1(a)-1(d), except 2-isopropylphenyl isothiocyanate was substituted for phenylisothiocyanate in step 1(a) and 3-chloromethyl-furan (Arena, G.; Cali, R.; Maccarone, E.; Passerini, A. *J. Chem. Soc. Perkin Trans.* 2 1993, 10, 1941) was substituted for benzyl bromide in step 1(d), the title compound was prepared as a white solid. MS (ESI) 315.2 (M+H)$^+$.

Example 219

Preparation of 3-(3-methyl-anilino)-5-benzylthio-1,2,4-triazole

Following the procedure of Example 1(a)-1(d), except m-tolyl isothiocyanate was substituted for phenylisothiocyanate in step 1(a), the title compound was prepared as a white solid. MS (ESI) 297.2 (M+H)$^+$.

Example 220

Preparation of 3-(3-methyl-anilino)-5-(thiophen-2-ylmethylthio)-1,2,4-triazole

Following the procedure of Example 1(a)-1(d), except m-tolyl isothiocyanate was substituted for phenylisothiocyanate in step 1(a) and 2-chloromethylthiophene was substituted for benzyl bromide in step 1(d), the title compound was prepared as a white solid. MS (ESI) 303.2 (M+H)$^+$.

Example 221

Preparation of 3-(3-methyl-anilino)-5-(cyclohexylmethylthio)-1,2,4-triazole

Following the procedure of Example 1(a)-1(d), except m-tolyl isothiocyanate was substituted for phenylisothiocyanate in step 1(a) and bromomethylcyclohexane was substituted for benzyl bromide in step 1(d), the title compound was prepared as a white solid. MS (ESI) 303.2 (M+H)$^+$.

Example 222

Preparation of 3-(3-methyl-anilino)-5-(4-fluoro-benzylthio)-1,2,4-triazole

Following the procedure of Example 1(a)-1(d), except m-tolyl isothiocyanate was substituted for phenylisothiocyanate in step 1(a) and 4-fluorobenzyl bromide was substituted for benzyl bromide in step 1(d), the title compound was prepared as a white solid. MS (ESI) 315.2 (M+H)$^+$.

Example 223

Preparation of 3-(3-methyl-anilino)-5-(2-methyl-2-butenylthio)-1,2,4-triazole

Following the procedure of Example 1(a)-1(d), except m-tolyl isothiocyanate was substituted for phenylisothiocyanate in step 1(a) and 1-bromo-3-methylbut-2-ene was substituted for benzyl bromide in step 1(d), the title compound was prepared as a white solid. MS (ESI) 275.2 (M+H)$^+$.

Example 224

Preparation of 3-(3-methyl-anilino)-5-(2-fluoro-benzylthio)-1,2,4-triazole

Following the procedure of Example 1(a)-1(d), except m-tolyl isothiocyanate was substituted for phenylisothiocyanate in step 1(a) and 2-fluorobenzyl bromide was substituted for benzyl bromide in step 1(d), the title compound was prepared as a white solid. MS (ESI) 315.2 (M+H)$^+$.

Example 225

Preparation of 3-(3-methyl-anilino)-5-(5-methyl-isoxazol-3-ylmethylthio)-1,2,4-triazole Following the procedure of Example 1(a)-1(d), except m-tolyl isothiocyanate was substituted for phenylisothiocyanate in step 1(a) and 3-(chloromethyl)-5-methylisoxazole was substituted for benzyl bromide in step 1(d), the title compound was prepared as a white solid. MS (ESI) 302.2 (M+H)$^+$.

Example 226

Preparation of 3-(3-methyl-anilino)-5-(2-methyl-benzylthio)-1,2,4-triazole

Following the procedure of Example 1(a)-1(d), except m-tolyl isothiocyanate was substituted for phenylisothiocyanate in step 1(a) and 2-methylbenzyl bromide was substituted for benzyl bromide in step 1(d), the title compound was prepared as a white solid. MS (ESI) 311.4 (M+H)$^+$.

Example 227

Preparation of 3-(3-methyl-anilino)-5-(3,4-difluoro-benzylthio)-1,2,4-triazole

Following the procedure of Example 1(a)-1(d), except m-tolyl isothiocyanate was substituted for phenylisothiocyanate in step 1(a) and 3,4-difluorobenzyl bromide was substituted for benzyl bromide in step 1(d), the title compound was prepared as a white solid. MS (ESI) 333.2 (M+H)$^+$.

Example 228

Preparation of 3-(3-methyl-anilino)-5-(2-methoxy-benzylthio)-1,2,4-triazole

Following the procedure of Example 1(a)-1(d), except m-tolyl isothiocyanate was substituted for phenylisothiocy-

Example 229

Preparation of 3-(3-methyl-anilino)-5-(2-chloro-benzylthio)-1,2,4-triazole

Following the procedure of Example 1(a)-1(d), except m-tolyl isothiocyanate was substituted for phenylisothiocyanate in step 1(a) and 2-chlorobenzyl bromide was substituted for benzyl bromide in step 1(d), the title compound was prepared as a white solid. MS (ESI) 331.2 (M+H)+.

Example 230

Preparation of 3-(3-methyl-anilino)-5-(4-methoxy-benzylthio)-1,2,4-triazole

Following the procedure of Example 1(a)-1(d), except m-tolyl isothiocyanate was substituted for phenylisothiocyanate in step 1(a) and 4-methoxybenzyl chloride was substituted for benzyl bromide in step 1(d), the title compound was prepared as a white solid. MS (ESI) 327.2 (M+H)+.

Example 231

Preparation of 3-(3-methyl-anilino)-5-(3,4-methylenedioxy-benzylthio)-1,2,4-triazole Following the procedure of Example 1(a)-1(d), except m-tolyl isothiocyanate was substituted for phenylisothiocyanate in step 1(a) and 3,4-methylenedioxybenzyl chloride was substituted for benzyl bromide in step 1(d), the title compound was prepared as a white solid. MS (ESI) 341.2 (M+H)+.

Example 232

Preparation of 3-(3-methyl-anilino)-5-(pyridin-2-ylmethylthio)-1,2,4-triazole

Following the procedure of Example 1(a)-1(d), except m-tolyl isothiocyanate was substituted for phenylisothiocyanate in step 1(a) and 2-(chloromethyl)pyridine was substituted for benzyl bromide in step 1(d), the title compound was prepared as a white solid. MS (ESI) 298.2 (M+H)+.

Example 233

Preparation of 3-(3-methyl-anilino)-5-(furan-2-ylmethylthio)-1,2,4-triazole

Following the procedure of Example 1(a)-1(d), except 3-m-tolyl isothiocyanate was substituted for phenylisothiocyanate in step 1(a) and 2-chloromethyl-furan (Berry, J. M.; Watson, C. Y.; Whish, W. J. D.; Threadgill, M. D. *J. Chem. Soc. Perkin Trans.* 1 1997, 8, 1147) was substituted for benzyl bromide in step 1(d), the title compound was prepared as a white solid. MS (ESI) 287.2 (M+H)+.

Example 234

Preparation of 3-(3-methyl-anilino)-5-(3-methyl-thiophen-2-ylmethylthio)-1,2,4-triazole Following the procedure of Example 1(a)-1(d), except 3-m-tolyl isothiocyanate was substituted for phenylisothiocyanate in step 1(a) and 2chloromethyl-3-methyl-thiophene (Chauhan, P. M. S.; Jenkins, G.; Walker, S. M.; Storr, R. C. *Tetrahedron Lett.* 1988, 29(1), 117) was substituted for benzyl bromide in step 1(d), the title compound was prepared as a white solid. MS (ESI) 317.2 (M+H)+.

Example 235

Preparation of 3-(3-methyl-anilino)-5-(3-chloro-thiophen-2-ylmethylthio)-1,2,4-triazole Following the procedure of Example 1(a)-1(d), except 3-m-tolyl isothiocyanate was substituted for phenylisothiocyanate in step 1(a) and 2-chloromethyl-3-chloro-thiophene (Chauhan, P. M. S.; Jenkins, G.; Walker, S. M.; Storr, R. C. *Tetrahedron Lett.* 1988, 29(1), 117) was substituted for benzyl bromide in step 1(d), the title compound was prepared as a white solid. MS (ESI) 337.2 (M+H)+.

Example 236

Preparation of 3-(3-methyl-anilino)-5-(5-methyl-thiophen-2-ylmethylthio)-1,2,4-triazole Following the procedure of Example 1(a)-1(d), except 3-m-tolyl isothiocyanate was substituted for phenylisothiocyanate in step 1(a) and 2-chloromethyl-5-methyl-thiophene (Moradpour, A. *J. Chem. Soc. Perkin Trans.* 1, 1993, 1, 7) was substituted for benzyl bromide in step 1(d), the title compound was prepared as a white solid. MS (ESI) 317.2 (M+H)+.

Example 237

Preparation of 3-(3-methyl-anilino)-5-(5-chloro-thiophen-2-ylmethylthio)-1,2,4-triazole Following the procedure of Example 1(a)-1(d), except 3-m-tolyl isothiocyanate was substituted for phenylisothiocyanate in step 1(a) and 2-chloromethyl-5-chloro-thiophene was substituted for benzyl bromide in step 1(d), the title compound was prepared as a white solid. MS (ESI) 337.2 (M+H)+.

Example 238

Preparation of 5-(5-(3-methylphenylamino)-4H-[1,2,4]triazol-3-ylsulfanylmethyl)-furan-2-carboxylic Acid Ethyl Ester Following the procedure of Example 1(a)-1(d), except 3-m-tolyl isothiocyanate was substituted for phenylisothiocyanate in step 1(a) and 5-chloromethyl-furan-2-carboxylic acid ethyl ester was substituted for benzyl bromide in step 1(d), the title compound was prepared as a white solid. MS (ESI) 359.2 (M+H)+.

Example 239

Preparation of 3-(3-methyl-anilino)-5-(5-bromo-thiophen-2-ylmethylthio)-1,2,4-triazole Following the procedure of Example 1(a)-1(d), except 3-m-tolyl isothiocyanate was substituted for phenylisothiocyanate in step 1(a) and 2-chloromethyl-5-bromo-thiophene (Clapp, R. C.; Clark, J. H; Vaughan, J. R.; English, J. P.; Anderson, G. W. *J. Am. Chem. Soc.* 1947, 60, 1549) was substituted for benzyl bromide in step 1(d), the title compound was prepared as a white solid. MS (ESI) 381.0 (M+H)$^+$.

Example 240

Preparation of 5-(5-(3-methylphenylamino)-4H-[1,2,4]triazol-3ylsulfanylmethyl)-furan-2-carbaldehyde Following the procedure of Example 1(a)-1(d), except 3-m-tolyl isothiocyanate was substituted for phenylisothiocyanate in step 1(a) and 5-chloromethyl-furan-2-carbaldehyde (Sanda, K.; Rigal, L.; Delmas, M.; Gaset, A. *Synthesis* 1992, 6, 541) was substituted for benzyl bromide in step 1(d), the title compound was prepared as a white solid. MS (ESI) 315.2 (M+H)$^+$.

Example 241

Preparation of 3-(3-methyl-anilino)-5-(thiophen-3-ylmethylthio)-1,2,4-triazole

Following the procedure of Example 1(a)-1(d), except 3-m-tolyl isothiocyanate was substituted for phenylisothiocyanate in step 1(a) and 3-chloromethyl-thiophene (Lamy, J.; Lavit, D.; Buu-Hoi, N. P. *J. Chem. Soc.* 1958, 4202) was substituted for benzyl bromide in step 1(d), the title compound was prepared as a white solid. MS (ESI) 303.2 (M+H)$^+$.

Example 242

Preparation of 3-(3-methyl-anilino)-5-(furan-3-ylmethylthio)-1,2,4-triazole

Following the procedure of Example 1(a)-1(d), except 3-m-tolyl isothiocyanate was substituted for phenylisothiocyanate in step 1(a) and 3-chloromethyl-furan (Arena, G.; Cali, R.; Maccarone, E.; Passerini, A. *J. Chem. Soc. Perkin Trans.* 2 1993, 10, 1941) was substituted for benzyl bromide in step 1(d), the title compound was prepared as a white solid. MS (ESI) 287.2 (M+H)$^+$.

Example 243

Preparation of 3-(4-n-butyl-anilino)-5-benzylthio-1,2,4-triazole

Following the procedure of Example 1(a)-1(d), except 4-n-butylphenyl isothiocyanate was substituted for phenylisothiocyanate in step 1(a) the title compound was prepared as a white solid. MS (ESI) 339.2 (M+H)$^+$.

Example 244

Preparation of 3-(4-n-butyl-anilino)-5-(thiophen-2-ylmethylthio)-1,2,4-triazole

Following the procedure of Example 1(a)-1(d), except 4-n-butylphenyl isothiocyanate was substituted for phenylisothiocyanate in step 1(a) and 2-chloromethylthiophene was substituted for benzyl bromide in step 1(d), the title compound was prepared as a white solid. MS (ESI) 345.2 (M+H)$^+$.

Example 245

Preparation of 3-(4-n-butyl-anilino)-5-(4-fluoro-benzylthio)-1,2,4-triazole

Following the procedure of Example 1(a)-1(d), except 4-n-butylphenyl isothiocyanate was substituted for phenylisothiocyanate in step 1(a) and 4-fluorobenzyl bromide was substituted for benzyl bromide in step 1(d), the title compound was prepared as a white solid. MS (ESI) 357.2 (M+H)$^+$.

Example 246

Preparation of 3-(4-n-butyl-anilino)-5-(3,4-difluoro-benzylthio)-1,2,4-triazole

Following the procedure of Example 1(a)-1(d), except 4-n-butylphenyl isothiocyanate was substituted for phenylisothiocyanate in step 1(a) and 3,4-difluorobenzyl bromide was substituted for benzyl bromide in step 1(d), the title compound was prepared as a white solid. MS (ESI) 375.2 (M+H)$^+$.

Example 247

Preparation of 3-(4-n-butyl-anilino)-5-(2-methyl-2-butenylthio)-1,2,4-triazole

Following the procedure of Example 1(a)-1(d), except 4-n-butylphenyl isothiocyanate was substituted for phenylisothiocyanate in step 1(a) and 1-bromo-3-methylbut-2-ene was substituted for benzyl bromide in step 1(d), the title compound was prepared as a white solid. MS (ESI) 317.2 (M+H)$^+$.

Example 248

Preparation of 3-(4-n-butyl-anilino)-5-(2-fluoro-benzylthio)-1,2,4-triazole

Following the procedure of Example 1(a)-1(d), except 4-n-butylphenyl isothiocyanate was substituted for phenylisothiocyanate in step 1(a) and 2-fluorobenzyl bromide was substituted for benzyl bromide in step 1(d), the title compound was prepared as a white solid. MS (ESI) 357.2 (M+H)$^+$.

Example 249

Preparation of 3-(4-n-butyl-anilino)-5-(2-methyl-benzylthio)-1,2,4-triazole

Following the procedure of Example 1(a)-1(d), except 4-n-butylphenyl isothiocyanate was substituted for phenylisothiocyanate in step 1(a) and 2-methylbenzyl bromide was substituted for benzyl bromide in step 1(d), the title compound was prepared as a white solid. MS (ESI) 353.2 (M+H)$^+$.

Example 250

Preparation of 3-(4-n-butyl-anilino)-5-(2-chloro-benzylthio)-1,2,4-triazole

Following the procedure of Example 1(a)-1(d), except 4-n-butylphenyl isothiocyanate was substituted for phenylisothiocyanate in step 1(a) and 2-chlorobenzyl bromide was substituted for benzyl bromide in step 1(d), the title compound was prepared as a white solid. MS (ESI) 373.2 (M+H)$^+$.

Example 251

Preparation of 3-(4-n-butyl-anilino)-5-(4-methoxy-benzylthio)-1,2,4-triazole

Following the procedure of Example 1(a)-1(d), except 4-n-butylphenyl isothiocyanate was substituted for phenylisothiocyanate in step 1(a) and 4-methoxybenzyl chloride was substituted for benzyl bromide in step 1(d), the title compound was prepared as a white solid. MS (ESI) 369.2 (M+H)$^+$.

Example 252

Preparation of 3-(4-n-butyl-anilino)-5-(3,4-methyl-enedioxy-benzylthio)-1,2,4-triazole Following the procedure of Example 1(a)-1(d), except 4-n-butylphenyl isothiocyanate was substituted for phenylisothiocyanate in step 1(a) and 3,4-methylenedioxybenzyl chloride was substituted for benzyl bromide in step 1(d), the title compound was prepared as a white solid. MS (ESI) 383.2 (M+H)$^+$.

Example 253

Preparation of 3-(4-n-butyl-anilino)-5-(5-methyl-isoxazol-3-ylmethylthio)-1,2,4-triazole Following the procedure of Example 1(a)-1(d), except 4-n-butylphenyl isothiocyanate was substituted for phenylisothiocyanate in step 1(a) and 3-(chloromethyl)-5-methylisoxazole was substituted for benzyl bromide in step 1(d), the title compound was prepared as a white solid. MS (ESI) 344.2 (M+H)$^+$.

Example 254

Preparation of 3-(4-n-butyl-anilino)-5-(pyridin-2-ylmethylthio)-1,2,4-triazole

Following the procedure of Example 1(a)-1(d), except 4-n-butylphenyl isothiocyanate was substituted for phenylisothiocyanate in step 1(a) and 2-(chloromethyl)pyridine was substituted for benzyl bromide in step 1(d), the title compound was prepared as a white solid. MS (ESI) 340.2 (M+H)$^+$.

Example 255

Preparation of 3-(4-n-butyl-anilino)-5-(2-methoxy-benzylthio)-1,2,4-triazole

Following the procedure of Example 1(a)-1(d), except 4-n-butylphenyl isothiocyanate was substituted for phenylisothiocyanate in step 1(a) and 2-methoxybenzyl chloride was substituted for benzyl bromide in step 1(d), the title compound was prepared as a white solid. MS (ESI) 369.2 (M+H)$^+$.

Example 256

Preparation of 3-(2,4-dimethoxy-anilino)-5-benzylthio-1,2,4-triazole

Following the procedure of Example 1(a)-1(d), except 2,4-dimethoxyphenyl isothiocyanate was substituted for phenylisothiocyanate in step 1(a) the title compound was prepared as a white solid. MS (ESI) 343.0 (M+H)$^+$.

Example 257

Preparation of 3-(2,4-dimethoxy-anilino)-5-(thiophen-2-ylmethylthio)-1,2,4-triazole Following the procedure of Example 1(a)-1(d), except 2,4-dimethoxyphenyl isothiocyanate was substituted for phenylisothiocyanate in step 1(a) and 2-chloromethylthiophene was substituted for benzyl bromide in step 1(d), the title compound was prepared as a white solid. MS (ESI) 349.0 (M+H)$^+$.

Example 258

Preparation of 3-(2,4-dimethoxy-anilino)-5-(4-fluoro-benzylthio)-1,2,4-triazole

Following the procedure of Example 1(a)-1(d), except 2,4-dimethoxyphenyl isothiocyanate was substituted for phenylisothiocyanate in step 1(a) and 4-fluorobenzyl bromide was substituted for benzyl bromide in step 1(d), the title compound was prepared as a white solid. MS (ESI) 361.0 (M+H)$^+$.

Example 259

Preparation of 3-(2,4-dimethoxy-anilino)-5-(cyclo-hexylmethylthio)-1,2,4-triazole Following the procedure of Example 1(a)-1(d), except 2,4-dimethoxyphenyl isothiocyanate was substituted for phenylisothiocyanate in step 1(a) and bromomethylcyclohexane was substituted for benzyl bromide in step 1(d), the title compound was prepared as a white solid. MS (ESI) 349.0 (M+H)$^+$.

Example 260

Preparation of 3-(2,4-dimethoxy-anilino)-(3,4-difluoro-benzylthio)-1,2,4-triazole Following the procedure of Example 1(a)-1(d), except 2,4-dimethoxyphenyl isothiocyanate was substituted for phenylisothiocyanate in step 1(a) and 3,4-difluorobenzyl bromide was substituted for benzyl bromide in step 1(d), the title compound was prepared as a white solid. MS (ESI) 379.0 (M+H)⁺.

Example 261

Preparation of 3-(2,4-dimethoxy-anilino)-5-(2-methyl-2-butenylthio)-1,2,4-triazole Following the procedure of Example 1(a)-1(d), except 2,4-dimethoxyphenyl isothiocyanate was substituted for phenylisothiocyanate in step 1(a) and 1-bromo-3-methylbut-2-ene was substituted for benzyl bromide in step 1(d), the title compound was prepared as a white solid. MS (ESI) 321.2 (M+H)⁺.

Example 262

Preparation of 3-(2,4-dimethoxy-anilino)-5-(2-fluoro-benzylthio)-1,2,4-triazole

Following the procedure of Example 1(a)-1(d), except 2,4-dimethoxyphenyl isothiocyanate was substituted for phenylisothiocyanate in step 1(a) and 2-fluorobenzyl bromide was substituted for benzyl bromide in step 1(d), the title compound was prepared as a white solid. MS (ESI) 361.0 (M+H)⁺.

Example 263

Preparation of 3-(2,4-dimethoxy-anilino)-5-(2-methyl-benzylthio)-1,2,4-triazole

Following the procedure of Example 1(a)-1(d), except 2,4-dimethoxyphenyl isothiocyanate was substituted for phenylisothiocyanate in step 1(a) and 2-methylbenzyl bromide was substituted for benzyl bromide in step 1(d), the title compound was prepared as a white solid. MS (ESI) 357.2 (M+H)⁺.

Example 264

Preparation of 3-(2,4-dimethoxy-anilino)-5-(2-chloro-benzylthio)-1,2,4-triazole

Following the procedure of Example 1(a)-1(d), except 2,4-dimethoxyphenyl isothiocyanate was substituted for phenylisothiocyanate in step 1(a) and 2-chlorobenzyl bromide was substituted for benzyl bromide in step 1(d), the title compound was prepared as a white solid. MS (ESI) 377.0 (M+H)⁺.

Example 265

Preparation of 3-(2,4-dimethoxy-anilino)-5-(4-methoxy-benzylthio)-1,2,4-triazole Following the procedure of Example 1(a)-1(d), except 2,4-dimethoxyphenyl isothiocyanate was substituted for phenylisothiocyanate in step 1(a) and 4-methoxybenzyl chloride was substituted for benzyl bromide in step 1(d), the title compound was prepared as a white solid. MS (ESI) 373.2 (M+H)⁺.

Example 266

Preparation of 3-(2,4-dimethoxy-anilino)-5-(3,4-methylenedioxy-benzylthio)-1,2,4-triazole Following the procedure of Example 1(a)-1(d), except 2,4-dimethoxyphenyl isothiocyanate was substituted for phenylisothiocyanate in step 1(a) and 3,4-methylenedioxy-benzyl chloride was substituted for benzyl bromide in step 1(d), the title compound was prepared as a white solid. MS (ESI) 387.2 (M+H)⁺.

Example 267

Preparation of 3-(2,4-dimethoxy-anilino)-5-(5-methyl-isoxazol-3-ylmethylthio)-1,2,4-triazole Following the procedure of Example 1(a)-1(d), except 2,4-dimethoxyphenyl isothiocyanate was substituted for phenylisothiocyanate in step 1(a) and 3-(chloromethyl)-5-methylisoxazole was substituted for benzyl bromide in step 1(d), the title compound was prepared as a white solid. MS (ESI) 348.0 (M+H)⁺.

Example 268

Preparation of 3-(2,4-dimethoxy-anilino)-5-(pyridin-2-ylmethylthio)-1,2,4-triazole Following the procedure of Example 1(a)-1(d), except 2,4-dimethoxyphenyl isothiocyanate was substituted for phenylisothiocyanate in step 1(a) and 2-(chloromethyl)pyridine was substituted for benzyl bromide in step 1(d), the title compound was prepared as a white solid. MS (ESI) 344.2 (M+H)⁺.

Example 269

Preparation of 3-(2,4-dimethoxy-anilino)-5-(2-methoxy-benzylthio)-1,2,4-triazole Following the procedure of Example 1(a)-1(d), except 2,4-dimethoxyphenyl isothiocyanate was substituted for phenylisothiocyanate in step 1(a) and 2-methoxybenzyl chloride was substituted for benzyl bromide in step 1(d), the title compound was prepared as a white solid. MS (ESI) 373.2 (M+H)⁺.

Example 270

Preparation of 3-(2-methyl-4-methoxy-anilino)-5-benzylthio-1,2,4-triazole

Following the procedure of Example 1(a)-1(d), except 2-methyl-4-methoxyphenyl isothiocyanate was substituted for phenylisothiocyanate in step 1(a) the title compound was prepared as a white solid. MS (ESI) 327.2 (M+H)⁺.

Example 271

Preparation of 3-(2-methyl-4-methoxy-anilino)-5-(thiophen-2-ylmethylthio)-1,2,4-triazole Following the procedure of Example 1(a)-1(d), except 2-methyl-4-methoxyphenyl isothiocyanate was substituted for phenylisothiocyanate in step 1(a) and 2-chloromethylth-

Example 272

Preparation of 3-(2-methyl-4-methoxy-anilino)-5-(4-fluoro-benzylthio)-1,2,4-triazole Following the procedure of Example 1(a)-1(d), except 2-methyl-4-methoxyphenyl isothiocyanate was substituted for phenylisothiocyanate in step 1(a) and 4-fluorobenzyl bromide was substituted for benzyl bromide in step 1(d), the title compound was prepared as a white solid. MS (ESI) 345.0 (M+H)$^+$.

Example 273

Preparation of 3-(2-methyl-4-methoxy-anilino)-5-(cyclohexylmethylthio)-1,2,4-triazole Following the procedure of Example 1(a)-1(d), except 2-methyl-4-methoxyphenyl isothiocyanate was substituted for phenylisothiocyanate in step 1(a) and bromomethylcyclohexane was substituted for benzyl bromide in step 1(d), the title compound was prepared as a white solid. MS (ESI) 333.2 (M+H)$^+$.

Example 274

Preparation of 3-(2-methyl-4-methoxy-anilino)-5-(3,4-difluoro-benzylthio)-1,2,4-triazole Following the procedure of Example 1(a)-1(d), except 2-methyl-4-methoxyphenyl isothiocyanate was substituted for phenylisothiocyanate in step 1(a) and 3,4-difluorobenzyl bromide was substituted for benzyl bromide in step 1(d), the title compound was prepared as a white solid. MS (ESI) 363.0 (M+H)$^+$.

Example 275

Preparation of 3-(2-methyl-4-methoxy-anilino)-5-(2-methyl-2-butenylthio)-1,2,4-triazole Following the procedure of Example 1(a)-1(d), except 2-methyl-4-methoxyphenyl isothiocyanate was substituted for phenylisothiocyanate in step 1(a) and 1-bromo-3-methylbut-2-ene was substituted for benzyl bromide in step 1(d), the title compound was prepared as a white solid. MS (ESI) 305.2 (M+H)$^+$.

Example 276

Preparation of 3-(2-methyl-4-methoxy-anilino)-5-(2-fluoro-benzylthio)-1,2,4-triazole Following the procedure of Example 1(a)-1(d), except 2-methyl-4-methoxyphenyl isothiocyanate was substituted for phenylisothiocyanate in step 1(a) and 2-fluorobenzyl bromide was substituted for benzyl bromide in step 1(d), the title compound was prepared as a white solid. MS (ESI) 345.0 (M+H)$^+$.

Example 277

Preparation of 3-(2-methyl-4-methoxy-anilino)-5-(2-methyl-benzylthio)-1,2,4-triazole Following the procedure of Example 1(a)-1(d), except 2-methyl-4-methoxyphenyl isothiocyanate was substituted for phenylisothiocyanate in step 1(a) and 2-methylbenzyl bromide was substituted for benzyl bromide in step 1(d), the title compound was prepared as a white solid. MS (ESI) 341.2 (M+H)$^+$.

Example 278

Preparation of 3-(2-methyl-4-methoxy-anilino)-5-(2-chloro-benzylthio)-1,2,4-triazole Following the procedure of Example 1(a)-1(d), except 2-methyl-4-methoxyphenyl isothiocyanate was substituted for phenylisothiocyanate in step 1(a) and 2-chlorobenzyl bromide was substituted for benzyl bromide in step 1(d), the title compound was prepared as a white solid. MS (ESI) 361.0 (M+H)$^+$.

Example 279

Preparation of 3-(2-methyl-4-methoxy-anilino)-5-(4-methoxy-benzylthio)-1,2,4-triazole Following the procedure of Example 1(a)-1(d), except 2-methyl-4-methoxyphenyl isothiocyanate was substituted for phenylisothiocyanate in step 1(a) and 4-methoxybenzyl chloride was substituted for benzyl bromide in step 1(d), the title compound was prepared as a white solid. MS (ESI) 357.2 (M+H)$^+$.

Example 280

Preparation 3-(2-methyl-4-methoxy-anilino)-5-(3,4-methylenedioxy-benzylthio)-1,2,4-triazole Following the procedure of Example 1(a)-1(d), except 2-methyl-4-methoxyphenyl isothiocyanate was substituted for phenylisothiocyanate in step 1(a) and 3,4-methylenedioxybenzyl chloride was substituted for benzyl bromide in step 1(d), the title compound was prepared as a white solid. MS (ESI) 371.0 (M+H)$^+$.

Example 281

Preparation of 3-(2-methyl-4-methoxy-anilino)-5-(5-methyl-isoxazol-3-ylmethylthio)-1,2,4-triazole Following the procedure of Example 1(a)-1(d), except 2-methyl-4-methoxyphenyl isothiocyanate was substituted for phenylisothiocyanate in step 1(a) and 3-(chloromethyl)-5-methylisoxazole was substituted for benzyl bromide in step 1(d), the title compound was prepared as a white solid. MS (ESI) 332.2 (M+H)$^+$.

Example 282

Preparation of 3-(2-methyl-4-methoxy-anilino)-5-(pyridin-2-ylmethylthio)-1,2,4-triazole Following the procedure of Example 1(a)-1(d), except 2-methyl-4-methoxyphenyl isothiocyanate was substituted

Example 283

Preparation of 3-(2-methyl-4-methoxy-anilino)-5-(2-methoxy-benzylthio)-1,2,4-triazole Following the procedure of Example 1(a)-1(d), except 2-methyl-4-methoxyphenyl isothiocyanate was substituted for phenylisothiocyanate in step 1(a) and 2-methoxybenzyl chloride was substituted for benzyl bromide in step 1(d), the title compound was prepared as a white solid. MS (ESI) 357.2 (M+H)$^+$.

Example 284

Preparation of 3-(2,6-dimethyl-anilino)-5-benzylthio-1,2,4-triazole

Following the procedure of Example 1(a)-1(d), except 2,6-dimethylphenyl isothiocyanate was substituted for phenylisothiocyanate in step 1(a) the title compound was prepared as a white solid. MS (ESI) 311.4 (M+H)$^+$.

Example 285

Preparation of 3-(2,6-dimethyl-anilino)-5-(4-fluoro-benzylthio)-1,2,4-triazole

Following the procedure of Example 1(a)-1(d), except 2,6-dimethylphenyl isothiocyanate was substituted for phenylisothiocyanate in step 1(a) and 4-fluorobenzyl bromide was substituted for benzyl bromide in step 1(d), the title compound was prepared as a white solid. MS (ESI) 329.2 (M+H)$^+$.

Example 286

Preparation of 3-(2,6-dimethyl-anilino)-5-(cyclohexylmethylthio)-1,2,4-triazole

Following the procedure of Example 1(a)-1(d), except 2,6-dimethylphenyl isothiocyanate was substituted for phenylisothiocyanate in step 1(a) and bromomethylcyclohexane was substituted for benzyl bromide in step 1(d), the title compound was prepared as a white solid. MS (ESI) 317.2 (M+H)$^+$.

Example 287

Preparation of 3-(2,6-dimethyl-anilino)-(3,4-difluoro-benzylthio)-1,2,4-triazole Following the procedure of Example 1(a)-1(d), except 2,6-dimethylphenyl isothiocyanate was substituted for phenylisothiocyanate in step 1(a) and 3,4-difluorobenzyl bromide was substituted for benzyl bromide in step 1(d), the title compound was prepared as a white solid. MS (ESI) 347.0 (M+H)$^+$.

Example 288

Preparation of 3-(2,6-dimethyl-anilino)-5-(2-methyl-2-butenylthio)-1,2,4-triazole Following the procedure of Example 1(a)-1(d), except 2,6-dimethylphenyl isothiocyanate was substituted for phenylisothiocyanate in step 1(a) and 1-bromo-3-methylbut-2-ene was substituted for benzyl bromide in step 1(d), the title compound was prepared as a white solid. MS (ESI) 289.0 (M+H)$^+$.

Example 289

Preparation of 3-(2,6-dimethyl-anilino)-5-(2-fluoro-benzylthio)-1,2,4-triazole

Following the procedure of Example 1(a)-1(d), except 2,6-dimethylphenyl isothiocyanate was substituted for phenylisothiocyanate in step 1(a) and 2-fluorobenzyl bromide was substituted for benzyl bromide in step 1(d), the title compound was prepared as a white solid. MS (ESI) 329.2 (M+H)$^+$.

Example 290

Preparation of 3-(2,6-dimethyl-anilino)-5-(2-methyl-benzylthio)-1,2,4-triazole

Following the procedure of Example 1(a)-1(d), except 2,6-dimethylphenyl isothiocyanate was substituted for phenylisothiocyanate in step 1(a) and 2-methylbenzyl bromide was substituted for benzyl bromide in step 1(d), the title compound was prepared as a white solid. MS (ESI) 325.2 (M+H)$^+$.

Example 291

Preparation of 3-(2,6-dimethyl-anilino)-5-(2-chloro-benzylthio)-1,2,4-triazole

Following the procedure of Example 1(a)-1(d), except 2,6-dimethylphenyl isothiocyanate was substituted for phenylisothiocyanate in step 1(a) and 2-chlorobenzyl bromide was substituted for benzyl bromide in step 1(d), the title compound was prepared as a white solid. MS (ESI) 345.0 (M+H)$^+$.

Example 292

Preparation of 3-(4-fluoro-anilino)-5-(furan-2-ylmethylthio)-1,2,4-triazole

Following the procedure of Example 1(a)-1(d), except 4-fluorophenyl isothiocyanate was substituted for phenylisothiocyanate in step 1(a) and 2-chloromethyl-furan (Berry, J. M.; Watson, C. Y.; Whish, W. J. D.; Threadgill, M. D. *J. Chem. Soc. Perkin Trans.* 1 1997, 8, 1147) was substituted for benzyl bromide in step 1(d), the title compound was prepared as a white solid. MS (ESI) 291.2 (M+H)$^+$.

Example 293

Preparation of 3-(4-fluoro-anilino)-5-(3-methyl-thiophen-2-ylmethylthio)-1,2,4-triazole Following the procedure of Example 1(a)-1(d), except 4-fluorophenyl isothiocyanate was substituted for phenylisothiocyanate in step 1(a) and 2-chloromethyl-3-methyl-thiophene (Chauhan, P. M. S.; Jenkins, G.; Walker, S. M.; Storr, R. C. *Tetrahedron Lett.* 1988, 29(1), 117) was substituted for benzyl bromide in step 1(d), the title compound was prepared as a white solid. MS (ESI) 321.0 (M+H)$^+$.

Example 294

Preparation of 3-(4-fluoro-anilino)-5-(3-chloro-thiophen-2-ylmethylthio)-1,2,4-triazole Following the procedure of Example 1(a)-1(d), except 4-fluorophenyl isothiocyanate was substituted for phenylisothiocyanate in step 1(a) and 2-chloromethyl-3-chloro-thiophene (Chauhan, P. M. S.; Jenkins, G.; Walker, S. M.; Storr, R. C. *Tetrahedron Lett.* 1988, 29(1), 117) was substituted for benzyl bromide in step 1(d), the title compound was prepared as a white solid. MS (ESI) 341.2 (M+H)$^+$.

Example 295

Preparation of 3-(4-fluoro-anilino)-5-(5-methyl-thiophen-2-ylmethylthio)-1,2,4-triazole Following the procedure of Example 1(a)-1(d), except 4-fluorophenyl isothiocyanate was substituted for phenylisothiocyanate in step 1(a) and 2-chloromethyl-5-methyl-thiophene (Moradpour, A. *J. Chem. Soc. Perkin Trans.* 1, 1993, 1, 7) was substituted for benzyl bromide in step 1(d), the title compound was prepared as a white solid. MS (ESI) 321.0 (M+H)$^+$.

Example 296

Preparation of 3-(4-fluoro-anilino)-5-(5-chloro-thiophen-2-ylmethylthio)-1,2,4-triazole Following the procedure of Example 1(a)-1(d), except 4-fluorophenyl isothiocyanate was substituted for phenylisothiocyanate in step 1(a) and 2-chloromethyl-5-chloro-thiophene was substituted for benzyl bromide in step 1(d), the title compound was prepared as a white solid. MS (ESI) 341.2 (M+H)$^+$.

Example 297

Preparation of 5-(5-(4-fluorophenylamino)-4H-[1,2,4]triazol-3-ylsulfanylmethyl)-furan-2-carboxylic Acid Ethyl Ester Following the procedure of Example 1(a)-1(d), except 4-fluorophenyl isothiocyanate was substituted for phenylisothiocyanate in step 1(a) and 5-chloromethyl-furan-2-carboxylic acid ethyl ester was substituted for benzyl bromide in step 1(d), the title compound was prepared as a white solid. MS (ESI) 363.2 (M+H)$^+$.

Example 298

Preparation of 3-(4-fluoro-anilino)-5-(5-bromo-thiophen-2-ylmethylthio)-1,2,4-triazole Following the procedure of Example 1(a)-1(d), except 4-fluorophenyl isothiocyanate was substituted for phenylisothiocyanate in step 1(a) and 2-chloromethyl-5-bromo-thiophene (Clapp, R. C.; Clark, J. H; Vaughan, J. R.; English, J. P.; Anderson, G. W. *J. Am. Chem. Soc.* 1947, 60, 1549) was substituted for benzyl bromide in step 1(d), the title compound was prepared as a white solid. MS (ESI) 385.0 (M)$^+$.

Example 299

Preparation of 5-(5-(4-fluorophenylamino)-4H-[1,2,4]triazol-3-ylsulfanylmethyl)-furan-2-carbaldehyde Following the procedure of Example 1(a)-1(d), except 4-fluorophenyl isothiocyanate was substituted for phenylisothiocyanate in step 1(a) and 5-chloromethyl-furan-2-carbaldehyde (Sanda, K.; Rigal, L.; Delmas, M.; Gaset, A. *Synthesis* 1992, 6, 541) was substituted for benzyl bromide in step 1(d), the title compound was prepared as a white solid. MS (ESI) 319.0 (M+H)$^+$.

Example 300

Preparation of 3-(4-fluoro-anilino)-5-(thiophen-3-ylmethylthio)-1,2,4-triazole

Following the procedure of Example 1(a)-1(d), except 4-fluorophenyl isothiocyanate was substituted for phenylisothiocyanate in step 1(a) and 3-chloromethyl-thiophene (Lamy, J.; Lavit, D.; Buu-Hoi, N. P. *J. Chem. Soc.* 1958, 4202) was substituted for benzyl bromide in step 1(d), the title compound was prepared as a white solid. MS (ESI) 307.2 (M+H)$^+$.

Example 301

Preparation of 3-(4-fluoro-anilino)-5-(furan-3-ylmethylthio)-1,2,4-triazole

Following the procedure of Example 1(a)-1(d), except 4-fluorophenyl isothiocyanate was substituted for phenylisothiocyanate in step 1(a) and 3-chloromethyl-furan (Arena, G.; Cali, R.; Maccarone, E.; Passerini, A. *J. Chem. Soc. Perkin Trans.* 2 1993, 10, 1941) was substituted for benzyl bromide in step 1(d), the title compound was prepared as a white solid. MS (ESI) 291.2 (M+H)$^+$.

Example 302

Preparation of 3-methyl-3-anilino-5-benzylthio-1,2,4-triazole a) 3-anilino-5-benzylthio-1 or/2-methyl ethyl ether-1,2,4-triazole To a stirring solution of 3-anilino-5-benzylthio-1,2,4-triazole (0.68 g, 2.41 mmol) in 8 mL DMF was added NaH (0.125 g, 3.13 mmol). To this mixture was added chloromethyl ethyl ether (0.251 g, 2.65 mmol), and the solution was stirred overnight. The reaction mixture was poured into 50 ml H$_2$O and extracted three times with EtOAc. The EtOAc extracts were dried over Na$_2$SO$_4$, filtered, and concentrated down. The crude mixture was subjected to column chromatography (silica gel, EtOAc/hexane) to provide the title compounds as a mixture of regioisomers as a light yellow oil (0.58 g, 71%). $^1$H-NMR (400 MHz, d6-DMSO) compound 1: δ9.33 (broad singlet, 1H), 7.51 (d, 2H, J=8.3 Hz), 7.42-7.22 (m, 8H), 5.23 (s, 2H), 4.47 (s, 2H), 3.43 (q, 2H, J=7.2 Hz), 1.04 (t, 3H, J=7.0 Hz). Compound 2: δ9.20 (broad singlet, 1H), 7.63 (d, 2H, J=7.6 Hz), 7.42-6.93 (m, 8H), 5.44 (s, 2H), 4.30 (s, 2H), 3.51 (q, 2H, J=7.1 Hz), 1.07 (t, 3H, J=7.0). MS (ESI) 341 (M+H)$^+$.

b) 3-methyl-3-anilino-5-benzylthio-1,2,4-triazole

To a stirring solution of 3-anilino-5-benzylthio-1 or/2-methyl ethyl ether-1,2,4-triazole (50 mg, 0.15 mmol) in 1 ml THF was added NaH (11.8 mg, 0.30 mmol), and to this solution was added CH$_3$I (0.036 ml, 0.57 mmol). The reaction mixture was stirred overnight. THF was removed and 0.5 ml TFA was added to the residue and stirred overnight. TFA was removed under vacuum and the mixture was purified by preparative HPLC to afford the title compound as a clear oil (28 mg, 53%). $^1$H-NMR (400 MHz, d6-DMSO) δ3.3-7.25 (m, 10H), 4.27 (s, 2H), 3.40 (s, 3H). MS (ESI) 297 (M+H)$^+$.

Example 303

Preparation of 3-ethyl-3-anilino-5-benzylthio-1,2,4-triazole

Following the procedure of Example 302(a)-(b) except iodoethane was used in step 302(b) instead of iodomethane, the title compound was isolated as a white solid. $^1$H-NMR (400 MHz, d6-DMSO) δ7.42-7.26 (m, 10H), 4.26 (s, 2H), 3.86 (m, 2H), 1.20 (m, 3H). MS (ESI) 311 (M+H)$^+$.

Example 304

Preparation of 3-n-propyl-3-anilino-5-benzylthio-1,2,4-triazole

Following the procedure of Example 302(a)-(b) except 1-iodopropane was used in step 302(b) instead of iodomethane, the title compound was isolated as a white solid (35%). $^1$H-NMR (400 MHz, d6-DMSO) δ7.42-7.26 (m, 10H), 4.25 (s, 2H), 3.76 (t, 2H, J=6.5 Hz), 3.31 (t, 2H, J=1.4 Hz), 1.63 (m, 2H), 0.93 (t, 3H, J=7.4 Hz). MS (ESI) 325 (M+H)$^+$.

Example 305

Preparation of 3-n-butyl-3-anilino-5-benzylthio-1,2,4-triazole

Following the procedure of Example 302(a)-(b) except 1-iodobutane was used in step 302(b) instead of iodomethane, the title compound was isolated as a white solid (31%). $^1$H-NMR (400 MHz, d6-DMSO) δ7.42-7.22 (m, 10H), 4.26 (s, 2H), 3.80 (t, 2H, J=7.5 Hz), 3.31 (t, 2H, J=1.4 Hz), 1.59 (m, 2H), 1.36 (m, 2H), 0.92 (t, 3H, J=7.3 Hz). MS (ESI) 338 (M+H)$^+$.

Example 306

Preparation of 3-isopropyl-3-anilino-5-benzylthio-1,2,4-triazole

Following the procedure of Example 302(a)-(b) except 1-iodo-2-methyl propane was used in step 302(b) instead of iodomethane, the title compound was isolated as a white solid. $^1$H-NMR (400 MHz, d6-DMSO) δ7.42-7.22 (m, 10H), 4.25 (s, 2H), 3.66 (d, 2H, J=7.6 Hz), 1.92 (m, 1H), 0.93 (d, 6H, J=6.7 Hz). MS (ESI) 338 (M+H)$^+$.

Example 307

Preparation of 3-allyl-3-anilino-5-benzylthio-1,2,4-triazole

Following the procedure of Example 302(a)-(b) except allyl bromide was used in step 302(b) instead of iodomethane, the title compound was isolated as a white solid (41%). $^1$H-NMR (400 MHz, d6-DMSO) δ7.37-7.28 (m, 10H), 5.96 (m, 1H), 5.18 (m, 2H), 4.45 (s, 2H), 4.26 (s, 2H). MS (ESI) 323 (M+H)$^+$.

Example 308

Preparation of 3-benzyl-3-anilino-5-benzylthio-1,2,4-triazole

Following the procedure of Example 302(a)-(b) except benzyl bromide was used in step 302(b) instead of iodomethane, the title compound was isolated as a white solid (48%). $^1$H-NMR (400 MHz, d6-DMSO) δ7.28-7.23 (m, 15H), 5.09 (s, 2H), 4.26 (s, 2H). MS (ESI) 373 (M+H)$^+$.

Example 309

Preparation of 3-methylacetate-3-anilino-5-benzylthio-1,2,4-triazole

Following the procedure of Example 302(a)-(b) except methyl bromoacetate was used in step 302(b) instead of iodomethane, the title compound was isolated as a white solid. $^1$H-NMR (400 MHz, d6-DMSO) δ7.37-7.22 (m, 10H), 4.59 (s, 2H), 4.26 (s, 2H), 3.74 (s, 3H). MS (ESI) 355 (M+H)$^+$.

Example 310

Preparation of 3-methylacetate-3-(p-methyl)-anilino-5-benzylthio-1,2,4-triazole

Following the procedure of Example 302(a)-(b) except 3-(p-methyl)-anilino-5-benzylthio-1,2,4-triazole was used in step 302(a) instead of 3-anilino-5-benzylthio-1,2,4-triazole and methyl bromoacetate was used in step 302(b) instead of iodomethane, the title compound was isolated as a clear oil. $^1$H-NMR (400 MHz, d6-DMSO) δ7.38-7.09 (m, 9H), 4.56 (s, 2H), 4.27 (s, 2H), 3.75 (s, 3H), 2.37 (s, 3H). MS (ESI) 369 (M+H)$^+$.

Example 311

Preparation of 3-methylacetate-3-(p-methoxy)-anilino-5-benzylthio-1,2,4-triazole Following the procedure of Example 302(a)-(b) except 3-(p-methoxy)-anilino-5-benzylthio-1,2,4-triazole was used in step 302(a) instead of 3-anilino-5-benzylthio-1,2,4-triazole and methyl bromoacetate was used in step 302(b) instead of iodomethane, the title compound was isolated as a brown oil (44%). $^1$H-NMR (400 MHz, d6-DMSO) δ7.92-7.22 (m, 7H), 6.99 (d, 2H, J=8.9 Hz), 4.51 (s, 2H), 4.26 (s, 2H), 3.83 (s, 3H), 3.76 (s, 3H). MS (ESI) 385 (M+H)$^+$.

Example 312

Preparation of 3-methylacetate-3-(2,6-dimethyl)-anilino-5-benzylthio-1,2,4-triazole Following the procedure of Example 302(a)-(b) except 3-(2,6-dimethyl)-anilino-5-benzylthio-1,2,4-triazole was used in step 302(a) instead of 3-anilino-5-benzylthio-1,2,4-triazole and methyl bromoacetate was used in step 302(b) instead of iodomethane, the title compound was isolated as a white solid (43%). $^1$H-NMR (400 MHz, d6-DMSO) δ7.32-7.19 (m, 8H), 4.37 (s, 2H), 4.25 (s, 2H), 3.77 (s, 3H), 2.27 (s, 6H). MS (ESI) 383 (M+H)$^+$.

Biological Data:

Direct Spectrophotometric Assays of hMetAP2:

The hMetAP2 activity can be measured by direct spectrophotometric assay methods using alternative substrates, L-methionine-p-nitroanilide (Met-pNA) and L-methionine-7-amido-4-methylcoumarin (Met-AMC). The formation of p-nitroaniline (pNA) or 7-amido-4-methylcoumarin (AMC) was continuously monitored by increasing absorbance or fluorescence at 405 nm and 460 nm, respectively, on a corresponding plate reader. All assays were carried out at 30° C. The fluorescence or spectrophotometric plate reader was calibrated using authentic pNA and AMC from Sigma, respectively. For a typical 96-well plate assay, the increase in the absorbance (at 405 nm for pNA) or the fluorescence emission ($\lambda_{ex}$=360 nm, $\lambda_{em}$=460 nm, for AMC) of a 50 μL assay solution in each well was used to calculate the initial velocity of hMetAP2. Each 50 μL assay solution, contained 50 mM Hepes.Na$^+$ (pH 7.5), 100 mM NaCl, 10-100 nM purified hMetAP2 enzyme, and varying amounts of Met-AMC (in 3% DMSO aqueous solution) or Met-pNA. Assays were initiated with the addition of substrate and the initial rates were corrected for the background rate determined in the absence of hMetAP2.

Coupled Spectrophotometric Assays of hMetAP2:

The methionine aminopeptidase activity of hMetAP2 can also be measured spectrophotometrically by monitoring the free L-amino acid formation. The release of N-terminal methionine from a tripeptide (Met-Ala-Ser, Sigma) or a tetrapeptide (Met-Gly-Met-Met, Sigma) substrate was assayed using the L-amino acid oxidase (AAO)/horse radish peroxidase (HRP) couple (eq. 1-3a,b). The formation of hydrogen peroxide (H$_2$O$_2$) was continuously monitored at 450 nm (absorbance increase of o-Dianisidine (Sigma) upon oxidation, Δε=15,300 M$^{-1}$ cm$^{-1}$)$^2$ and 30° C. in a 96- or 384-well plate reader by a method adapted from Tsunasawa, S. et al. (1997) (eq. 3a). Alternatively, formation of H$_2$O$_2$ was followed by monitoring the fluorescence emission increase at 587 nm (Δε=54,000 M$^{-1}$ cm$^{-1}$, $\lambda_{ex}$=563 nm, slit width for both excitation and emission was 1.25 mm) and 30° C. using Amplex Red (Molecular Probes, Inc) (Zhou, M. et al. (1997) Anal. Biochem. 253, 162) (eq. 3b). In a total volume of 50 μL, a typical assay contained 50 mM Hepes.Na$^+$, pH 7.5, 100 mM NaCl, 10 μM CoCl$_2$, 1 mM o-Dianisidine or 50 μM Amplex Red, 0.5 units of HRP (Sigma), 0.035 unit of AAO (Sigma), 1 nM hMetAP2, and varying amounts of peptide substrates. Assays were initiated by the addition of hMetAP2 enzyme, and the rates were corrected for the background rate determined in the absence of hMetAP2.

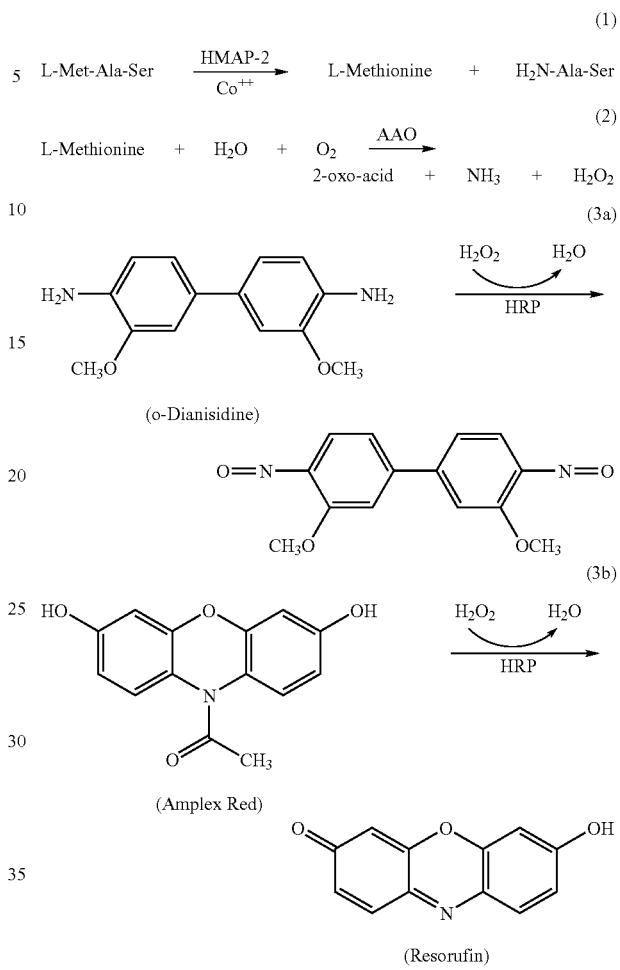

Kinetic Data Analysis:

Data were fitted to the appropriate rate equations using Grafit computer software. Initial velocity data conforming to Michaelis-Menton kinetics were fitted to eq. 4. Inhibition patterns conforming to apparent competitive and non-competitive inhibition were fitted to eq. 5 and eq. 6, respectively.

$$v = VA/(K_a + A) \tag{4}$$

$$v = VA/[K_a(1+I/K_{is}) + A] \tag{5}$$

$$v = VA/[K_a(1+I/K_{is}) + A(1+I/K_{ii})] \tag{6}$$

In eqs. 4-6, v is the initial velocity, V is the maximum velocity, $K_a$ is the apparent Michaelis constant, I is the inhibitor concentration, and A is the concentration of variable substrates. The nomenclature used in the rate equations for inhibition constants is that of Cleland (1963), in which $K_{is}$ and $K_{ii}$ represent the apparent slope and intercept inhibition constants, respectively.

Cell Growth Inhibition Assays:

The ability of MetAP2 inhibitors to inhibit cell growth was assessed by the standard XTT microtitre assay. XTT, a dye sensitive to the pH change of mitochondria in eukaryotic cells, is used to quantify the viability of cells in the presence of chemical compounds. Cells seeded at a given number undergo approximately two divisions on average in the 72 hours of incubation. In the absence of any compound, this population of cells is in exponential growth at the end of the incubation period; the mitochondrial activity of these cells is reflected in the spectrophotometric readout (A450). Viability of a similar cell population in the presence of a given concentration of compound is assessed by comparing the A450 reading from the test well with that of the control well. Flat-bottomed 96-well plates are seeded with appropriate numbers of cells (4-6×10³ cells/well in a volume of 200 ul) from trypsinized exponentially growing cultures. In the case of HUVECs, the wells are coated with matrigel prior to establishing the cultures. To "blank" wells is added growth medium only. Cells are incubated overnight to permit attachment. Next day, medium from wells that contain cells is replaced with 180 ul of fresh medium. Appropriate dilutions of test compounds are added to the wells, final DMSO concentration in all wells being 0.2%. Cells plus compound are incubated for an additional 72 hr at 37° C. under the normal growth conditions of the cell line used. Cells are then assayed for viability using standard XTT/PMS (prepared immediately before use: 8 mg XTT (Sigma X-4251) per plate is dissolved in 100 ul DMSO. 3.9 ml $H_2O$ is added to dissolve XTT and 20 ul of PMS stock solution (30 mg/ml) is added from frozen aliquoted stock solution (10 mg of PMS (phenazine methosulfate, Sigma P-9625) in 3.3 ml PBS without cations. These stocks are frozen at -20° C. until use). 50 ul of XTT/PMS solution is added to each well and plates incubated for 90 minutes (time required may vary according to cell line, etc.) at 37° C. until $A_{450}$ is >1.0. Absorbance at 450 nM is determined using a 96-well UV plate reader. Percent viability of cells in each well is calculated from these data (having been corrected for background absorbance). IC50 is that concentration of compound that reduces cell viability to 50% control (untreated) viability.

The compounds of this invention show MetAP2 inhibitor activity having $IC_{50}$ values in the range of 0.0001 to 100 uM. The full structure/activity relationship has not yet been established for the compounds of this invention. However, given the disclosure herein, one of ordinary skill in the art can utilize the present assays in order to determine which compounds of this invention are inhibitors of MetAP2 and which bind thereto with an $IC_{50}$ value in the range of 0.0001 to 100 uM.

All publications, including, but not limited to, patents and patent applications cited in this specification, are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration it is believed that one skilled in the art can, given the preceding description, utilize the present invention to its fullest extent. Therefore any examples are to be construed as merely illustrative and not a limitation on the scope of the present invention in any way. The embodiments of the invention in which an exclusive property or privilege is claimed are defined as follows.

What is claimed is:

1. A compound of Formula (I), or a pharmaceutically acceptable salt or solvate thereof:

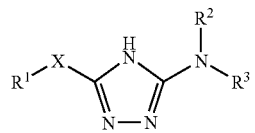

Formula (I)

wherein:
X is S;
$R^1$ is optionally substituted furan-$C_1$alkyl;
$R^2$ is optionally substituted Ar—$C_{0-6}$alkyl; and
$R^3$ is H, optionally substituted $C_{1-6}$alkyl, $C_{3-6}$alkenyl, or $C_{3-6}$alkynyl.

2. The compound according to claim 1, selected from the group consisting of:
 5-(5-phenylamino-4H-[1,2,4]triazol-3-ylsulfanylmethyl)-furan-2-carboxylic acid ethyl ester;
 5-(5-phenylamino-4H-[1,2,4]triazol-3-ylsulfanylmethyl)-furan-2-carbaldehyde;
 5-(5-p-tolyl amino-4H-[1,2,4]triazol-3-ylsulfanylmethyl)-furan-2-carboxylic acid ethyl ester;
 5-(5-p-tolyl amino-4H-[1,2,4]triazol-3-ylsulfanylmethyl)-furan-2-carbaldehyde;
 5-(5-o-tolyl amino-4H-[1,2,4]triazol-3-ylsulfanylmethyl)-furan-2-carboxylic acid ethyl ester;
 5-(5-o-tolyl amino-4H-[1,2,4]triazol-3-ylsulfanylmethyl)-furan-2-carbaldehyde;
 3-(2-methyl-anilino)-5-(furan-3-ylmethylthio)-1,2,4-triazole;
 3-(2-methoxy-anilino)-5-(furan-2-ylmethylthio)-1,2,4-triazole;
 5-(5-(2-methoxyphenylamino)-4H-[1,2,4]triazol-3-ylsulfanylmethyl)-furan-2-carboxylic acid ethyl ester
 3-(2-methoxy-anilino)-5-(furan-3-ylmethylthio)-1,2,4-triazole;
 5-(5-(3-methylphenylamino)-4H-[1,2,4]triazol-3-ylsulfanylmethyl)-furan-2-carboxylic acid ethyl ester;
 5-(5-(3-methylphenylamino)-4H-[1,2,4]triazol-3-ylsulfanylmethyl)-furan-2-carbaldehyde;
 3-(4-fluoro-anilino)-5-(furan-2-ylmethylthio)-1,2,4-triazole;
 5-(5-(4-fluorophenylamino)-4H-[1,2,4]triazol-3-ylsulfanylmethyl)-furan-2-carboxylic acid ethyl ester;
 5-(5-(4-fluorophenylamino)-4H-[1,2,4]triazol-3-ylsulfanylmethyl)-furan-2-carbaldehyde; and
 3-(4-fluoro-anilino)-5-(furan-3-ylmethylthio)-1,2,4-triazole or a pharmaceutically acceptable salt or solvate thereof.

3. The compound according to claim 1, selected from the group consisting of:
 3-anilino-5-(furan-3-ylmethylthio)-1,2,4-triazole;
 3-anilino-5-(furan-2-ylmethylthio)-1,2,4-triazole;
 3-(2-methyl-anilino)-5-(furan-2-ylmethylthio)-1,2,4-triazole;
 3-(3-methyl-anilino)-5-(furan-2-ylmethylthio)-1,2,4-triazole; and
 3-(3-methyl-anilino)-5-(furan-3-ylmethylthio)-1,2,4-triazole; or
 a pharmaceutically acceptable salt or solvate thereof.

4. The compound according to claim 1, selected from the group consisting of:
 3-(2-isopropyl-anilino)-5-(furan-2-ylmethylthio)-1,2,4-triazole;

5-(5-(2-isopropylphenylamino)-4H-[1,2,4]triazol-3-yl-sulfanylmethyl)-furan-2-carboxylic acid ethyl ester;

5-(5-(2-isopropyl amino)-4H-[1,2,4]triazol-3-ylsulfanyl-methyl)-furan-2-carbaldehyde;

3-(2-isopropyl-anilino)-5-(furan-3-ylmethylthio)-1,2,4-triazole;

3-(4-methyl-anilino)-5-(furan-2-ylmethylthio)-1,2,4-triazole; and 3-(4-methyl-anilino)-5-(furan-3-ylmethylthio)-1,2,4-triazole;

or a pharmaceutically acceptable salt or solvate thereof.

5. A pharmaceutical composition comprising the compound according to claim 1, or a pharmaceutically acceptable salt or solvate thereof, and a pharmaceutically acceptable carrier.

6. A pharmaceutical composition comprising the compound according to claim 2, or a pharmaceutically acceptable salt or solvate thereof, and a pharmaceutically acceptable carrier.

7. A pharmaceutical composition comprising the compound according to claim 3, or a pharmaceutically acceptable salt or solvate thereof, and a pharmaceutically acceptable carrier.

8. A pharmaceutical composition comprising the compound according to claim 4, or a pharmaceutically acceptable salt or solvate thereof, and a pharmaceutically acceptable carrier.

9. A method of making the compound of Formula (I) according to claim 1, wherein X, $R^1$, $R^2$, and $R^3$ are as defined in claim 1, comprising the steps of:

a) combining an isothiocyanate of Formula (II):

$R^2$NCS (Formula II)

with thiourea to provide a compound of Formula (III):

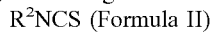

Formula (III)

b) treating the compound of Formula (III) with an alkyl halide under basic conditions to provide a compound of Formula (IV):

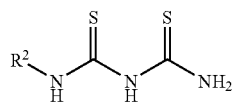

Formula (IV)

c) treating the compound of formula (IV) with hydrazine to provide a compound of Formula (V):

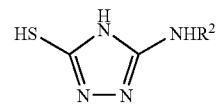

Formula (V)

d) treating the compound of formula (V) with an alkyl halide under basic conditions to provide a compound of Formula (VI):

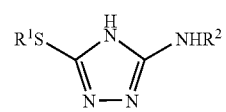

Formula (VI)

e) protecting the compound of formula (VI) to provide a compound of Formula (VII):

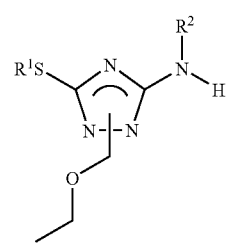

Formula (VII)

f) alkylating the compound of formula (VII) with an alkyl halide to provide a compound of Formula (VIII):

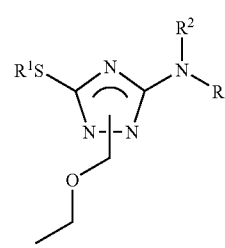

Formula (VIII)

g) deprotecting the compound of formula (VIII) to provide the compound of Formula (I).

* * * * *